(12) United States Patent
Paterson

(10) Patent No.: US 10,010,593 B2
(45) Date of Patent: Jul. 3, 2018

(54) **RECOMBINANT *LISTERIA* VACCINE STRAINS AND METHODS OF USING THE SAME IN CANCER IMMUNOTHERAPY**

(71) Applicant: The Trustees of the University of Pennsylvania, Philadelphia, PA (US)

(72) Inventor: Yvonne Paterson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/883,557

(22) Filed: Oct. 14, 2015

(65) Prior Publication Data

US 2016/0367650 A1 Dec. 22, 2016

Related U.S. Application Data

(60) Provisional application No. 62/063,828, filed on Oct. 14, 2014, provisional application No. 62/065,973, filed on Oct. 20, 2014.

(51) Int. Cl.

| | |
|---|---|
| *A61K 39/00* | (2006.01) |
| *C07K 16/30* | (2006.01) |
| *A61K 31/407* | (2006.01) |
| *A61K 31/513* | (2006.01) |
| *A61K 39/12* | (2006.01) |
| *A61N 5/10* | (2006.01) |
| *C12N 7/00* | (2006.01) |

(52) U.S. Cl.
CPC ........ *A61K 39/0011* (2013.01); *A61K 31/407* (2013.01); *A61K 31/513* (2013.01); *A61K 39/12* (2013.01); *A61N 5/10* (2013.01); *C07K 16/3046* (2013.01); *C12N 7/00* (2013.01); *A61K 2039/522* (2013.01); *A61K 2039/523* (2013.01); *A61K 2039/54* (2013.01); *A61K 2039/545* (2013.01); *A61K 2039/572* (2013.01); *A61K 2039/585* (2013.01); *A61K 2039/6037* (2013.01); *C12N 2710/20034* (2013.01)

(58) Field of Classification Search
None
See application file for complete search history.

(56) References Cited

U.S. PATENT DOCUMENTS

| 6,767,542 B2 | 7/2004 | Paterson et al. |
|---|---|---|
| 8,114,484 B2 | 2/2012 | Yang et al. |
| 2004/0013690 A1 | 1/2004 | Portnoy et al. |
| 2005/0048081 A1 | 3/2005 | Frankel et al. |
| 2005/0118184 A1 | 6/2005 | Paterson et al. |
| 2006/0104991 A1* | 5/2006 | Paterson ............... A61K 35/74 424/200.1 |
| 2011/0142791 A1 | 6/2011 | Shahabi |
| 2011/0223187 A1 | 9/2011 | Shahabi |

FOREIGN PATENT DOCUMENTS

| WO | WO 2004/084936 A2 | 10/2004 |
|---|---|---|
| WO | WO 2004/110481 A2 | 12/2004 |
| WO | WO 2015/134722 A2 | 9/2015 |
| WO | WO 2015/16412 A1 | 10/2015 |

OTHER PUBLICATIONS

Maciag et al. (Vaccine, 27:3975-3983, 2009).*
Verch et al. (Infect. Immun., 72:6418-6425, 2004).*
Anthony PP "Precursor lesions for liver cancer in humans" Cancer Research. Jul. 1, 1976;36(7 Part 2):2579-83.
Auerbuch et al. Development of a competitive index assay to evaluate the virulence of Listeria monocytogenes actAmutants during primary and secondary infection of mice. Infection and immunity. Sep. 1, 2001;69(9):5953-7.
Beatty et al. "IFN-γ-dependent inhibition of tumor angiogenesis by tumor-infiltrating CD4+ T cells requires tumor responsiveness to IFN-γ" The Journal of Immunology. Feb. 15, 2001;166(4):2276-82.
Benvegnu et al. "Space-occupying lesions of the liver detected by ultrasonography and their relation to hepatocellular carcinoma in cirrhosis" Liver. Apr. 1, 1992;12(2):80-3.
Bishop et al. "Adoptive transfer of immunity to Listeria monocytogenes. The influence of in vitro stimulation on lymphocyte subset requirements" The Journal of Immunology. Sep. 15, 1987;139(6):2005-9.
Bodanszky M, Bodanszky A. "Protecting groups" In 'The practice of peptide synthesis' 1984 (pp. 7-85). Springer Berlin Heidelberg.
Brockstedt et al. "Listeria-based cancer vaccines that segregate immunogenicity from toxicity" Proceedings of the National Academy of Sciences of the United States of America. Sep. 21, 2004;101(38):13832-7.
Dominiecki et al. "Tumor sensitivity to IFN-γ is required for successful antigen-specific immunotherapy of a transplantable mouse tumor model for HPV-transformed tumors". Cancer Immunology, Immunotherapy. May 1, 2005;54(5):477-88.
Frachon et al. "Endothelial cell marker expression in dysplastic lesions of the liver: an immunohistochemical study" Journal of hepatology. Jun. 30, 2001;34(6):850-7.
Garay-Malpartida et al. "CaSPredictor: a new computer-based tool for caspase substrate prediction" Bioinformatics. Jun. 1, 2005;21(suppl 1):i169-76.
GenBank Accession. No. P499521; Oct. 4, 2014.
GenBank Accession No. EAW68222.1; May 14, 2014.
GenBank Accession. No. NM_003219.1 (variant 1); Jun. 18, 2006.
GenBank Accession No. NM_198255.2 (variant 2); Jul. 18, 2010.
GenBank Accession No. NM_198254.1 (variant 4); Jun. 18, 2006.
GenBank Accession No. ABI73976.1; Sep. 19, 2006.
GenBank Accession No. NP_001003075.1; Jan. 26, 2014.
GenBank Accession No. NP_999506.1; Jan. 10, 2014.
GenBank Accession No. EAW58359.1; May 14, 2014.

(Continued)

*Primary Examiner* — Brian Gangle
(74) *Attorney, Agent, or Firm* — Mark S. Cohen; Pearl Cohen; Zedek Latzer Baratz LLP

(57) ABSTRACT

The present invention provides methods of treating, protecting against, and inducing an immune response against a human papillomavirus-associated oropharyngeal tumor or cancer, comprising the step of administering to a subject a recombinant *Listeria* strain expressing a human papillomavirus antigen.

28 Claims, 37 Drawing Sheets

(56) References Cited

OTHER PUBLICATIONS

GenBank Accession No. NP_647466.2; Sep. 5, 2014.
GenBank Accession No. AAC51660.1; Jun. 23, 2010.
GenBank Accession No. AAY15202.1; Jun. 1, 2005.
GenBank Accession No. ABF60110.1; Feb. 11, 2007.
GenBank Accession No. NP_001003019.1; Nov. 20, 2011.
GenBank Accession No. NP_001082350.1; May 14, 2014.
GenBank Accession No. X15127.1; Feb. 4, 2011.
GenBank Accession No. NC_003210.1; May 16, 2014.
GenBank Accession No. NC_004500.1; Aug. 23, 2012.
GenBank Accession No. V01116.1; Feb. 4, 2011.
GenBank Accession No. X62843.1; Feb. 4, 2011.
Giannini et al. "Morphological precursors of hepatocellular carcinoma: a morphometrical analysis" Hepato-gastroenterology. Jun. 1987;34(3):95-7.
International Search Report for PCT Application No. PCT/US15/55604 dated Feb. 2, 2016.
Jones et al. "Characterization of Listeria monocytogenes pathogenesis in a strain expressing perfringolysin O in place of listeriolysin O" Infection and immunity. Dec. 1, 1994:62(12)5608-13.
Lauer et al. "Calendar R. Construction, characterization, and use of two Listeria monocytogenes site-specific phage integration vectors" Journal of bacteriology. Aug. 1, 2002;184(15):4177-86.
Nakanuma et al. "Anatomic and molecular pathology of intrahepatic cholangiocarcinoma" Journal of hepato-biliary-pancreatic surgery. Aug. 1, 2003;10(4):265-81.
O'Riordan et al. "Listeria intracellular growth and virulence require host-derived lipoic acid" Science. Oct. 17, 2003;302(5644):462-4.
Rechsteiner et al. "PEST sequences and regulation by proteolysis" Trends in biochemical sciences. Jul. 1, 1996;21(7):267-71.
Riegler JL"Preneoplastic conditions of the liver" In Seminars in gastrointestinal disease Apr. 1996 (vol. 7, No. 2, pp. 74-87).
Sewell et al. "Regression of HPV-positive tumors treated with a new Listeria monocytogenes vaccine" Archives of Otolaryngology—Head & Neck Surgery. Jan. 1, 2004;130(1):92-7.
Shimonishi et al. "Precancerous lesions of intrahepatic cholangiocarcinoma" Journal of Hepato-Biliary-Pancreatic Sciences. Dec. 1, 2000;7(6):542-50.
Skoble et al. "Three regions within ActA promote Arp2/3 complex-mediated actin nucleation and Listeria monocytogenes rnotility"s The Journal of cell biology. Aug. 7, 2000;150(3)527-38.
Su et al. "Relevance of hepatic preneopiasia for human hepatocarcinogenesis. Toxicologic pathology" Jan. 2003;31(1):126-33.
"Listeria monocytogenes (Murray et al.) Pirie (ATCC® BAA-679™)", ATCC, available at https://www.atcc.org/products/all/BAA-679.aspx?&p=1&rel=history#history.
GenBank [Internet]. Bethesda (MD): National Library of Medicine (US), National Center for Biotechnology Information; Accession No. AAD33253.1, E7 [Human papillomavirus type 16]; [cited Jun. 30, 2000]. Available from: https://www.ncbi.nlm.nih.gov/protein/4927721?sat=4&satkey=39322124.
GenBank [Internet]. Bethesda (MD): National Library of Medicine (US), National Center for Biotechnology Information; Accession No. P06788.2, Protein E7; [cited Oct. 1, 2014]. Available from: https://www.ncbi.nlm.nih.gov/protein/137792?sat=18&satkey=25463773.
GenBank [Internet]. Bethesda (MD): National Library of Medicine (US), National Center for Biotechnology Information; Accession No. AAD33252.1, E6 [Human papillomavirus type 16]; [cited Jun. 30, 2000]. Available from: https://www.ncbi.nlm.nih.gov/protein/4927720?sat=4&satkey=39322124.
GenBank [Internet]. Bethesda (MD): National Library of Medicine (US), National Center for Biotechnology Information; Accession No. AAM51854.1, transforming protein E6 [Human papillomavirus type 16]; [cited Jun. 18, 2002]. Available from: https://www.ncbi.nlm.nih.gov/protein/AAM51854.
GenBank [Internet]. Bethesda (MD): National Library of Medicine (US), National Center for Biotechnology Information; Accession No. AAM51853.1, transforming protein E6 [Human papillomavirus type 16]; [cited Jun. 18, 2002]. Available from: https://www.ncbi.nlm.nih.gov/protein/AAM51853.
GenBank [Internet]. Bethesda (MD): National Library of Medicine (US), National Center for Biotechnology Information; Accession No. AAB67615.1, mutant early transforming protein E6, partial [Human papillomavirus type 16]; [cited Aug. 23, 1997]. Available from: https://www.ncbi.nlm.nih.gov/protein/2342656?sat=13&satkey=9603921.
GenBank [Internet]. Bethesda (MD): National Library of Medicine (US), National Center for Biotechnology Information; Accession No. P06463.1, Protein E6; [cited Oct. 1, 2014]. Available from: https://www.ncbi.nlm.nih.gov/protein/137758?sat=18&satkey=25463390.
GenBank [Internet]. Bethesda (MD): National Library of Medicine (US), National Center for Biotechnology Information; Accession No. CAD30844.1, prostate specific antigen [*Homo sapiens*]; [cited Oct. 7, 2008]. Available from: https://www.ncbi.nlm.nih.gov/protein/CAD30844.
GenBank [Internet]. Bethesda (MD): National Library of Medicine (US), National Center for Biotechnology Information; Accession No. CAD54617.1, prostate specific antigen [*Homo sapiens*]; [cited Oct. 7, 2008]. Available from: https://www.ncbi.nlm.nih.gov/protein/CAD54617.
GenBank [Internet]. Bethesda (MD): National Library of Medicine (US), National Center for Biotechnology Information; Accession No. AAA58802.1, prostate-specific antigen [*Homo sapiens*]; [cited Jan. 5, 1995]. Available from: https://www.ncbi.nlm.nih.gov/protein/AAA58802.
GenBank [Internet]. Bethesda (MD): National Library of Medicine (US), National Center for Biotechnology Information; Accession No. NP_001639.1, prostate-specific antigen isoform 1 preproprotein [*Homo sapiens*]; [cited May 11, 2014]. Available from: https://www.ncbi.nlm.nih.gov/protein/4502173?sat=21&satkey=4516812.
GenBank [Internet]. Bethesda (MD): National Library of Medicine (US), National Center for Biotechnology Information; Accession No. AAK69652.1, stratum corneum chymotryptic enzyme [Mus musculus]; [cited Jul. 2, 2001]. Available from: https://www.ncbi.nlm.nih.gov/protein/AAK69652.
GenBank [Internet]. Bethesda (MD): National Library of Medicine (US), National Center for Biotechnology Information; Accession No. AAK69624.1, stratum corneum chymotryptic enzyme [*Homo sapiens*]; [cited Jul. 2, 2001]. Available from: https://www.ncbi.nlm.nih.gov/protein/AAK69624.
GenBank [Internet]. Bethesda (MD): National Library of Medicine (US), National Center for Biotechnology Information; Accession No. AAG33360.1, stratum corneum chymotryptic enzyme [*Homo sapiens*]; [cited Nov. 21, 2000]. Available from: https://www.ncbi.nlm.nih.gov/protein/AAG33360.
GenBank [Internet]. Bethesda (MD): National Library of Medicine (US), National Center for Biotechnology Information; Accession No. AAF01139.1, stratum corneum chymotryptic enzyme, partial [Mus musculus]; [cited Oct. 5, 1999]. Available from: https://www.ncbi.nlm.nih.gov/protein/6010462?sat=4&satkey=39333224.
GenBank [Internet]. Bethesda (MD): National Library of Medicine (US), National Center for Biotechnology Information; Accession No. AAC37551.1, stratum corneum chymotryptic enzyme [*Homo sapiens*]; [cited Aug. 26, 1994]. Available from: https://www.ncbi.nlm.nih.gov/protein/AAC37551.
GenBank [Internet]. Bethesda (MD): National Library of Medicine (US), National Center for Biotechnology Information; Accession No. P22561.1, Wilms tumor protein homolog; [cited Oct. 1, 2014]. Available from: https://www.ncbi.nlm.nih.gov/protein/139779?sat=18&satkey=25002011.
GenBank [Internet]. Bethesda (MD): National Library of Medicine (US), National Center for Biotechnology Information; Accession No. NP_659032.3, Wilms tumor protein homolog [Mus musculus]; [cited May 10, 2014]. Available from: https://www.ncbi.nlm.nih.gov/protein/153281234?sat=21&satkey=2754661.
GenBank [Internet]. Bethesda (MD): National Library of Medicine (US), National Center for Biotechnology Information; Accession

(56) References Cited

OTHER PUBLICATIONS

No. CAC39220.2, Wilms tumor 1 [*Homo sapiens*]; [cited May 7, 2008]. Available from: https://www.ncbi.nlm.nih.gov/protein/CAC39220.2

GenBank [Internet]. Bethesda (MD): National Library of Medicine (US), National Center for Biotechnology Information; Accession No. NM_198253.2, *Homo sapiens* telomerase reverse transcriptase (TERT), transcript variant 1, mRNA; [cited May 18, 2014]. Available from: https://www.ncbi.nlm.nih.gov/nuccore/109633030?sat=21&satkey=4678018.

GenBank [Internet]. Bethesda (MD): National Library of Medicine (US), National Center for Biotechnology Information; Accession No. M29142.1, Human myeloblastin mRNA, complete cds.; [cited Apr. 27, 1993]. Available from: https://www.ncbi.nlm.nih.gov/nuccore/M29142.

GenBank [Internet]. Bethesda (MD): National Library of Medicine (US), National Center for Biotechnology Information; Accession No. M75154.1, *H.sapiens* myeloblastin (MBN) mRNA, complete cds; [cited Jan. 7, 1995]. Available from: https://www.ncbi.nlm.nih.gov/nuccore/M75154.

GenBank [Internet]. Bethesda (MD): National Library of Medicine (US), National Center for Biotechnology Information; Accession No. M96839.1, Human proteinase 3 gene, exon 5 and cds (3' end); [cited Nov. 19, 2002]. Available from: https://www.ncbi.nlm.nih.gov/nuccore/M96839.1?report=genbank.

GenBank [Internet]. Bethesda (MD): National Library of Medicine (US), National Center for Biotechnology Information; Accession No. X55668.1, Human mRNA for proteinase 3; [cited Nov. 14, 2006]. Available from: https://www.ncbi.nlm.nih.gov/nuccore/X55668.

GenBank [Internet]. Bethesda (MD): National Library of Medicine (US), National Center for Biotechnology Information; Accession No. NM_000277.1, *Homo sapiens* phenylalanine hydroxylase (PAH), mRNA; [cited May 24, 2014]. Available from: https://www.ncbi.nlm.nih.gov/nuccore/4557818?sat=21&satkey=4516394.

GenBank [Internet]. Bethesda (MD): National Library of Medicine (US), National Center for Biotechnology Information; Accession No. M96628.1, Human gene sequence, 5' end; [cited Aug. 3, 1993]. Available from: https://www.ncbi.nlm.nih.gov/nuccore/M96628.

GenBank [Internet]. Bethesda (MD): National Library of Medicine (US), National Center for Biotechnology Information; Accession No. X56606.1, *H.sapiens* mRNA for Proteinase 3; [cited Nov. 14, 2006]. Available from: https://www.ncbi.nlm.nih.gov/nuccore/35189?sat=2&satkey=29441918.

GenBank [Internet]. Bethesda (MD): National Library of Medicine (US), National Center for Biotechnology Information; Accession No. NP_001913.2, L-dopachrome tautomerase isoform 1 precursor [*Homo sapiens*]; [cited Feb. 26, 2014]. Available from: https://www.ncbi.nlm.nih.gov/protein/6041667?sat=21&satkey=4521795.

GenBank [Internet]. Bethesda (MD): National Library of Medicine (US), National Center for Biotechnology Information; Accession No. AAP33051.1, tyrosinase-related protein-2 [Bos taurus]; [cited May 12, 2003]. Available from: https://www.ncbi.nlm.nih.gov/protein/AAP33051.

GenBank [Internet]. Bethesda (MD): National Library of Medicine (US), National Center for Biotechnology Information; Accession No. Q95119.2, Tyrosinase-related protein 2;; [cited Oct. 1, 2014]. Available from: https://www.ncbi.nlm.nih.gov/protein/109940040?sat=18&satkey=25420011.

GenBank [Internet]. Bethesda (MD): National Library of Medicine (US), National Center for Biotechnology Information; Accession No. NP_001888.2, chondroitin sulfate proteoglycan 4 precursor [*Homo sapiens*]; [cited Mar. 23, 2014]. Available from: https://www.ncbi.nlm.nih.gov/protein/47419930?sat=21&satkey=4683982.

GenBank [Internet]. Bethesda (MD): National Library of Medicine (US), National Center for Biotechnology Information; Accession No. AAI28111.1, CSPG4 protein, partial [*Homo sapiens*]; [cited Jul. 23, 2007]. Available from: https://www.ncbi.nlm.nih.gov/protein/AAI28111.

GenBank [Internet]. Bethesda (MD): National Library of Medicine (US), National Center for Biotechnology Information; Accession No. AAQ62842.1, melanoma chondroitin sulfate proteoglycan [*Homo sapiens*]; [cited Jul. 12, 2004]. Available from: https://www.ncbi.nlm.nih.gov/protein/AAQ62842.

GenBank [Internet]. Bethesda (MD): National Library of Medicine (US), National Center for Biotechnology Information; Accession No. AAF79020.1, testisin [*Homo sapiens*]; [cited Jun. 28, 2000]. Available from: https://www.ncbi.nlm.nih.gov/protein/AAF79020.

GenBank [Internet]. Bethesda (MD): National Library of Medicine (US), National Center for Biotechnology Information; Accession No. AAF79019.1, testisin [*Homo sapiens*]; [cited Jun. 28, 2000]. Available from: https://www.ncbi.nlm.nih.gov/protein/AAF79019.

GenBank [Internet]. Bethesda (MD): National Library of Medicine (US), National Center for Biotechnology Information; Accession No. AAG02255.1, testisin [Mus musculus]; [cited Mar. 28, 2001]. Available from: https://www.ncbi.nlm.nih.gov/protein/AAG02255.

GenBank [Internet]. Bethesda (MD): National Library of Medicine (US), National Center for Biotechnology Information; Accession No. AAK29360.1, testisin [Mus musculus]; [cited Apr. 4, 2001]. Available from: https://www.ncbi.nlm.nih.gov/protein/AAK29360.

GenBank [Internet]. Bethesda (MD): National Library of Medicine (US), National Center for Biotechnology Information; Accession No. AAD41588.1, testisin [*Homo sapiens*]; [cited Jul. 1, 1999]. Available from: https://www.ncbi.nlm.nih.gov/protein/AAD41588.

GenBank [Internet]. Bethesda (MD): National Library of Medicine (US), National Center for Biotechnology Information; Accession No. NP_659206.1, testisin isoform 3 preproprotein [*Homo sapiens*]; [cited Feb. 15, 2014] Available from: https://www.ncbi.nlm.nih.gov/protein/21614533?sat=21&satkey=4521874.

GenBank [Internet]. Bethesda (MD): National Library of Medicine (US), National Center for Biotechnology Information; Accession No. CAA05908.1, NY-ESO-1 protein [*Homo sapiens*]; [cited Oct. 7, 2008]. Available from: https://www.ncbi.nlm.nih.gov/protein/CAA05908.

GenBank [Internet]. Bethesda (MD): National Library of Medicine (US), National Center for Biotechnology Information; Accession No. P78358.1, Autoimmunogenic cancer/testis antigen NY-ESO-1; [cited Oct. 1, 2014]. Available from: https://www.ncbi.nlm.nih.gov/protein/6014739?sat=18&satkey=24841888.

GenBank [Internet]. Bethesda (MD): National Library of Medicine (US), National Center for Biotechnology Information; Accession No. AAB49693.1, autoimmunogenic cancer/testis antigen NY-ESO-1 [*Homo sapiens*]; [cited Dec. 22, 1999]. Available from: https://www.ncbi.nlm.nih.gov/protein/AAB49693.

GenBank [Internet]. Bethesda (MD): National Library of Medicine (US), National Center for Biotechnology Information; Accession No. NP_640343.1, cancer/testis antigen 1 [*Homo sapiens*]; [cited May 7, 2014]. Available from: https://www.ncbi.nlm.nih.gov/protein/21281685?sat=21&satkey=4519707.

GenBank [Internet]. Bethesda (MD): National Library of Medicine (US), National Center for Biotechnology Information; Accession No. AAH65183.1, PSCA protein [*Homo sapiens*]; [cited Jan. 6, 2006]. Available from: https://www.ncbi.nlm.nih.gov/protein/AAH65183.

GenBank [Internet]. Bethesda (MD): National Library of Medicine (US), National Center for Biotechnology Information; Accession No. NP_005663.2, prostate stem cell antigen preproprotein [*Homo sapiens*]; [cited May 3, 2014]. Available from: https://www.ncbi.nlm.nih.gov/protein/289547757?sat=21&satkey=4680634.

GenBank [Internet]. Bethesda (MD): National Library of Medicine (US), National Center for Biotechnology Information; Accession No. NP_082492.1, prostate stem cell antigen precursor [Mus musculus]; [cited Feb. 26, 2014]. Available from: https://www.ncbi.nlm.nih.gov/protein/21312316?sat=21&satkey=2597555.

GenBank [Internet]. Bethesda (MD): National Library of Medicine (US), National Center for Biotechnology Information; Accession No. O43653.1, Prostate stem cell antigen; [cited Oct. 1, 2014]. Available from: https://www.ncbi.nlm.nih.gov/protein/10720240?sat=18&satkey=25425460.

GenBank [Internet]. Bethesda (MD): National Library of Medicine (US), National Center for Biotechnology Information; Accession

(56) References Cited

OTHER PUBLICATIONS

No. CAB97347.1, prostate stem cell antigen [*Homo sapiens*]; [cited Oct. 7, 2008]. Available from: https://www.ncbi.nlm.nih.gov/protein/CAB97347.

GenBank [Internet]. Bethesda (MD): National Library of Medicine (US), National Center for Biotechnology Information; Accession No. NP_000631.1, interleukin-13 receptor subunit alpha-2 precursor [*Homo sapiens*]; [cited May 3, 2014]. Available from: https://www.ncbi.nlm.nih.gov/protein/10834992?sat=21&satkey=4520411.

GenBank [Internet]. Bethesda (MD): National Library of Medicine (US), National Center for Biotechnology Information; Accession No. NP_001551.1, interleukin-13 receptor subunit alpha-1 precursor [*Homo sapiens*]; [cited May 3, 2014]. Available from: https://www.ncbi.nlm.nih.gov/protein/4504647?sat=18&satkey=28634088.

GenBank [Internet]. Bethesda (MD): National Library of Medicine (US), National Center for Biotechnology Information; Accession No. NP_032382.1, interleukin-13 receptor subunit alpha-2 precursor [Mus musculus]; [cited Apr. 20, 2014]. Available from: https://www.ncbi.nlm.nih.gov/protein/6680405?sat=21&satkey=2754474.

GenBank [Internet]. Bethesda (MD): National Library of Medicine (US), National Center for Biotechnology Information; Accession No. NP_598751.3, interleukin-13 receptor subunit alpha-1 precursor [Mus musculus]; [cited May 11, 2014]. Available from: https://www.ncbi.nlm.nih.gov/protein/40254373?sat=21&satkey=2749918.

GenBank [Internet]. Bethesda (MD): National Library of Medicine (US), National Center for Biotechnology Information; Accession No. CAI13455.1, carbonic anhydrase IX [*Homo sapiens*]; [cited Jan. 13, 2009]. Available from: https://www.ncbi.nlm.nih.gov/protein/CAI13455.1?report=genpept.

GenBank [Internet]. Bethesda (MD): National Library of Medicine (US), National Center for Biotechnology Information; Accession No. CAI10985.1, carbonic anhydrase IX [*Homo sapiens*]; [cited Jan. 13, 2009]. Available from: https://www.ncbi.nlm.nih.gov/protein/CAI10985.1?report=genpept.

GenBank [Internet]. Bethesda (MD): National Library of Medicine (US), National Center for Biotechnology Information; Accession No. NP_001207.2, carbonic anhydrase 9 precursor [*Homo sapiens*]; [cited Jun. 11, 2014]. Available from: https://www.ncbi.nlm.nih.gov/protein/169636420?sat=21&satkey=4516815.

GenBank [Internet]. Bethesda (MD): National Library of Medicine (US), National Center for Biotechnology Information; Accession No. NP_001101426.1, carbonic anhydrase 9 precursor [Rattus norvegicus]; [cited Aug. 10, 2014]. Available from: https://www.ncbi.nlm.nih.gov/protein/157818645?sat=4&satkey=117916582.

GenBank [Internet]. Bethesda (MD): National Library of Medicine (US), National Center for Biotechnology Information; Accession No. AAA66186.1, carcinoembryonic antigen [*Homo sapiens*]; [cited May 11, 1995]. Available from: https://www.ncbi.nlm.nih.gov/protein/AAA66186.

GenBank [Internet]. Bethesda (MD): National Library of Medicine (US), National Center for Biotechnology Information; Accession No. CAA79884.1, carcinoembryonic antigen [*Homo sapiens*]; [cited Nov. 15]. Available from: https://vvww.ncbi.nlm.nih.gov/protein/CAA79884.

GenBank [Internet]. Bethesda (MD): National Library of Medicine (US), National Center for Biotechnology Information; Accession No. CAA66955.1, carcinoembryonic antigen [*Homo sapiens*]; [cited Oct. 7, 2008]. Available from: https://www.ncbi.nlm.nih.gov/protein/CAA66955.

GenBank [Internet]. Bethesda (MD): National Library of Medicine (US), National Center for Biotechnology Information; Accession No. AAA51966.1, carcinoembryonic antigen, partial [*Homo sapiens*]; [cited Oct. 16, 2000]. Available from: https://www.ncbi.nlm.nih.gov/protein/553221?sat=4&satkey=42721368.

GenBank [Internet]. Bethesda (MD): National Library of Medicine (US), National Center for Biotechnology Information; Accession No. AAD15250.1, carcinoembryonic antigen, partial [Mus musculus domesticus]; [cited Feb. 11, 1999]. Available from: https://www.ncbi.nlm.nih.gov/protein/AAD15250.

GenBank [Internet]. Bethesda (MD): National Library of Medicine (US), National Center for Biotechnology Information; Accession No. AAA51970.1, carcinoembryonic antigen [*Homo sapiens*]; [cited Nov 1, 1994]. Available from: https://www.ncbi.nlm.nih.gov/protein/AAA51970.

GenBank [Internet]. Bethesda (MD): National Library of Medicine (US), National Center for Biotechnology Information; Accession No. NP_786885.1, melanoma-associated antigen 2 [*Homo sapiens*]; [cited Aug. 9, 2014]. Available from: https://www.ncbi.nlm.nih.gov/protein/29029620?sat=21&satkey=1467770.

GenBank [Internet]. Bethesda (MD): National Library of Medicine (US), National Center for Biotechnology Information; Accession No. NP_786884.1, melanoma-associated antigen 2 [*Homo sapiens*]; [cited Aug. 9, 2014]. Available from: https://www.ncbi.nlm.nih.gov/protein/29029618?sat=21&satkey=1467684.

GenBank [Internet]. Bethesda (MD): National Library of Medicine (US), National Center for Biotechnology Information; Accession No. NP_005352.1, melanoma-associated antigen 2 [*Homo sapiens*]; [cited Aug. 9, 2014]. Available from: https://www.ncbi.nlm.nih.gov/protein/4885465?sat=21&satkey=1467818.

GenBank [Internet]. Bethesda (MD): National Library of Medicine (US), National Center for Biotechnology Information; Accession No. NP_004979.3, melanoma-associated antigen 1 [*Homo sapiens*]; [cited Aug. 9, 2014]. Available from: https://www.ncbi.nlm.nih.gov/protein/148276977?sat=18&satkey=28791425.

GenBank [Internet]. Bethesda (MD): National Library of Medicine (US), National Center for Biotechnology Information; Accession No. NP_005358.2, melanoma-associated antigen 12 [*Homo sapiens*].; [cited Aug. 9, 2014]. Available from: https://www.ncbi.nlm.nih.gov/protein/58530873?sat=21&satkey=1467768.

GenBank [Internet]. Bethesda (MD): National Library of Medicine (US), National Center for Biotechnology Information; Accession No. NP_005353.1, melanoma-associated antigen 3 [*Homo sapiens*]; [cited Aug. 9, 2014]. Available from: https://www.ncbi.nlm.nih.gov/protein/4885467?sat=21&satkey=1467639.

GenBank [Internet]. Bethesda (MD): National Library of Medicine (US), National Center for Biotechnology Information; Accession No. AAC51660.1, apoptosis inhibitor survivin [*Homo sapiens*]; [cited Sep. 2, 2004]. Available from: https://www.ncbi.nlm.nih.gov/protein/AAC51660.

GenBank [Internet]. Bethesda (MD): National Library of Medicine (US), National Center for Biotechnology Information; Accession No. AAY15202.1, survivin splice variant 2 alpha [*Homo sapiens*]; [cited Jun. 1, 2005]. Available from: https://www.ncbi.nlm.nih.gov/protein/AAY15202.

GenBank [Internet]. Bethesda (MD): National Library of Medicine (US), National Center for Biotechnology Information; Accession No. AAC60634.1, gp100 [*Homo sapiens*]; [cited Jan. 26, 1995]. Available from: https://www.ncbi.nlm.nih.gov/protein/AAC60634.

GenBank [Internet]. Bethesda (MD): National Library of Medicine (US), National Center for Biotechnology Information; Accession No. YP_655861.1, gp100 [Mycobacterium phage PMC]; [cited Apr. 17, 2009]. Available from: https://www.ncbi.nlm.nih.gov/protein/YP_655861.

GenBank [Internet]. Bethesda (MD): National Library of Medicine (US), National Center for Biotechnology Information; Accession No. AAB31176.1, melanoma antigen gp100 [human, breast cancer cell line MDA231, Peptide, 661 aa]; [cited Sep. 23, 1994]. Available from: https://www.ncbi.nlm.nih.gov/protein/AAB31176.

GenBank [Internet]. Bethesda (MD): National Library of Medicine (US), National Center for Biotechnology Information; Accession No. P13128.1, Thiol-activated cytolysin; [cited Oct. 1, 2014]. Available from: https://www.ncbi.nlm.nih.gov/protein/126336?sat=18&satkey=25334575.

GenBank [Internet]. Bethesda (MD): National Library of Medicine (US), National Center for Biotechnology Information; Accession No. AL591824.1, Listeria monocytogenes EGD-e, complete genome.; [cited Aug. 21, 2013]. Available from: https://www.ncbi.nlm.nih.gov/nuccore/30407125?sat=18&satkey=27969906.

GenBank [Internet]. Bethesda (MD): National Library of Medicine (US), National Center for Biotechnology Information; Accession

(56) References Cited

OTHER PUBLICATIONS

No. M24215.1, Human papillomavirus type 16, strain CC7T/VGH.; [cited Aug. 2, 1993]. Available from: https://www.ncbi.nlm.nih.gov/nuccore/M24215.
GenBank [Internet]. Bethesda (MD): National Library of Medicine (US), National Center for Biotechnology Information; Accession No. M14119.1, Human papillomavirus type 11 (HPV-11) complete genome; [cited Jun. 2, 1994]. Available from: https://www.ncbi.nlm.nih.gov/nuccore/M14119.
Kotoula, Vassiliki, et al. "Expression of human telomerase reverse transcriptase in regenerative and precancerous lesions of cirrhotic livers." Liver International 22.1 (2002): 57-69.
Röcken Christoph, and Stacy Carl-McGrath. "Pathology and pathogenesis of hepatocellular carcinoma." Digestive Diseases 19.4 (2001): 269-278.
GenBank [Internet]. Bethesda (MD): National Library of Medicine (US), National Center for Biotechnology Information; Accession No. CAC39220.2, Wilms tumor 1 [*Homo sapiens*]; [cited May 7, 2008]. Available from: https://www.ncbi.nlm.nih.gov/protein/CAC39220.2.
GenBank [Internet]. Bethesda (MD): National Library of Medicine (US), National Center for Biotechnology Information; Accession No. M96839.1, Human proteinase 3 gene, exon 5 and cds (3'end); [cited Nov. 19, 2002]. Available from: https://www.ncbi.nlm.nih.gov/nuccore/M96839.1?report=genbank.
GenBank [Internet]. Bethesda (MD): National Library of Medicine (US), National Center for Biotechnology Information; Accession No. X55668.1, Human mRNA for proteinase 3; [cited Nov. 14. 2006]. Available from: https://www.ncbi.nlm.nih.gov/nuccore/X55668.
GenBank [Internet]. Bethesda (MD): National Library of Medicine (US), National Center for Biotechnology Information; Accession No. NM_000277.1, *Homo sapiens* phenylalanine hydroxylase (PAH), mRNA; [cited May 24, 2014]. Available from: https://www.ncbi.nlm.nih.gov/nuccore/4557818?sat=21&satkey=4516394 .
GenBank [Internet]. Bethesda (MD): National Library of Medicine (US), National Center for Biotechnology Information; Accession No. M96628.1, Human gene sequence, 5' end; [cited Aug. 3 ,1993]. Available from: https://www.ncbi.nlm.nih.gov/nuccore/M96628.
GenBank [Internet]. Bethesda (MD): National Library of Medicine (US), National Center for Biotechnology Information; Accession No. NP_001913.2, L-dopachrome tautomerase isoform 1 precursor [*Homo sapiens* ]; [cited Feb. 26, 2014]. Available from: https://www.ncbi.nlm.nih.gov/protein/6041667?sat=21&satkey=4521795.
GenBank [Internet]. Bethesda (MD): National Library of Medicine (US), National Center for Biotechnology Information; Accession No. P78358.1, Autoimmunogenic cancer/testis antigen NY ESO-1; [cited Oct. 1, 2014]. Available from: https://www.ncbi.nlm.nih.gov/protein/6014739?sat=18&satkey=24841888.
GenBank [Internet]. Bethesda (MD): National Library of Medicine (US), National Center for Biotechnology Information; Accession No. 043653.1, Prostate stem cell antigen; [cited Oct. 1,2014]. Available from: https://www.ncbi.nlm.nih.gov/protein/10720240?sat=18&satkey=25425460.
GenBank [Internet]. Bethesda (MD): National Library of Medicine (US), National Center for Biotechnology Information; Accession No. CAA79884.1, carcinoembryonic antigen [*Homo sapiens*]; [cited Nov. 14]. Available from: https://www.ncbi.nlm.nih.gov/protein/CAA79884.
GenBank [Internet]. Bethesda (MD): National Library of Medicine (US), National Center for Biotechnology Information; Accession No. AAA51970.1, carcinoembryonic antigen [*Homo sapiens*]; [cited Nov. 1, 1994]. Available from: https://www.ncbi.nlm.nih.gov/protein/AAA51970.
Petit et al. "12 Month Survival and Safety Data from a Phase 2 Study in Recurrent Cervical Cancer" 2013 ASCO Annual Meeting, Abstract #5529, May 29, 2013 (May 29, 2013). Retrieved from the Internet: <http://content.stockpr.com/advaxis/media/e0e1d38f7024f8f0e534eb6fcb9acb82.pdf on Aug. 4, 2017 (Aug. 4, 2017).
Röcken, Christoph, and Stacy Carl-McGrath. "Pathology and pathogenesis of hepatocellular carcinoma." Digestive Diseases 19.4 (2001): 269-278.

\* cited by examiner

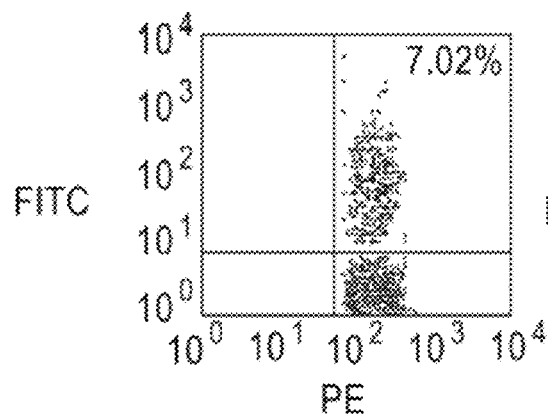
Figure 8G
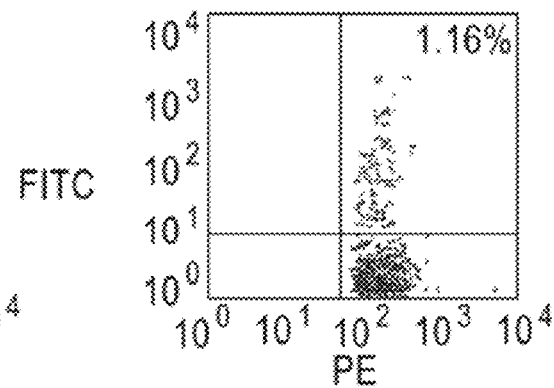
Figure 8H
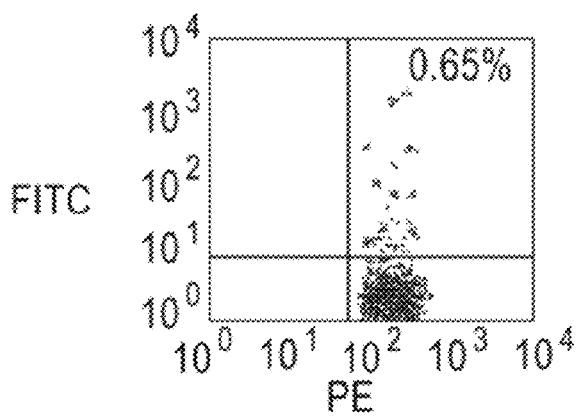
Figure 8I
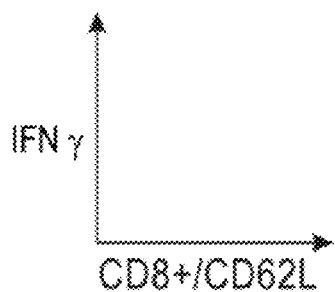

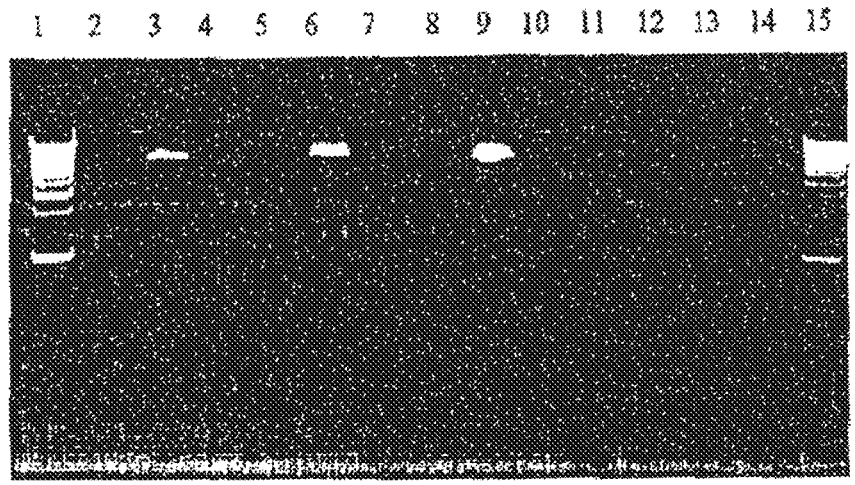

| Lane | Sample | Lane | Sample |
|---|---|---|---|
| 1 | 1Kb ladder | 9 | LB B, generation 5 |
| 2 | 100ng reference pGG55 | 10 | LB A, generation 9 |
| 3 | LB A, generation 5 | 11 | LB B, generation 14 |
| 4 | LB A, generation 9 | 12 | LB B, generation 19* |
| 5 | LB A, generation 14 | 13 | LB B, generation 24* |
| 6 | LB A, generation 19 | 14 | LB B, generation 29* |
| 7 | LB A, generation 24 | 15 | 1Kb ladder |
| 8 | LB A, generation 29 | | |

* Residual ethanol remaining in sample, therefore the majority of the sample did not load into the well, resulting in a less intense plasmid band

Figure 9A

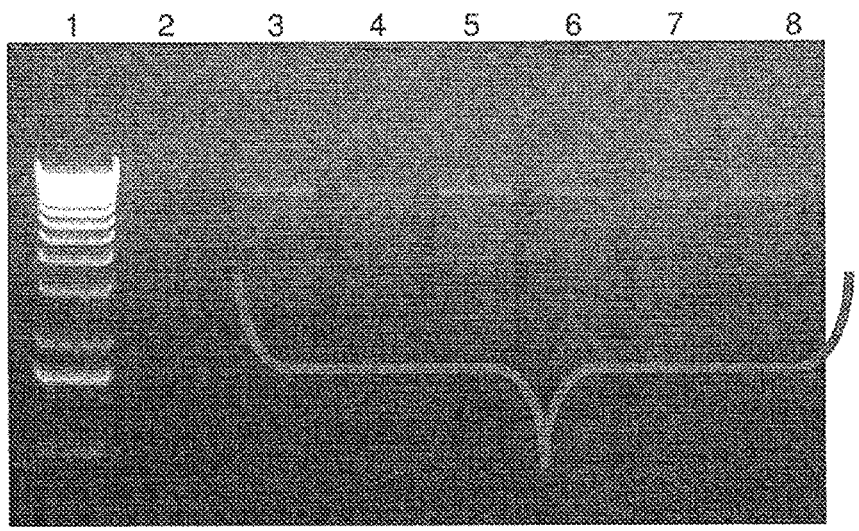

| Lane | Sample | | |
|---|---|---|---|
| 1 | 1Kb ladder | 5 | TB, generation 21 |
| 2 | 100ng reference pGG55 | 6 | TB, generation 28 |
| 3 | TB, generation 7 | 7 | TB, generation 35 |
| 4 | TB, generation 14 | 8 | TB, generation 42 |

Figure 9B

```
                                      ADV451 →
Lovaxin_C_pGG55        CCAAACCCTACAAAAACAAGTTTCATACAGCCTAGCTAAATTTAATGTTT
Reference_10403S_pfA   CCAAACCCTACAAAAACAAGTTTCATACAGCCTAGCTAAATTTAATGATT
                                                               ADV452 →
                       ************************************************ **

Lovaxin_C_pGG55        TTTCGATTAACGGGAAGCTTGGCTCTATTTGCGGTCAACTTTTAATCCTG
Reference_10403S_pfA   TTTCGATTAACGGGAAGCTTGGCTCTATTTGCGGTCAACTTTTAATCCTG
                       **************************************************

Lovaxin_C_pGG55        ACCTATGTGTATGGTAAAGAAACTCCTGATGGCATCAAGATTACACTGGA
Reference_10403S_pfA   ACCTATGTGTATGGTAAAGAAACTCCTGATGGCATCAAGATTACACTGGA
                       **************************************************

Lovaxin_C_pGG55        TAATTTAACAATGCAGGAGTTAGGATATATTCAAGTGGCATCGCACATAGCT
Reference_10403S_pfA   TAATTTAACAATGCAGGAGTTAGGATATATTCAAGTGGCATCGCACATAGCT
                       **************************************************

Lovaxin_C_pGG55        CAGCTGTTAGCAGAATTATTTCCAAATTAAAGCAAGAGAAGTTATCGTG
Reference_10403S_pfA   CAGCTGTTAGCAGAATTATTTCCAAATTAAAGCAAGAGAAGTTATCGTG
                       **************************************************

Lovaxin_C_pGG55        TATAAAAATTCATGCTTTTATGTACAAAATCGTGATTATCTCAAAGATA
Reference_10403S_pfA   TATAAAAATTCATGCTTTTATGTACAAAATCGTGATTATCTCAAAGATA
                       **************************************************

Lovaxin_C_pGG55        TGCCCCTAAATTAGATGAATGGTTTTATTTAGCATGTCCTGCTACTTGGG
Reference_10403S_pfA   TGCCCCTAAATTAGATGAATGGTTTTATTTAGCATGTCCTGCTACTTGGG
                                                              ← ADV453
                       **************************************************

Lovaxin_C_pGG55        GAAAATTAAATTAA (SEQ ID NO: 31)
Reference_10403S_pfA   GAAAATTAAATTAA (SEQ ID NO: 32)
                       **************
```

Figure 13

1. 5 ng of pGG55 D133V;
2. 1 ng of pGG55 D133V;
3. 0.2 ng of pGG55 D133V;
4. 5 ng of pGG55 wild-type;
5. 1 ng of pGG55 wild-type;
6. 0.2 ng of pGG55 wild-type;

1. 1 ng of pGG55 D133V
2. 1 ng of pGG55 wild-type
3. 100 pg of pGG55 wild-type ($10^{-1}$)
4. 10 pg of pGG55 wild-type ($10^{-2}$)
5. 1 pg of pGG55 wild-type ($10^{-3}$)
6. 100 fg of pGG55 wild-type ($10^{-4}$)
7. 10 fg of pGG55 wild-type ($10^{-5}$)
8. 1 fg of pGG55 wild-type ($10^{-6}$)

1. 5 ng of pGG55 D133V
2. 5 ng of pGG55 wild-type
3. 500 pg of pGG55 wild-type ($10^{-1}$)
4. 50 pg of pGG55 wild-type ($10^{-2}$)
5. 5 pg of pGG55 wild-type ($10^{-3}$)
6. 500 fg of pGG55 wild-type ($10^{-4}$)
7. 50 fg of pGG55 wild-type ($10^{-5}$)
8. 5 fg of pGG55 wild-type ($10^{-6}$)

1) 1 ng of pGG55 D133V only 2) 1 ng of pGG55 D133V only 3) 1 ng of pGG55 D133V + 1 ng of pGG55 wild-type prfA 4) 1 ng of pGG55 D133V + 100 pg of pGG55 wild-type prfA 6) 1 ng of pGG55 D133V + 1 pg of pGG55 wild-type prfA 7) 1 ng of pGG55 D133V + 100 fg of pGG55 wild-type prfA 8) 1 ng of pGG55 D133V + 10 fg of pGG55 wild-type prfA 9) 1 ng of pGG55 D133V + 1 fg of pGG55 wild-type prfA

| PT# | V1 Screening | V2 Vaccine 1 | V3 Vaccine 2 | V4 Pre-op | V5 2 weeks FU | V6 5 weeks FU | V7 3 months FU | V8 6 months FU | V9 12 months FU |
|---|---|---|---|---|---|---|---|---|---|
| 8001 | 1/2/2014 | 1/8/2014 | 1/22/2014 | 2/3/2014 | 2/18/2014 | 3/6/2014 | 5/8/2014 | 8/5/2014 | 1/8/2015 |
| 8002 | 4/17/2014 | 4/18/2014 | 5/2/2014 | 5/14/2014 | | | | | |
| 8003 | 5/23/2014 | 5/30/2014 | 6/13/2014 | 6/25/2014 | 7/8/2014 | 08/01/2014 | | | |
| 8004 | Missed | 7/24/2014 | 8/8/2014 | 8/26/2014 | Refused | 9/25/2014 | 11/19/2014 | 3/12/2015 | |
| 8005 | Missed | 7/24/2014 | 8/7/2014 | 8/25/2014 | 9/17/2014 | 10/3/2014 | 12/4/2014 | 03/19/2015 | |
| 8007 | 08/29/2014 | 9/9/2014 | 9/23/2014 | 10/2/2014 | 10/16/2014 | 11/6/2014 | | | |
| 8008 | 12/11/2014 | 12/12/2014 | 12/26/2014 | 1/6/2015 | Refused | 2/12/2015 | | | |
| 8009 | 1/22/2015 | 1/23/2015 | 2/6/2015 | 2/19/2015 | 03/03/2015 | 03/25/2015 | 04/16/2015 | Mid-July | |
| 8011 | | 03/03/2015 | | | Missed | 04/13/2015 | 05/15/2015 | Mid-August | |
| 8012 | | 3/19/2015 | | | 3/30/2015 | 04/21/2015 | 05/26/2015 | Mid-August | |
| 8013 | | 05/08/2015 | | | 05/18/2015 | 06/04/2015 | July | | |

Figure 28B

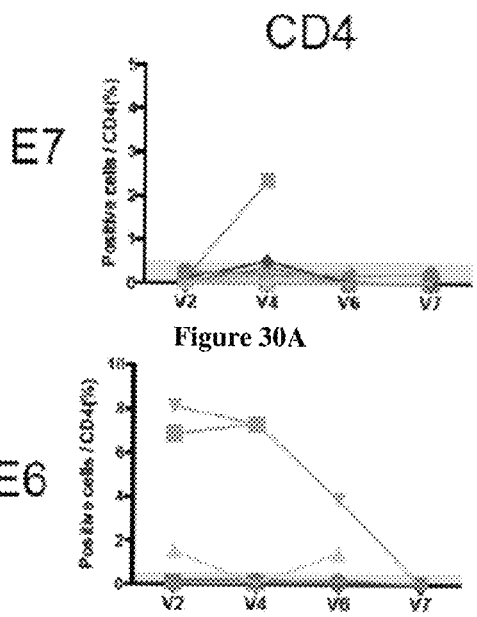
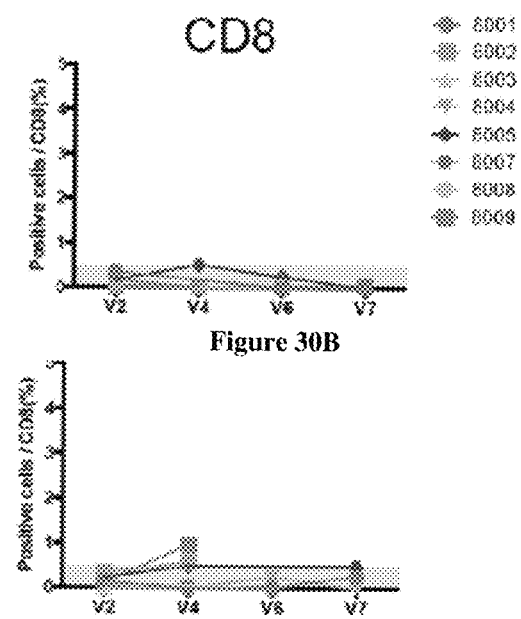
Figure 30A  Figure 30B
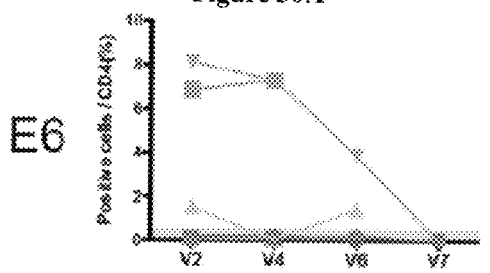
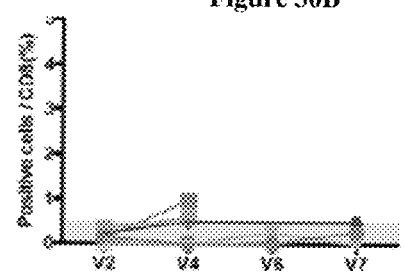
Figure 30C  Figure 30D
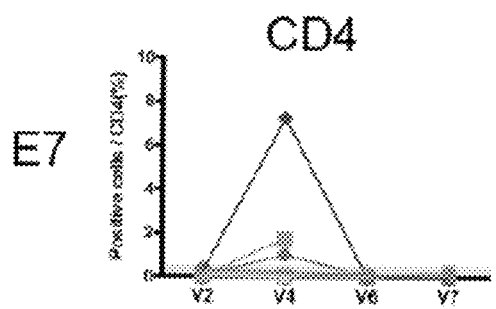
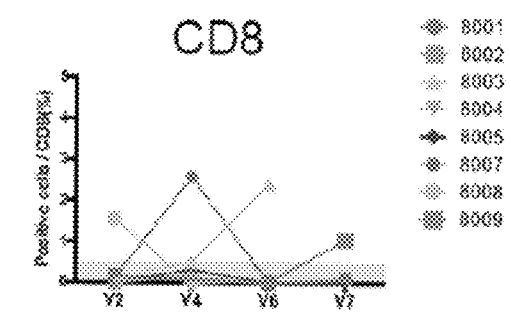
Figure 31A  Figure 31B
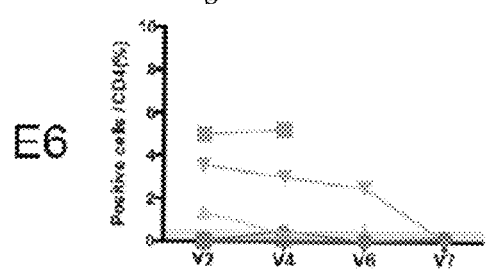
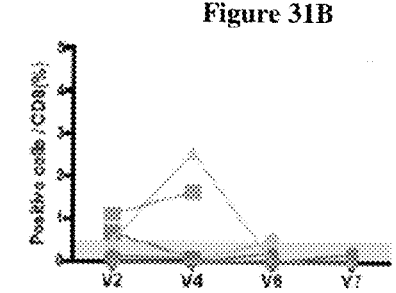
Figure 31C  Figure 31D

| E6 or E7 | PATIENT # | ExVivo ELI | IFNg ELI | IFNg ICS | TNFa ICS |
|---|---|---|---|---|---|
| | 8001 | + | + | | |
| | 8002 | + | + | + | + |
| | 8003 | + | + | | + |
| | 8004 | | + | | |
| | 8005 | | | | + |
| | 8007 | | | | + |
| | 8008 | | | | |
| | 8009 | | + | + | + |

Figure 32A

| E7 | PATIENT # | ExVivo ELI | IFNg ELI | IFNg ICS | TNFa ICS |
|---|---|---|---|---|---|
| | 8001 | 10.2014 | | | |
| | 8002 | + | + | + | + |
| | 8003 | | + | | + |
| | 8004 | (borderline) | + | | |
| | 8005 | | | | + |
| | 8007 | | | | + |
| | 8008 | | | | |
| | 8009 | | | | + |

Figure 32B

| E6 | PATIENT # | ExVivo ELI | IFNg ELI | IFNg ICS | TNFa ICS |
|---|---|---|---|---|---|
| | 8001 | | + | | |
| | 8002 | + | (borderline) | + | + |
| | 8003 | + | | | + |
| | 8004 | | | | |
| | 8005 | | | | |
| | 8007 | | | | |
| | 8008 | | | | (borderline) |
| | 8009 | | + | + | |

Figure 32C

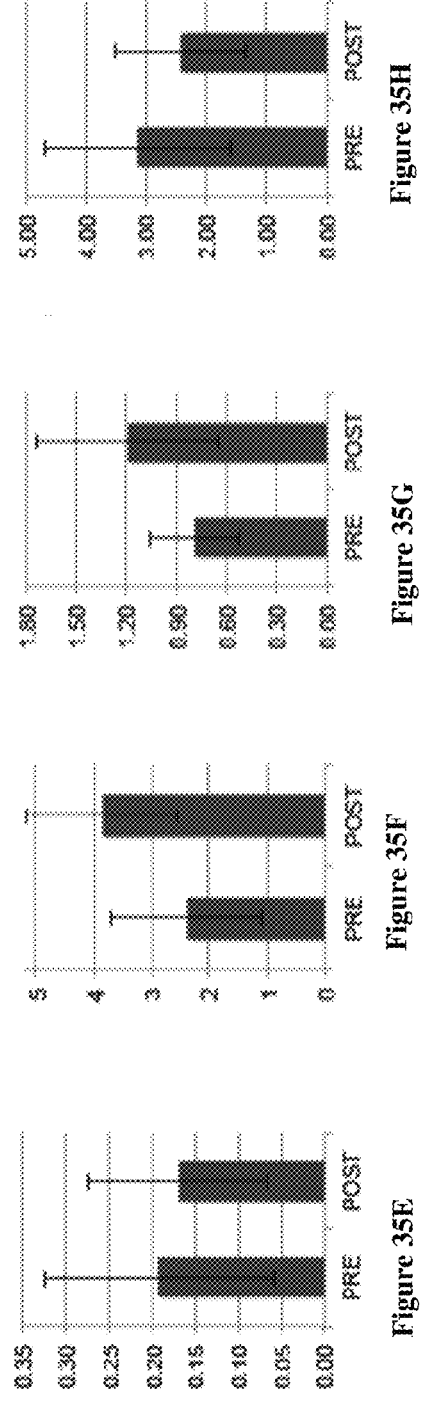
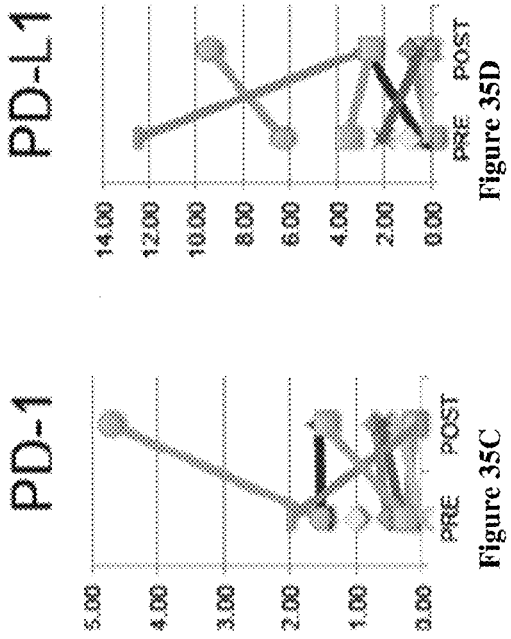
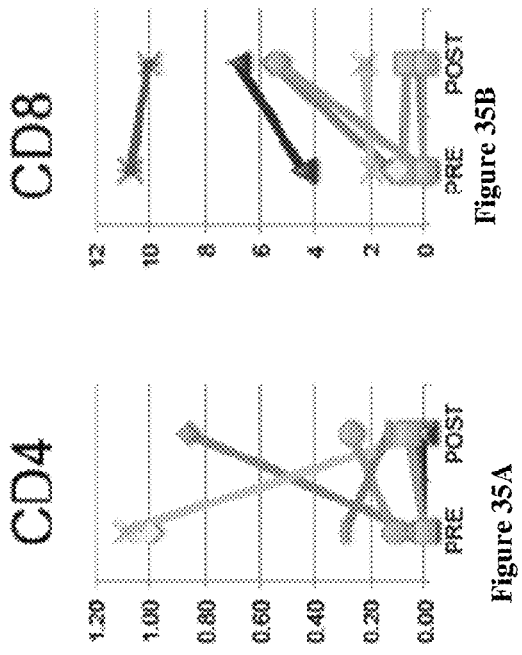
Figure 35A, Figure 35B, Figure 35C, Figure 35D, Figure 35E, Figure 35F, Figure 35G, Figure 35H

RECOMBINANT *LISTERIA* VACCINE STRAINS AND METHODS OF USING THE SAME IN CANCER IMMUNOTHERAPY

CROSS REFERENCE TO RELATED APPLICATIONS

This application claims the benefit of U.S. Provisional Application No. 62/063,828, filed on Oct. 14, 2014 and U.S. Provisional Application No. 62/065,973, filed on Oct. 20, 2014, both of which are incorporated by reference herein in their entirety.

FIELD OF INVENTION

The present invention provides methods of treating, protecting against, and inducing an immune response against a human papillomavirus-associated tumor or cancer, comprising the step of administering to a subject a recombinant *Listeria* expressing a human papillomavirus antigen.

BACKGROUND OF THE INVENTION

The prevalence of human papillomavirus (HPV)-associated oropharyngeal cancer (HPVOPC) is increasing in the USA (225% from 1988 to 2004). HPVOPC patients tend to be younger and have a favorable prognosis, with a 69% reduction in the risk of death compared with HPV-negative patients. However most HPVOPC patients present with advanced stage, and standard chemoradiation regimens can be associated with significant toxicity. Thus the patients who have a good prognosis are paradoxically at greater risk of therapy-related long-term poor quality-of-life outcomes. Immunotherapy has the potential to reduce toxicity through de-escalation of chemoradiation regimens, and potentially enhance long-term disease control.

The HR-HPV E6 and E7 proteins are consistently expressed in dysplasias and carcinomas, disrupting the cell cycle regulatory proteins p53 and pRb, respectively. The obligatory expression of E6 and E7 by both dysplastic and invasive malignant lesions, as well as the viral origin of these proteins, make them excellent targets for HPV therapeutic vaccines.

*Listeria monocytogenes* (Lm) is a food-borne gram-positive bacterium that can occasionally cause disease in humans, in particular elderly individuals, newborns, pregnant women and immunocompromised individuals. In addition to strongly activating innate immunity and inducing a cytokine response that enhances antigen-presenting cell (APC) function, Lm has the ability to replicate in the cytosol of APCs after escaping from the phagolysosome, mainly through the action of the listeriolysin O (LLO) protein. This unique intracellular life cycle allows antigens secreted by Lm to be processed and presented in the context of both MHC class I and II molecules, resulting in potent cytotoxic $CD8^+$ and Th1 $CD4^+$ T-cell-mediated immune responses.

The present invention addresses the issue of therapy-related long-term poor quality-of-life outcomes in patients having human papillomavirus (HPV)-associated oropharyngeal cancer by providing a composite therapy approach, which incorporates *Listeria monocytogenes* immunotherapy, thereby reducing toxicity through de-escalation of chemoradiation regimens, and potentially enhancing long-term disease control.

SUMMARY OF THE INVENTION

In one aspect, the present invention relates to a method of inducing an anti-tumor or an anti-cancer immune response in a human subject, the method comprising the step of administering to said subject a composition comprising a recombinant *Listeria* strain comprising a recombinant nucleic acid, said nucleic acid comprising a first open reading frame encoding a recombinant polypeptide comprising an N-terminal fragment of an LLO protein fused to heterologous antigen or fragment thereof, wherein said recombinant nucleic acid further comprises a second open reading frame encoding a mutant prfA gene or a metabolic enzyme, thereby inducing an immune response against a tumor or a cancer. In another embodiment, the immune response reduces the need for said subject to receive chemotherapy or radiation. In another embodiment, said immune response eliminates the need for said subject to receive chemotherapy or radiation. In another embodiment, said immune response reduces the severity of side effects associated with administration of a chemotherapy or radiation to said subject by allowing the patient to be treated with lower doses of chemotherapy or radiation.

In another aspect, said immune response enables a downstaging of disease such that a more conservative treatment option becomes available.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

FIG. 1B. Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

FIG. 5A. Induction of E7-specific IFN-gamma-secreting $CD8^+$ T cells in the spleens and the numbers penetrating the tumors, in mice administered TC-1 tumor cells and subsequently administered Lm-E7, Lm-LLO-E7, Lm-ActA-E7, or no vaccine (naive). FIG. 5B. Induction and penetration of E7 specific $CD8^+$ cells in the spleens and tumors of the mice described for (FIG. 5A).

FIG. 6A. representative data from 1 experiment. FIG. 6B. Average and SE of data from all 3 experiments.

FIG. 7A. Effect of passaging on bacterial load (virulence) of recombinant *Listeria* vaccine vectors. Top panel. Lm-Gag. Bottom panel. Lm-LLO-E7.

FIG. 7B. Effect of passaging on bacterial load of recombinant Lm-E7 in the spleen. Average CFU of live bacteria per milliliter of spleen homogenate from four mice is depicted.

FIG. 8A-I shows induction of antigen-specific $CD8^+$ T-cells for HIV-Gag and LLO after administration of passaged Lm-Gag versus unpassaged Lm-Gag. Mice were immunized with $10^3$ (FIG. 8A, FIG. 8B, FIG. 8E, FIG. 8F) or $10^5$ (FIG. 8C, FIG. 8D, FIG. 8G, FIG. 8H) CFU passaged *Listeria* vaccine vectors, and antigen-specific T-cells were analyzed. FIG. 8B, FIG. 8D, FIG. 8F, FIG. 8H: unpassaged *Listeria* vaccine vectors. FIG. 8A-D immune response to MHC class I HIV-Gag peptide. FIG. 8E-H: immune response to an LLO peptide. FIG. 8I: splenocytes from mice immunized with $10^5$ CFU passaged Lm-Gag stimulated with a control peptide from HPV E7.

FIG. 9A shows plasmid isolation throughout LB stability study. FIG. 9B shows plasmid isolation throughout TB stability study.

FIG. 12. Actual chromatograms showing the region of the D133V mutation (arrows). The mixture ratio is shown in parentheses.

FIG. 13. Representation of the location of the ADV451, 452 and 453 primers and the segment of the prfA gene amplified in the reaction.

FIG. 22A, Original image used for densitometry; FIG. 22B, Image was digitally enhanced to facilitate the visualization of the low density bands.

FIG. 28A-B. The phase II clinical trial design. FIG. 28A shows overall timeline of procedures and sample collection in the study (mo, months; PBMCs, peripheral blood mononuclear cells; TORS, transoral robotic surgery; wk, week.) FIG. 28B shows individual HPVOPC patients' procedure and sample collection schedule. The numbers in the first column represent individual patients. V1 and V2 samples were drawn before vaccination, V3 was drawn between the first and second vaccine administration, and V4 samples were drawn on the day of surgery. Samples V5-V9 were drawn from the patients indicated at the follow up visits at the indicated times post-surgery.

FIG. 30A-D. Summary of IFN-gamma intracellular cytokine staining (ICS) assay showing induction of E6- and E7-specific IFN-gamma-secreting CD4+ and CD8+ T cells following vaccination with ADXS-HPV. FIG. 30A shows induction of E7-specific IFN-gamma secreting CD4+ T cells. FIG. 30B shows induction of E7-specific IFN-gamma secreting CD8+ T cells. FIG. 30C shows induction of E6-specific IFN-gamma secreting CD4+ T cells. FIG. 30D shows induction of E6-specific IFN-gamma secreting CD8+ T cells.

FIG. 31A-D. Summary of TNF-alpha intracellular cytokine staining (ICS) assay showing induction of E6- and E7-specific TNF-alpha-secreting CD4+ and CD8+ T cells following vaccination with ADXS-HPV. FIG. 31A shows induction of E7-specific TNF-alpha secreting CD4+ T cells. FIG. 31B shows induction of E7-specific TNF-alpha secreting CD8+ T cells. FIG. 31C shows induction of E6-specific TNF-alpha secreting CD4+ T cells. FIG. 31D shows induction of E6-specific TNF-alpha secreting CD8+ T cells.

FIG. 32A-C. Summary HPV-specific responses. Numbers in the first column in each table represent individual patients. FIG. 32A shows patients that respond to E6 or E7 following ADXS-HPV vaccination. FIG. 32B shows patients that show E7 response. FIG. 32C shows patients that show E6 response. Responses were measured using the following tests: ExVivo ELI, IFNg ELI, IFN-gamma ELISPOT, IFNg ICS, IFN-gamma intracellular cytokine staining, TNFa ICS, TNF-alpha intracellular cytokine staining.

FIG. 33A shows the tumor milieu prior to vaccination. FIG. 33B shows the tumor prior to vaccination. FIG. 33C shows the dense intratumoral CD8 infiltration of tumor milieu after vaccination with ADXS-HPV. FIG. 33D shows the decreased tumor size following vaccination with ADXS-HPV. Red=CD8, Yellow=CD3, Magenta=PD-1, Green=PD-L1.

FIG. 34A, FIG. 34B, and FIG. 34C show three independent samples of tumor milieu prior to vaccination. FIG. 34D, FIG. 34E, and FIG. 34F show suppression of PD-L1 expression and infiltration of PD-1 expressing cells in the tumor milieu after vaccination with ADXS-HPV pre- and post-vaccination with ADXS-HPV. Red=CD8, Yellow=CD4, Magenta=PD-1, Green=PD-L1.

FIG. 35A-H. Preliminary quantitation of immunofluorescence results showing the levels of CD4, CD8, PD-1 and PD-L1 before and after vaccination with ADXS-HPV. FIG. 35A shows changes in CD4 levels observed in seven individual samples. FIG. 35B shows changes in CD8 levels observed in seven individual samples. FIG. 35C shows changes in PD-1 levels observed in seven individual samples. FIG. 35D shows changes in PD-L1 levels observed in seven individual samples. FIG. 35E shows the average change in CD4 for the cohort of samples in the FIG. 35A. FIG. 35F shows the average change in CD8 for the cohort of samples in the FIG. 35B. FIG. 35G shows the average change in PD-1 for the cohort of samples in the FIG. 35C. FIG. 35H shows the average change in PD-L1 for the cohort of samples in the FIG. 35D.

Figures 1A, 1B:
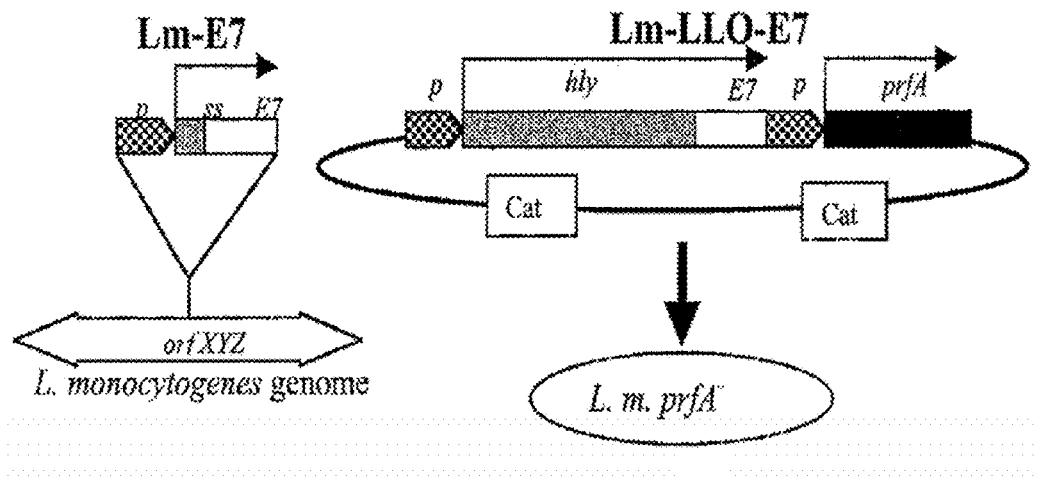
FIG. 1A-B. Lm-E7 and Lm-LLO-E7 use different expression systems to express and secrete E7. Lm-E7 was generated by introducing a gene cassette into the orfZ domain of the *L. monocytogenes* genome (FIG. 1A). The hly promoter drives expression of the hly signal sequence and the first five amino acids (AA) of LLO followed by HPV-16 E7.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The present invention provides methods of treating, protecting against, and inducing an immune response against a disease, comprising the step of administering to a subject a recombinant *Listeria* strain, expressing a fusion peptide comprising a listeriolysin O (LLO) fragment and a heterologous antigen expressed by said disease or a fragment thereof.

In one embodiment, the present invention provides a method of inducing an anti-tumor or an anti-cancer immune response in a human subject, the method comprising the step of administering to said subject a composition comprising a recombinant *Listeria* strain comprising a recombinant nucleic acid, said nucleic acid comprising a first open reading frame encoding a recombinant polypeptide comprising an N-terminal fragment of an LLO protein fused to a heterologous antigen or fragment thereof, wherein said recombinant nucleic acid further comprises a second open reading frame encoding a mutant prfA gene or a metabolic enzyme, thereby inducing an immune response against a tumor or a cancer. In another embodiment, said immune response reduces the need for said subject to receive chemotherapy or radiation. In another embodiment, said immune response eliminates the need for said subject to receive chemotherapy or radiation. In another embodiment, said immune response reduces the severity of side effects associated with administration of a chemotherapy or radiation to said subject by allowing the patient to be treated with lower doses of chemotherapy or radiation.

In one embodiment, the present invention provides a method of inducing an anti-tumor or an anti-cancer immune response in a human subject, the method comprising the step of administering to said subject a composition comprising a recombinant *Listeria* strain comprising a recombinant nucleic acid, said nucleic acid comprising a first open reading frame encoding a recombinant polypeptide comprising an N-terminal fragment of an LLO protein fused to a heterologous antigen or fragment thereof, wherein said recombinant nucleic acid further comprises a second open reading frame encoding a metabolic enzyme, wherein said immune response reduces the need for said subject to receive chemotherapeutic or radiation treatment, thereby inducing an immune response against a tumor or a cancer. In another embodiment, said *Listeria* comprises a mutation in the endogenous dal/dat and actA genes.

In one embodiment, the nucleic acid molecule disclosed herein comprises a first open reading frame encoding recombinant polypeptide comprising a heterologous antigen or fragment thereof. In another embodiment, the recombinant polypeptide further comprises an N-terminal LLO fused to the heterologous antigen. In another embodiment, the nucleic acid molecule disclosed herein further comprises a second open reading frame encoding a metabolic enzyme. In another embodiment, the metabolic enzyme complements an endogenous gene that is lacking in the chromosome of the recombinant *Listeria* strain. In another embodiment, the metabolic enzyme encoded by the second open reading frame is an alanine racemase enzyme (dal). In another embodiment, the metabolic enzyme encoded by the second open reading frame is a D-amino acid transferase enzyme (dat). In another embodiment, the *Listeria* strains disclosed herein comprise a mutation, a deletion or inactivation in the genomic dal, dat, or actA genes. In another embodiment, the *Listeria* strains disclosed herein comprise a mutation, a deletion or inactivation in the genomic dal, dat, and actA genes. In another embodiment, the *Listeria* lack the genomic dal, dat or actA genes. In another embodiment, the *Listeria* lack the genomic dal, dat and actA genes.

In another embodiment, administration of the *Listeria* disclosed herein or the *Listeria*-based immunotherapy disclosed herein is able to reduce the need of a subject having a tumor or a cancer to receive chemotherapeutic or radiation treatment. In another embodiment, administration of the *Listeria* disclosed herein or the *Listeria*-based immunotherapy disclosed herein is able to eliminate the need for a subject having a tumor or cancer to receive radiation or chemotherapy. In another embodiment, administration of the *Listeria* disclosed herein or the *Listeria*-based immunotherapy disclosed herein is able to reduce the severity of side effects associated with a radiation or chemotherapy treatment in a subject having a tumor or cancer. The present invention also provides methods for inducing an anti-disease cytotoxic T-cell (CTL) response in a human subject and treating disorders, and symptoms associated with said disease comprising administration of the recombinant *Listeria* strain. In one embodiment, disclosed herein is a recombinant *Listeria* strain, said recombinant *Listeria* strain comprising a recombinant nucleic acid, said nucleic acid comprising a first open reading frame encoding a recombinant polypeptide comprising a first an N-terminal fragment of an LLO protein fused to a heterologous antigen or fragment thereof, and wherein said recombinant nucleic acid further comprises a second open reading frame encoding a mutant prfA gene. In one embodiment, the mutant prfA gene is one that encodes a point mutation from amino acid D (which also known as "Asp," "Aspartate" or "Aspartic acid") to amino acid V (which is also known as "Val," or "Valine") at amino acid position 133. In one embodiment, a recombinant *Listeria* strain disclosed herein comprises a mutation or deletion in the endogenous prfA gene. In another embodiment, a chromosomal mutation or deletion in a prfA gene in a *Listeria* disclosed herein is complemented via a plasmid comprising a nucleic acid sequence encoding a mutant prfA gene encoding a mutant PrfA protein comprising a D133V amino acid substitution. In another embodiment, a mutant PrfA protein comprising a D133V amino acid substitution complements an endogenous prfA mutation in a *Listeria* disclosed herein.

In another embodiment, the recombinant *Listeria* is an attenuated *Listeria*. It will be appreciated that the terms "attenuation" or "attenuated" may encompass a bacterium, virus, parasite, infectious organism, prion, tumor cell, gene in the infectious organism, and the like, that is modified to reduce toxicity to a host. The host can be a human or animal, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. In one embodiment, attenuation can be assessed by measuring, e.g., an indicum or indicia of toxicity, the $LD_{50}$, the rate of clearance from an organ, or the competitive index (see, e.g., Auerbuch, et al. (2001) Infect. Immunity 69:5953-5957). Generally, an attenuation results in an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold. In another embodiment, attenuation results in an increase in the $LD_{50}$ and/or an increase in the rate of clearance by at least 25%. In another embodiment, attenuation results in an increase in the $LD_{50}$ and/or an increase in the rate of clearance by 3-5 fold. In other embodiments, attenuation results in an increase in the $LD_{50}$ and/or an increase in the rate of clearance by 5-10 fold, 11-20 fold, 21-30 fold, 31-40 fold, 41-50 fold, 51-100 fold, 101-500 fold, 501-1,000 fold, 1001-10,000 fold, or 10,001-100,000 fold.

It will be well appreciated by a skilled artisan that the term "Attenuated gene" may encompass a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, inversions, truncations, and frameshift mutations in regulatory regions of the gene, coding regions of the gene, non-coding regions of the gene, or any combination thereof.

In one embodiment, disclosed herein is a method for inducing an immune response against a tumor or a cancer in a human subject, the method comprising the step of administering to said subject a recombinant *Listeria* strain comprising a recombinant nucleic acid, said nucleic acid comprising a first open reading frame encoding a recombinant polypeptide comprising an N-terminal fragment of an LLO protein fused to a heterologous antigen or fragment thereof, is, wherein said recombinant nucleic acid further comprises a second open reading frame encoding a mutant PrfA protein, thereby inducing an immune response against a tumor or a cancer In one embodiment, the present invention provides a method of treating a cancer in a human subject, comprising the step of administering to the subject the recombinant *Listeria* strain disclosed herein. In another embodiment, the present invention provides a method of protecting a human subject against a cervical cancer, comprising the step of administering to the subject the recombinant *Listeria* strain disclosed herein. In another embodiment, the recombinant *Listeria* strain expresses the recombinant polypeptide. In another embodiment, the recombinant *Listeria* strain comprises a plasmid that encodes the recombinant polypeptide. In another embodiment, the method further comprises the step of boosting the human subject with a recombinant *Listeria* strain of the present invention. In another embodiment, the method further comprises the step of boosting the human subject with an immunogenic composition comprising a heterologous antigen or fragment thereof disclosed herein. In another embodiment, the method further comprises the step of boosting the human subject with an immunogenic composition that directs a cell of the subject to express the heterologous antigen. In another embodiment, the cell is a tumor cell. In another embodiment, the method further comprises the step of boosting the human subject with the vaccine of the present invention.

In one embodiment, the fragment thereof in the context of LLO proteins and ActA proteins disclosed herein refer to a peptide or polypeptide comprising an amino acid sequence of at least 5 contiguous amino acid residues of the LLO or ActA proteins. In another embodiment, the term refers to a peptide or polypeptide comprising an amino acid sequence of at least of at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, at least 250 contiguous amino acid residues of the amino acid sequence, at least 300 contiguous amino acid residues, at least 350 contiguous amino acid residues of, at least 400 contiguous amino acid residues, or at least 450 contiguous amino acid residues of an LLO or ActA protein or polypeptide.

In another embodiment, the fragment is a functional fragment that works as intended by the present invention (e.g. to elicit an immune response against a disease-associated antigen when in the form of an N-terminal LLO/heterologous antigen fusion protein or N-terminal ActA/heterologous antigen fusion protein). In another embodiment, the fragment is functional in a non-fused form. In another embodiment, the fragment is an immunogenic fragment.

The present invention, in certain embodiments, provides codon optimization of a nucleic acid heterologous to *Listeria*, or of a nucleic acid endogenous to *Listeria*. The optimal codons utilized by *L. monocytogenes* for each amino acid are shown US Patent Publication 2007/0207170, which is hereby incorporated by reference herein. A nucleic acid is codon-optimized if at least one codon in the nucleic acid is replaced with a codon that is more frequently used by *L. monocytogenes* for that amino acid than the codon in the original sequence.

The N-terminal LLO protein fragment and heterologous antigen are, in another embodiment, fused directly to one another. In another embodiment, the genes encoding the N-terminal LLO protein fragment and the heterologous antigen are fused directly to one another. In another embodiment, the N-terminal LLO protein fragment and the heterologous antigen are attached via a linker peptide. In another embodiment, the N-terminal LLO protein fragment and the heterologous antigen are attached via a heterologous peptide. In another embodiment, the N-terminal LLO protein fragment is N-terminal to the heterologous antigen. In another embodiment, the N-terminal LLO protein fragment is the N-terminal-most portion of the fusion protein.

As disclosed herein, recombinant *Listeria* strains expressing LLO-antigen fusions induce anti-tumor immunity (Example 1), elicit antigen-specific T cell proliferation (Example 2), generate antigen-specific and tumor-infiltrating T cells (Example 3).

In another embodiment, the present invention provides a method of treating a cervical cancer in a human subject, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby treating a cervical cancer in a human subject. In another embodiment, the recombinant *Listeria* strain expresses the recombinant polypeptide. In another embodiment, the recombinant *Listeria* strain comprises a plasmid that encodes the recombinant polypeptide.

In another embodiment, the present invention provides a method of protecting a human subject against a cervical cancer, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby protecting a human subject against a cervical cancer. In another embodiment, the recombinant *Listeria* strain expresses the recombinant polypeptide. In another embodiment, the recombinant *Listeria* strain comprises a plasmid that encodes the recombinant polypeptide.

In another embodiment, the present invention provides a method for inducing an immune response against a cervical cancer in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an immune response against a cervical cancer in a human subject. In another embodiment, the recombinant *Listeria* strain expresses the recombinant polypeptide. In another embodiment, the recombinant *Listeria* strain comprises a plasmid that encodes the recombinant polypeptide.

In another embodiment, the present invention provides a method of treating a cervical cancer in a human subject, comprising the step of administering to the subject a recombinant *Listeria* strain, the recombinant *Listeria* strain comprising a recombinant polypeptide comprising an N-terminal fragment of an ActA protein and heterologous antigen, whereby the recombinant *Listeria* strain induces an immune response against the heterologous antigen, thereby treating a cervical cancer in a human subject. In another embodiment, the recombinant *Listeria* strain expresses the recombinant polypeptide. In another embodiment, the recombinant *Listeria* strain comprises a plasmid that encodes the recombinant polypeptide.

In another embodiment, the present invention provides a method of protecting a human subject against a cervical cancer, comprising the step of administering to the subject a recombinant *Listeria* strain, the recombinant *Listeria* strain comprising a recombinant polypeptide comprising an N-terminal fragment of an ActA protein and a heterologous antigen, whereby the recombinant *Listeria* strain induces an immune response against the heterologous antigen, thereby protecting a human subject against a cervical cancer. In another embodiment, the recombinant *Listeria* strain expresses the recombinant polypeptide. In another embodiment, the recombinant *Listeria* strain comprises a plasmid that encodes the recombinant polypeptide.

In another embodiment, the present invention provides a method for inducing an immune response against a cervical cancer in a human subject, comprising the step of administering to the subject a recombinant *Listeria* strain, the recombinant *Listeria* strain comprising a recombinant polypeptide comprising an N-terminal fragment of an ActA protein and a heterologous antigen, thereby inducing an immune response against a cervical cancer in a human subject. In another embodiment, the recombinant *Listeria* strain expresses the recombinant polypeptide. In another embodiment, the recombinant *Listeria* strain comprises a plasmid that encodes the recombinant polypeptide.

The N-terminal ActA protein fragment and the heterologous antigen are, in another embodiment, fused directly to one another. In another embodiment, the genes encoding the N-terminal ActA protein fragment and heterologous antigen are fused directly to one another. In another embodiment, the N-terminal ActA protein fragment and heterologous antigen are attached via a linker peptide. In another embodiment, the N-terminal ActA protein fragment and heterologous antigen are attached via a heterologous peptide. In another embodiment, the N-terminal ActA protein fragment is N-terminal to the heterologous antigen. In another embodiment, the N-terminal ActA protein fragment is the N-terminal-most portion of the fusion protein.

In another embodiment, the present invention provides a method of inducing an immune response against a cervical cancer in a human subject, comprising the step of administering to the subject a recombinant Listeria strain, the recombinant Listeria strain comprising a recombinant polypeptide comprising a PEST amino acid sequence-containing peptide and a heterologous antigen, whereby the recombinant Listeria strain induces an immune response against the heterologous antigen, thereby treating a cervical cancer in a human subject. In another embodiment, the recombinant Listeria strain expresses the recombinant polypeptide. In another embodiment, the recombinant Listeria strain comprises a plasmid that encodes the recombinant polypeptide. In another embodiment, the method protects a human subject against a cervical. In another embodiment, the method treats a cervical cancer in said human subject.

The PEST amino acid amino acid sequence-containing peptide and heterologous antigen are, in another embodiment, fused directly to one another. In another embodiment, the genes encoding the PEST amino acid sequence-containing peptide and heterologous antigen are fused directly to one another. In another embodiment, the PEST amino acid sequence-containing peptide and heterologous antigen are attached via a linker peptide. In another embodiment, the PEST amino acid sequence-containing peptide and heterologous antigen are attached via a heterologous peptide. In another embodiment, the PEST amino acid sequence-containing peptide is N-terminal to the heterologous antigen. In another embodiment, the PEST amino acid sequence-containing peptide is the N-terminal-most portion of the fusion protein.

In another embodiment, the present invention provides a method for vaccinating a human subject against an HPV, comprising the step of administering to the subject the recombinant Listeria strain disclosed herein, wherein the Listeria expresses an HPV E7 antigen and wherein the Listeria expresses a mutant PrfA protein. In another embodiment, the mutant prfA gene encodes a D133V mutation in PrfA protein. In another embodiment, the mutant prfA gene is in a plasmid in said recombinant Listeria. In another embodiment, the recombinant Listeria strain expresses the recombinant polypeptide. In another embodiment, the recombinant Listeria strain comprises a plasmid that encodes the recombinant polypeptide.

In one embodiment, the term "operably linked" as used herein means that the transcriptional and translational regulatory nucleic acid, is positioned relative to any coding sequences in such a manner that transcription is initiated. Generally, this will mean that the promoter and transcriptional initiation or start sequences are positioned 5' to the coding region. In another embodiment the term "operably linked" as used herein means that several open reading frames are fused in a way that forms a single continuous reading frame resulting in expression of a protein that incorporates sequences of the original proteins arranged in succession.

In one embodiment, "fused" refers to operable linkage by covalent bonding. In one embodiment, the term includes recombinant fusion (of nucleic acid sequences or open reading frames thereof). In another embodiment, the term includes chemical conjugation.

In one embodiment, a fusion polypeptide disclosed herein is expressed and secreted by a recombinant Listeria disclosed herein.

In another embodiment, the subject is at risk for developing an HPV-mediated carcinogenesis (e.g. a cervical cancer). In another embodiment, the subject is HPV-positive. In another embodiment, the subject exhibits cervical intraepithelial neoplasia. In another embodiment, the subject exhibits a squamous intraepithelial lesion. In another embodiment, the subject exhibits a dysplasia in the cervix.

In one embodiment, the heterologous antigen is any tumor associated antigen known in the art and disclosed herein. In another embodiment, the heterologous antigen is an autoimmune antigen. In another embodiment, the heterologous antigen is an infectious disease antigen. In another embodiment, the heterologous antigen is an HPV-related antigen.

The HPV that is the target of methods of the present invention is, in another embodiment, an HPV 16. In another embodiment, the HPV is an HPV-18. In another embodiment, the HPV is selected from HPV-16 and HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type.

In another embodiment, the present invention provides a method of vaccinating a human subject against an antigen of interest, the method comprising the step of administering intravenously to the human subject a recombinant Listeria strain comprising or expressing the antigen of interest, wherein the first peptide is selected from (a) an N-terminal fragment of an LLO protein; (b) an ActA protein or N-terminal fragment thereof; and (c) a PEST amino acid sequence-containing peptide, thereby vaccinating a human subject against an antigen of interest.

In another embodiment, the present invention provides a method of vaccinating a human subject against an antigen of interest, the method comprising the step of administering intravenously to the human subject an immunogenic composition, comprising a fusion of a first peptide to the antigen of interest, wherein the first peptide is selected from (a) an N-terminal fragment of an LLO protein; (b) an ActA protein or N-terminal fragment thereof; and (c) a PEST amino acid sequence-containing peptide, thereby vaccinating a human subject against an antigen of interest.

In another embodiment, the present invention provides a method of vaccinating a human subject against an antigen of interest, the method comprising the step of administering intravenously to the human subject a recombinant Listeria strain comprising a recombinant polypeptide, the recombinant polypeptide comprising a first peptide fused to the antigen of interest, wherein the first peptide is selected from (a) an N-terminal fragment of an LLO protein; (b) an ActA protein or N-terminal fragment thereof; and (c) a PEST amino acid sequence-containing peptide, thereby vaccinating a human subject against an antigen of interest.

In another embodiment, the present invention provides a method of inducing a CTL response in a human subject against an antigen of interest, the method comprising the step of administering to the human subject a recombinant *Listeria* strain comprising or expressing the antigen of interest, thereby inducing a CTL response in a human subject against an antigen of interest. In another embodiment, the step of administering is intravenous administration.

As disclosed herein, recombinant *Listeria* strains expressing LLO-antigen fusions induce anti-tumor immunity (Example 1), elicit antigen-specific T cell proliferation (Example 2), generate antigen-specific and tumor-infiltrating T cells (Example 3). Thus, vaccines of the present invention are efficacious at inducing immune responses against E7 and E6.

In another embodiment, the present invention provides a method for inducing a regression of a cancer in a subject, comprising the step of administering to the subject the recombinant *Listeria* strain disclosed herein.

In another embodiment, the present invention provides a method for reducing an incidence of relapse of a cancer in a subject, comprising the step of administering to the subject the recombinant *Listeria* strain disclosed herein.

In another embodiment, the present invention provides a method for suppressing a formation of a tumor in a subject, comprising the step of administering to the subject the recombinant *Listeria* strain disclosed herein.

In another embodiment, the present invention provides a method for inducing a remission of a cancer in a subject, comprising the step of administering to the subject the recombinant *Listeria* strain disclosed herein.

In another embodiment, the present invention provides a method for impeding a growth of a tumor in a human subject, comprising the step of administering to the subject the recombinant *Listeria* strain disclosed herein.

In another embodiment, the present invention provides a method for reducing a size of a tumor in a subject, comprising the step of administering to the subject the recombinant *Listeria* strain disclosed herein.

In one embodiment, the disease is an infectious disease, an autoimmune disease, a respiratory disease, a pre-cancerous condition or a cancer.

It will be well appreciated by the skilled artisan that the term "pre-cancerous condition" may encompass dysplasias, preneoplastic nodules; macroregenerative nodules (MRN); low-grade dysplastic nodules (LG-DN); high-grade dysplastic nodules (HG-DN); biliary epithelial dysplasia; foci of altered hepatocytes (FAH); nodules of altered hepatocytes (NAH); chromosomal imbalances; aberrant activation of telomerase; re-expression of the catalytic subunit of telomerase; expression of endothelial cell markers such as CD31, CD34, and BNH9 (see, e.g., Terracciano and Tomillo (2003) Pathologica 95:71-82; Su and Bannasch (2003) Toxicol. Pathol. 31:126-133; Rocken and Carl-McGrath (2001) Dig. Dis. 19:269-278; Kotoula, et al. (2002) Liver 22:57-69; Frachon, et al. (2001) J. Hepatol. 34:850-857; Shimonishi, et al. (2000) J. Hepatobiliary Pancreat. Surg. 7:542-550; Nakanuma, et al. (2003) J. Hepatobiliary Pancreat. Surg. 10:265-281). Methods for diagnosing cancer and dysplasia are disclosed (see, e.g., Riegler (1996) Semin. Gastrointest. Dis. 7:74-87; Benvegnu, et al. (1992) Liver 12:80-83; Giannini, et al. (1987) Hepatogastroenterol. 34:95-97; Anthony (1976) Cancer Res. 36:2579-2583).

In one embodiment, an infectious disease is one caused by, but not limited to, any one of the following pathogens: BCG/Tuberculosis, Malaria, *Plasmodium falciparum, plasmodium malariae, plasmodium vivax*, Rotavirus, Cholera, Diphtheria-Tetanus, Pertussis, *Haemophilus influenzae*, Hepatitis B, Human papilloma virus, Influenza seasonal), Influenza A (H1N1) Pandemic, Measles and Rubella, Mumps, Meningococcus A+C, Oral Polio Vaccines, mono, bi and trivalent, Pneumococcal, Rabies, Tetanus Toxoid, Yellow Fever, *Bacillus anthracis* (anthrax), *Clostridium botulinum* toxin (botulism), *Yersinia pestis* (plague), Variola major (smallpox) and other related pox viruses, *Francisella tularensis* (tularemia), Viral hemorrhagic fevers, Arenaviruses (LCM, Junin virus, Machupo virus, Guanarito virus, Lassa Fever), Bunyaviruses (Hantaviruses, Rift Valley Fever), Flaviruses (Dengue), Filoviruses (Ebola, Marburg), *Burkholderia pseudomallei, Coxiella burnetii* (Q fever), *Brucella* species (brucellosis), *Burkholderia mallei* (glanders), *Chlamydia psittaci* (Psittacosis), Ricin toxin (from *Ricinus communis*), Epsilon toxin of *Clostridium perfringens, Staphylococcus* enterotoxin B, Typhus fever (*Rickettsia prowazekii*), other Rickettsias, Food- and Waterborne Pathogens, Bacteria (Diarrheagenic *E. coli*, Pathogenic Vibrios, *Shigella* species, *Salmonella* BCG/, *Campylobacter jejuni, Yersinia enterocolitica*), Viruses (Caliciviruses, Hepatitis A, West Nile Virus, LaCrosse, California encephalitis, VEE, EEE, WEE, Japanese Encephalitis Virus, Kyasanur Forest Virus, Nipah virus, hantaviruses, Tickborne hemorrhagic fever viruses, Chikungunya virus, Crimean-Congo Hemorrhagic fever virus, Tickborne encephalitis viruses, Hepatitis B virus, Hepatitis C virus, Herpes Simplex virus (HSV), Human immunodeficiency virus (HIV), Human papillomavirus (HPV)), Protozoa (*Cryptosporidium parvum, Cyclospora cayatanensis, Giardia lamblia, Entamoeba histolytica, Toxoplasma*), Fungi (Microsporidia), Yellow fever, Tuberculosis, including drug-resistant TB, Rabies, Prions, Severe acute respiratory syndrome associated coronavirus (SARS-CoV), *Coccidioides posadasii, Coccidioides immitis*, Bacterial vaginosis, *Chlamydia trachomatis*, Cytomegalovirus, Granuloma inguinale, *Hemophilus ducreyi, Neisseria gonorrhea, Treponema pallidum, Trichomonas vaginalis*, or any other infectious disease known in the art that is not listed herein.

In another embodiment, the infectious disease is a livestock infectious disease. In another embodiment, livestock diseases can be transmitted to man and are called "zoonotic diseases." In another embodiment, these diseases include, but are not limited to, Foot and mouth disease, West Nile Virus, rabies, canine parvovirus, feline leukemia virus, equine influenza virus, infectious bovine rhinotracheitis (IBR), pseudorabies, classical swine fever (CSF), IBR, caused by bovine herpesvirus type 1 (BHV-1) infection of cattle, and pseudorabies (Aujeszky's disease) in pigs, toxoplasmosis, anthrax, vesicular stomatitis virus, *rhodococcus equi*, Tularemia, Plague (*Yersinia pestis*), *trichomonas*.

In another embodiment, the disease disclosed herein is a respiratory or inflammatory disease. In another embodiment, the respiratory or inflammatory disease is chronic obstructive pulmonary disease (COPD). In another embodiment, the disease is asthma.

In one embodiment, live attenuated *Listeria* strains are capable of alleviating asthma symptoms without co-administration of other therapeutic agents, such as anti-inflammatory agents or bronchodilators. In another embodiment, the methods disclosed herein further comprise the step of co-administering to a subject the live attenuated *Listeria* strain and one or more therapeutic agents. In another embodiment, the therapeutic agent is an anti-asthmatic agent. In another embodiment, the agent is an anti-inflammatory agent, a non-steroidal anti-inflammatory agent, an antibiotic, an antichlolinerginc agent, a bronchodilator, a corticosteroid, a short-acting beta-agonist, a long-acting beta-agonist, combination inhalers, an antihistamine, or combinations thereof.

In one embodiment, the disease disclosed herein is a cancer or a tumor. In one embodiment, the tumor is cancerous. In another embodiment, the cancer is breast cancer. In another embodiment, the cancer is a cervical cancer. In another embodiment, the cancer is a Her2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, it is a glioblastoma multiforme. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non-small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. In another embodiment, the cancer is oropharyngeal cancer. In another embodiment, the cancer is lung cancer. In another embodiment, the cancer is anal cancer. In another embodiment, the cancer is colorectal cancer. In another embodiment, the cancer is esophageal cancer. The cervical tumor targeted by methods of the present invention is, in another embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art.

The cervical tumor targeted by methods of the present invention is, in another embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art.

In one embodiment, the antigen disclosed herein is a heterologous tumor antigen, which is also referred to herein as "tumor antigen" "antigenic polypeptide," or "foreign antigen." In another embodiment, the antigen is Human Papilloma Virus-E7 (HPV-E7) antigen, which in one embodiment, is from HPV16 (in one embodiment, GenBank Accession No. AAD33253) and in another embodiment, from HPV18 (in one embodiment, GenBank Accession No. P06788). In another embodiment, the antigenic polypeptide is HPV-E6, which in one embodiment, is from HPV16 (in one embodiment, GenBank Accession No. AAD33252, AAM51854, AAM51853, or AAB67615) and in another embodiment, from HPV18 (in one embodiment, GenBank Accession No. P06463). In another embodiment, the antigenic polypeptide is a Her/2-neu antigen. In another embodiment, the antigenic polypeptide is Prostate Specific Antigen (PSA) (in one embodiment, GenBank Accession No. CAD30844, CAD54617, AAA58802, or NP_001639). In another embodiment, the antigenic polypeptide is Stratum Corneum Chymotryptic Enzyme (SCCE) antigen (in one embodiment, GenBank Accession No. AAK69652, AAK69624, AAG33360, AAF01139, or AAC37551). In another embodiment, the antigenic polypeptide is Wilms tumor antigen 1, which in another embodiment is WT-1 Telomerase (GenBank Accession. No. P49952, P22561, NP_659032, CAC39220.2, or EAW68222.1). In another embodiment, the antigenic polypeptide is hTERT or Telomerase (GenBank Accession. No. NM003219 (variant 1), NM198255 (variant 2), NM 198253 (variant 3), or NM 198254 (variant 4). In another embodiment, the antigenic polypeptide is Proteinase 3 (in one embodiment, GenBank Accession No. M29142, M75154, M96839, X55668, NM 00277, M96628 or X56606). In another embodiment, the antigenic polypeptide is Tyrosinase Related Protein 2 (TRP2) (in one embodiment, GenBank Accession No. NP_001913, ABI73976, AAP33051, or Q95119). In another embodiment, the antigenic polypeptide is High Molecular Weight Melanoma Associated Antigen (HMW-MAA) (in one embodiment, GenBank Accession No. NP_001888, AAI28111, or AAQ62842). In another embodiment, the antigenic polypeptide is Testisin (in one embodiment, GenBank Accession No. AAF79020, AAF79019, AAG02255, AAK29360, AAD41588, or NP_659206). In another embodiment, the antigenic polypeptide is NY-ESO-1 antigen (in one embodiment, GenBank Accession No. CAA05908, P78358, AAB49693, or NP_640343). In another embodiment, the antigenic polypeptide is PSCA (in one embodiment, GenBank Accession No. AAH65183, NP_005663, NP_082492, 043653, or CAB97347). In another embodiment, the antigenic polypeptide is Interleukin (IL) 13 Receptor alpha (in one embodiment, GenBank Accession No. NP_000631, NP_001551, NP_032382, NP_598751, NP_001003075, or NP_999506). In another embodiment, the antigenic polypeptide is Carbonic anhydrase IX (CAIX) (in one embodiment, GenBank Accession No. CAI13455, CAI10985, EAW58359, NP_001207, NP_647466, or NP_001101426). In another embodiment, the antigenic polypeptide is carcinoembryonic antigen (CEA) (in one embodiment, GenBank Accession No. AAA66186, CAA79884, CAA66955, AAA51966, AAD15250, or AAA51970.). In another embodiment, the antigenic polypeptide is MAGE-A (in one embodiment, GenBank Accession No. NP_786885, NP_786884, NP_005352, NP_004979, NP_005358, or NP 005353). In another embodiment, the antigenic polypeptide is survivin (in one embodiment, GenBank Accession No. AAC51660, AAY15202, ABF60110, NP_001003019, or NP 001082350). In another embodiment, the antigenic polypeptide is GP100 (in one embodiment, GenBank Accession No. AAC60634, YP_655861, or AAB31176). In another embodiment, the antigenic polypeptide is any other antigenic polypeptide known in the art. In another embodiment, the antigenic peptide of the compositions and methods of the present invention comprise an immunogenic portion of the antigenic polypeptide.

In another embodiment, the antigen is HPV-E6. In another embodiment, the antigen is HPV16-E6. In another embodiment, the antigen is HPV18-E6. In another embodiment, the antigen is HPV-E7. In another embodiment, the antigen is HPV16-E7. In another embodiment, the antigen is HPV18-E7. In another embodiment, the antigen is telomerase (TERT). In another embodiment, the antigen is LMP-1. In another embodiment, the antigen is p53. In another embodiment, the antigen is mesothelin. In another embodiment, the antigen is EGFRVIII. In another embodiment, the antigen is carboxic anhydrase IX (CAIX). In another embodiment, the antigen is PSMA. In another embodiment, the antigen is HMW-MAA. In another embodiment, the antigen is HIV-1 Gag. In another embodiment, the antigen is Tyrosinase related protein 2. In another embodiment, the antigen is selected from HPV-E7, HPV-E6, Her-2, HIV-1 Gag, LMP-1, p53, PSMA, carcinoembryonic antigen (CEA), LMP-1, kallikrein-related peptidase 3 (KLK3), KLK9, Muc, Tyrosinase related protein 2, Muc1, FAP, IL-13R alpha 2, PSA (prostate-specific antigen), gp-100, heat-shock protein 70 (HSP-70), beta-HCG, EGFR-III, Granulocyte colony-stimulating factor (G-CSF), Angiogenin, Angiopoietin-1, Del-1, Fibroblast growth factors: acidic (aFGF) or basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), VEGFR, VEGFR2 (KDR/FLK-1) or a fragment thereof, FLK-1 or an epitope thereof, FLK-E1, FLK-E2, FLK-I1, endoglin or a fragment thereof, Neuropilin 1 (NRP-1), Angiopoietin 1 (Ang1), Tie2, Platelet-derived growth factor (PDGF), Platelet-derived growth factor receptor (PDGFR), Transforming growth factor-beta (TGF-β), endoglin, TGF-β receptors, monocyte chemotactic protein-1 (MCP-1), VE-cadherin, CD31, ephrin, ICAM-1, V-CAM-1, VAP-1, E-selectin, plasminogen activators, plasminogen activator inhibitor-1, Nitric oxide synthase (NOS), COX-2, AC133, or Id1/Id3, Angiopoietin 3, Angiopoietin 4, Angiopoietin 6, CD105, EDG, HHT1, ORW, ORW1 or a TGFbeta co-receptor, or a combination thereof. In another embodiment, the antigen is a chimeric Her2/neu antigen as disclosed in US Patent Application Publication No. 2011/0142791, which is incorporated by reference herein in its entirety. The use of fragments of antigens disclosed herein is also encompassed by the present invention.

In another embodiment, the heterologous tumor antigen disclosed herein is a tumor-associated antigen, which in one embodiment, is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, a MART1 antigen associated with melanoma, or the PSA antigen associated with prostate cancer. In another embodiment, the antigen for the compositions and methods disclosed herein are melanoma-associated antigens, which in one embodiment are TRP-2, MAGE-1, MAGE-3, gp-100, tyrosinase, HSP-70, beta-HCG, or a combination thereof. It is to be understood that a skilled artisan would be able to use any heterologous antigen not mentioned herein but known in the art for use in the methods and compositions disclosed herein. It is also to be understood that the present invention provides, but is not limited by, an attenuated Listeria comprising a nucleic acid that encodes at least one of the antigens disclosed herein. The present invention encompasses nucleic acids encoding mutants, muteins, splice variants, fragments, truncated variants, soluble variants, extracellular domains, intracellular domains, mature sequences, and the like, of the disclosed antigens. Disclosed are nucleic acids encoding epitopes, oligo- and polypeptides of these antigens. Also disclosed are codon optimized embodiments that are, optimized for expression in Listeria. The cited references, GenBank Acc. Nos., and the nucleic acids, peptides, and polypeptides disclosed herein, are all incorporated herein by reference in their entirety. In another embodiment, the selected nucleic acid sequence can encode a full length or a truncated gene, a fusion or tagged gene, and can be a cDNA, a genomic DNA, or a DNA fragment, preferably, a cDNA. It can be mutated or otherwise modified as desired. These modifications include codon optimizations to optimize codon usage in the selected host cell or bacteria, i.e. Listeria. The selected sequence can also encode a secreted, cytoplasmic, nuclear, membrane bound or cell surface polypeptide.

In one embodiment, vascular endothelial growth factor (VEGF) is an important signaling protein involved in both vasculogenesis (the formation of the embryonic circulatory system) and angiogenesis (the growth of blood vessels from pre-existing vasculature). In one embodiment, VEGF activity is restricted mainly to cells of the vascular endothelium, although it does have effects on a limited number of other cell types (e.g. stimulation monocyte/macrophage migration). In vitro, VEGF has been shown to stimulate endothelial cell mitogenesis and cell migration. VEGF also enhances microvascular permeability and is sometimes referred to as vascular permeability factor.

In one embodiment, all of the members of the VEGF family stimulate cellular responses by binding to tyrosine kinase receptors (the VEGFRs) on the cell surface, causing them to dimerize and become activated through transphosphorylation. The VEGF receptors have an extracellular portion consisting of 7 immunoglobulin-like domains, a single transmembrane spanning region and an intracellular portion containing a split tyrosine-kinase domain.

In one embodiment, VEGF-A is a VEGFR-2 (KDR/Flk-1) ligand as well as a VEGFR-1 (Flt-1) ligand. In one embodiment, VEGFR-mediates almost all of the known cellular responses to VEGF. The function of VEGFR-1 is less well defined, although it is thought to modulate VEGFR-2 signaling, in one embodiment, via sequestration of VEGF from VEGFR-2 binding, which in one embodiment, is particularly important during vasculogenesis in the embryo. In one embodiment, VEGF-C and VEGF-D are ligands of the VEGFR-3 receptor, which in one embodiment, mediates lymphangiogenesis.

In one embodiment, the compositions of the present invention comprise a VEGF receptor or a fragment thereof, which in one embodiment, is a VEGFR-2 and, in another embodiment, a VEGFR-1, and, in another embodiment, VEGFR-3.

In one embodiment, vascular Endothelial Growth Factor Receptor 2 (VEGFR2) is highly expressed on activated endothelial cells (ECs) and participates in the formation of new blood vessels. In one embodiment, VEGFR2 binds all 5 isoforms of VEGF. In one embodiment, signaling of VEGF through VEGFR2 on ECs induces proliferation, migration, and eventual differentiation. In one embodiment, the mouse homologue of VEGFR2 is the fetal liver kinase gene-1 (Flk-1), which is a strong therapeutic target, and has important roles in tumor growth, invasion, and metastasis. In one embodiment, VEGFR2 is also referred to as kinase insert domain receptor (a type III receptor tyrosine kinase) (KDR), cluster of differentiation 309 (CD309), FLK1, Ly73, Krd-1, VEGFR, VEGFR-2, or 6130401C07.

In other embodiments, the antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus* influenza outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Muc1, or pSA.

In other embodiments, the antigen is associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis *nodosa*, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

In another embodiment, an HPV E6 antigen is utilized instead of or in addition to an E7 antigen in a method of the present invention for treating, protecting against, or inducing an immune response against a cervical cancer.

In another embodiment, an ActA protein fragment is utilized instead of or in addition to an LLO fragment in a method of the present invention for treating, protecting against, or inducing an immune response against a cervical cancer.

In another embodiment, a PEST amino acid sequence-containing protein fragment is utilized instead of or in addition to an LLO fragment in a method of the present invention for treating, protecting against, or inducing an immune response against a cervical cancer.

In another embodiment, the present invention provides an immunogenic composition comprising a recombinant *Listeria* of the present invention. In another embodiment, the immunogenic composition of methods and compositions of the present invention comprises a recombinant vaccine vector of the present invention. In another embodiment, the immunogenic composition comprises a plasmid of the present invention. In another embodiment, the immunogenic composition comprises an adjuvant. In one embodiment, a vector of the present invention may be administered as part of a vaccine composition.

In another embodiment, a vaccine of the present invention is delivered with an adjuvant. In one embodiment, the adjuvant favors a predominantly Th1-mediated immune response. In another embodiment, the adjuvant favors a Th1-type immune response. In another embodiment, the adjuvant favors a Th1-mediated immune response. In another embodiment, the adjuvant favors a cell-mediated immune response over an antibody-mediated response. In another embodiment, the adjuvant is any other type of adjuvant known in the art. In another embodiment, the immunogenic composition induces the formation of a T cell immune response against the target protein.

In another embodiment, the present invention provides a method for inducing an anti-E7 cytotoxic T cell (CTL) response in a human subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an anti-E7 CTL response in a human subject. In another embodiment, the recombinant *Listeria* strain comprises a plasmid that encodes the recombinant polypeptide. In another embodiment, the method further comprises the step of boosting the subject with a recombinant *Listeria* strain of the present invention. In another embodiment, the method further comprises the step of boosting the subject with an immunogenic composition comprising an E7 antigen. In another embodiment, the method further comprises the step of boosting the subject with an immunogenic composition that directs a cell of the subject to express an E7 antigen. In another embodiment, the CTL response is capable of therapeutic efficacy against an HPV-mediated disease, disorder, or symptom. In another embodiment, the CTL response is capable of prophylactic efficacy against an HPV-mediated disease, disorder, or symptom.

In another embodiment, the present invention provides a method of treating or ameliorating an HPV-mediated disease, disorder, or symptom in a subject, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby treating or ameliorating an HPV-mediated disease, disorder, or symptom in a subject. In another embodiment, the subject is a human subject. In another embodiment, the subject is a non-human mammal. In another embodiment, the subject is any other type of subject known in the art.

The HPV causing the disease, disorder, or symptom is, in another embodiment, an HPV 16. In another embodiment, the HPV is an HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type.

In another embodiment, the HPV-mediated disease, disorder, or symptom is genital warts. In another embodiment, the HPV-mediated disease, disorder, or symptom is non-genital warts. In another embodiment, the HPV-mediated disease, disorder, or symptom is a respiratory papilloma. In another embodiment, the HPV-mediated disease, disorder, or symptom is any other HPV-mediated disease, disorder, or symptom known in the art.

In another embodiment, an HPV E6 antigen is utilized instead of or in addition to an E7 antigen in a method of the present invention for treating or ameliorating an HPV-mediated disease, disorder, or symptom.

In another embodiment, an ActA protein fragment is utilized instead of or in addition to an LLO fragment in a method of the present invention for treating or ameliorating an HPV-mediated disease, disorder, or symptom.

In another embodiment, a PEST amino acid sequence-containing protein fragment is utilized instead of or in addition to an LLO fragment in a method of the present invention for treating or ameliorating an HPV-mediated disease, disorder, or symptom.

In another embodiment, an HPV E6 antigen is utilized instead of or in addition to an E7 antigen in a method of the present invention for treating or ameliorating an HPV-mediated disease, disorder, or symptom.

The antigen of methods and compositions of the present invention is, in another embodiment, an HPV E7 protein. In another embodiment, the antigen is an HPV E6 protein. In another embodiment, the antigen is any other HPV protein known in the art.

"E7 antigen" refers, in another embodiment, to an E7 protein. In another embodiment, the term refers to an E7 fragment. In another embodiment, the term refers to an E7 peptide. In another embodiment, the term refers to any other type of E7 antigen known in the art.

The E7 protein of methods and compositions of the present invention is, in another embodiment, an HPV 16 E7 protein. In another embodiment, the E7 protein is an HPV-18 E7 protein. In another embodiment, the E7 protein is an HPV-31 E7 protein. In another embodiment, the E7 protein is an HPV-35 E7 protein. In another embodiment, the E7 protein is an HPV-39 E7 protein. In another embodiment, the E7 protein is an HPV-45 E7 protein. In another embodiment, the E7 protein is an HPV-51 E7 protein. In another embodiment, the E7 protein is an HPV-52 E7 protein. In another embodiment, the E7 protein is an HPV-58 E7 protein. In another embodiment, the E7 protein is an E7 protein of a high-risk HPV type. In another embodiment, the E7 protein is an E7 protein of a mucosal HPV type.

"E6 antigen" refers, in another embodiment, to an E6 protein. In another embodiment, the term refers to an E6 fragment. In another embodiment, the term refers to an E6 peptide. In another embodiment, the term refers to any other type of E6 antigen known in the art.

The E6 protein of methods and compositions of the present invention is, in another embodiment, an HPV 16 E6 protein. In another embodiment, the E6 protein is an HPV-18 E6 protein. In another embodiment, the E6 protein is an HPV-31 E6 protein. In another embodiment, the E6 protein is an HPV-35 E6 protein. In another embodiment, the E6 protein is an HPV-39 E6 protein. In another embodiment, the E6 protein is an HPV-45 E6 protein. In another embodiment, the E6 protein is an HPV-51 E6 protein. In another embodiment, the E6 protein is an HPV-52 E6 protein. In another embodiment, the E6 protein is an HPV-58 E6 protein. In another embodiment, the E6 protein is an E6 protein of a high-risk HPV type. In another embodiment, the E6 protein is an E6 protein of a mucosal HPV type.

The immune response induced by methods and compositions of the present invention is, in another embodiment, a T cell response. In another embodiment, the immune response comprises a T cell response. In another embodiment, the response is a $CD8^+$ T cell response. In another embodiment, the response comprises a $CD8^+$ T cell response.

In one embodiment, compositions of the present invention induce a strong innate stimulation of interferon-gamma, which in one embodiment, has anti-angiogenic properties. In one embodiment, a *Listeria* of the present invention induces a strong innate stimulation of interferon-gamma, which in one embodiment, has anti-angiogenic properties (Dominiecki et al., Cancer Immunol Immunother. 2005 May; 54(5):477-88. Epub 2004 Oct. 6, incorporated herein by reference in its entirety; Beatty and Paterson, J Immunol. 2001 Feb. 15; 166(4):2276-82, incorporated herein by reference in its entirety). In another embodiment, methods of the present invention increase a level of interferon-gamma producing cells. In one embodiment, anti-angiogenic properties of *Listeria* are mediated by $CD4^+$ T cells (Beatty and Paterson, 2001). In another embodiment, anti-angiogenic properties of *Listeria* are mediated by $CD8^+$ T cells. In another embodiment, IFN-gamma secretion as a result of *Listeria* vaccination is mediated by NK cells, NKT cells, Th1 $CD4^+$ T cells, TC1 $CD8^+$ T cells, or a combination thereof.

In another embodiment, compositions of the present invention induce production of one or more anti-angiogenic proteins or factors. In one embodiment, the anti-angiogenic protein is IFN-gamma. In another embodiment, the anti-angiogenic protein is pigment epithelium-derived factor (PEDF); angiostatin; endostatin; fms-like tyrosine kinase (sFlt)-1; or soluble endoglin (sEng). In one embodiment, a *Listeria* of the present invention is involved in the release of anti-angiogenic factors, and, therefore, in one embodiment, has a therapeutic role in addition to its role as a vector for introducing an antigen to a subject. Each *Listeria* strain and type thereof represents a separate embodiment of the present invention.

In another embodiment the immune response induced by methods and compositions of the present invention is suppression of programmed cell death receptor-1 ligand 1 (PD-L1) expression in the target tumor cells. In another embodiment, the immune response comprises increased level of programmed cell death receptor-1 (PD-1) expressing immune cells within tumor. In another embodiment, the immune response comprises increase in ratio of the level of PD-1 expression to PD-L1 expression. In another embodiment, the immune response comprises inhibition of tumor PD-L1-mediated immunosuppression.

In another embodiment, the administration of compositions of the present invention induces robust systemic antigen-specific immunity. In another embodiment, the administration of compositions of the present invention induces epitope spreading. In another embodiment, the administration of compositions of the present invention induces broad-based response to self-derived tumor antigens. In another embodiment the immune response induced by methods and compositions of the present invention comprises improvement of the overall balance of suppressor and effector immune cells in the tumor microenvironment (TME). In another embodiment the immune response induced by methods and compositions of the present invention comprises improvement in the systemic balance of suppressor and effector immunocytes.

In one embodiment, compositions and methods of use thereof as disclosed herein generate effector T cells that are able to infiltrate the tumor, destroy tumor cells and eradicate the disease. In another embodiment, methods of use of this invention increase infiltration by T effector cells. In another embodiment, T effector cells comprise CD8+ T cells. In another embodiment, T effector cells comprise CD4+ T cells.

In one embodiment, tumor infiltrating lymphocytes (TILs) are associated with better prognosis in several tumors, such as colon, ovarian and melanoma. In colon cancer, tumors without signs of micrometastasis have an increased infiltration of immune cells and a Th1 expression profile, which correlate with an improved survival of patients. Moreover, the infiltration of the tumor by T cells has been associated with success of immunotherapeutic approaches in both pre-clinical and human trials. In one embodiment, the infiltration of lymphocytes into the tumor site is dependent on the up-regulation of adhesion molecules in the endothelial cells of the tumor vasculature, generally by proinflammatory cytokines, such as IFN-γ, TNF-α and IL-1. Several adhesion molecules have been implicated in the process of lymphocyte infiltration into tumors, including intercellular adhesion molecule 1 (ICAM-1), vascular endothelial cell adhesion molecule 1 (V-CAM-1), vascular adhesion protein 1 (VAP-1) and E-selectin. However, these cell-adhesion molecules are commonly down-regulated in the tumor vasculature. Thus, in one embodiment, cancer vaccines as disclosed herein increase TILs, up-regulate adhesion molecules (in one embodiment, ICAM-1, V-CAM-1, VAP-1, E-selectin, or a combination thereof), up-regulate pro-inflammatory cytokines (in one embodiment, IFN-γ, TNF-α, IL-1, or a combination thereof), or a combination thereof.

The N-terminal LLO protein fragment of methods and compositions of the present invention comprises, in another embodiment, SEQ ID No: 2. In another embodiment, the fragment comprises an LLO signal peptide. In another embodiment, the fragment comprises SEQ ID No: 2. In another embodiment, the fragment consists approximately of SEQ ID No: 2. In another embodiment, the fragment consists essentially of SEQ ID No: 2. In another embodiment, the fragment corresponds to SEQ ID No: 2. In another embodiment, the fragment is homologous to SEQ ID No: 2. In another embodiment, the fragment is homologous to a fragment of SEQ ID No: 2. The ALLO used in some of the Examples was 416 AA long (exclusive of the signal sequence), as 88 residues from the amino terminus which is inclusive of the activation domain containing cysteine 484 were truncated. It will be clear to those skilled in the art that any ALLO without the activation domain, and in particular without cysteine 484, are suitable for methods and compositions of the present invention. In another embodiment, fusion of an E7 or E6 antigen to any ALLO, including the PEST amino acid AA sequence, SEQ ID NO: 1, enhances cell mediated and anti-tumor immunity of the antigen.

The LLO protein utilized to construct vaccines of the present invention has, in another embodiment, the sequence:
MKKIMLVFITLILVSLPIAQQTEAKDASAFNKEN-SISSMAPPASPPASPKTPIEKKHA DEIDKYIQGL-DYNKNNVLVYHGDAVTNVPPRKGYKDGNEYIV-VEKKKKSINQNNAD IQVVNAISSLTYPGALVKANSELVENQPDVLPVKRD-SLTLSIDLPGMTNQDNKIVVKN ATKSNVN-NAVNTLVERWNEKYAQAYPNVSAKIDYDDEMAY-SESQLIAKFGTAFKA VNNSLNVNFGAISEGKMQEEVISFKQIYYNVNVNEP-TRPSRFFGKAVTKEQLQALGV NAENPPAYISS-VAYGRQVYLKLSTNSHSTKVKAAFDAAVSGKSVS-GDVELTNIIKNSS FKAVIYGGSAKDEVQIIDGNLG DLRDILKKGATFNRETPGVPIAYTTNFLKDNELAVI KNNSEYIETTSKAYTDGKINIDHSGGYVAQF-NISWDEVNYDPEGNEIVQHKNWSENN KSKLAHFTS-SIYLPGNARNINVYAKECTGLAWEWWRTVIDDRNL-PLVKNRNISIWGT TLYPKYSNKVDNPIE (GenBank Accession No. P13128; SEQ ID NO: 3; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full length active LLO protein is 504 residues long. In another embodiment, the above LLO fragment is used as the source of the LLO fragment incorporated in a vaccine of the present invention.

In another embodiment, the N-terminal fragment of an LLO protein utilized in compositions and methods of the present invention has the sequence:

```
                                         (SEQ ID NO: 2)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINIDHSGGYVAQFNISWDEVNYD.
```

In another embodiment, the LLO fragment corresponds to about AA 20-442 of an LLO protein utilized herein.

In another embodiment, the LLO fragment has the sequence:

```
                                         (SEQ ID NO: 4)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTD.
```

In another embodiment, "truncated LLO" or "ALLO" refers to a fragment of LLO that comprises the PEST amino acid domain. In another embodiment, the terms refer to an LLO fragment that comprises a PEST sequence.

In another embodiment, the terms refer to an LLO fragment that does not contain the activation domain at the amino terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly.

In another embodiment, the LLO fragment is any other LLO fragment known in the art.

In another embodiment, the recombinant *Listeria* strain is administered to the human subject at a dose of $1 \times 10^9$-$3.31 \times 10^{10}$ CFU. In another embodiment, the dose is $5$-$500 \times 10^8$ CFU. In another embodiment, the dose is $7$-$500 \times 10^8$ CFU. In another embodiment, the dose is $10$-$500 \times 10^8$ CFU. In another embodiment, the dose is $20$-$500 \times 10^8$ CFU. In another embodiment, the dose is $30$-$500 \times 10^8$ CFU. In another embodiment, the dose is $50$-$500 \times 10^8$ CFU. In another embodiment, the dose is $70$-$500 \times 10^8$ CFU. In another embodiment, the dose is $100$-$500 \times 10^8$ CFU. In another embodiment, the dose is $150$-$500 \times 10^8$ CFU. In another embodiment, the dose is $5$-$300 \times 10^8$ CFU. In another embodiment, the dose is $5$-$200 \times 10^8$ CFU. In another embodiment, the dose is $5$-$150 \times 10^8$ CFU. In another embodiment, the dose is $5$-$100 \times 10^8$ CFU. In another embodiment, the dose is $5$-$70 \times 10^8$ CFU. In another embodiment, the dose is $5$-$50 \times 10^8$ CFU. In another embodiment, the dose is $5$-$30 \times 10^8$ CFU. In another embodiment, the dose is $5$-$20 \times 10^8$ CFU. In another embodiment, the dose is $1$-$30 \times 10^9$ CFU. In another embodiment, the dose is $1$-$20 \times 10^9$ CFU. In another embodiment, the dose is $2$-$30 \times 10^9$ CFU. In another embodiment, the dose is $1$-$10 \times 10^9$ CFU. In another embodiment, the dose is $2$-$10 \times 10^9$ CFU. In another embodiment, the dose is $3$-$10 \times 10^9$ CFU. In another embodiment, the dose is $2$-$7 \times 10^9$ CFU. In another embodiment, the dose is $2$-$5 \times 10^9$ CFU. In another embodiment, the dose is $3$-$5 \times 10^9$ CFU.

In another embodiment, the dose is $1 \times 10^9$ organisms. In another embodiment, the dose is $1.5 \times 10^9$ organisms. In another embodiment, the dose is $2 \times 10^9$ organisms. In another embodiment, the dose is $3 \times 10^9$ organisms. In another embodiment, the dose is $4 \times 10^9$ organisms. In another embodiment, the dose is $5 \times 10^9$ organisms. In another embodiment, the dose is $6 \times 10^9$ organisms. In another embodiment, the dose is $7 \times 10^9$ organisms. In another embodiment, the dose is $8 \times 10^9$ organisms. In another embodiment, the dose is $10 \times 10^9$ organisms. In another embodiment, the dose is $1.5 \times 10^{10}$ organisms. In another embodiment, the dose is $2 \times 10^{10}$ organisms. In another embodiment, the dose is $2.5 \times 10^{10}$ organisms. In another embodiment, the dose is $3 \times 10^{10}$ organisms. In another embodiment, the dose is $3.3 \times 10^{10}$ organisms. In another embodiment, the dose is $4 \times 10^{10}$ organisms. In another embodiment, the dose is $5 \times 10^{10}$ organisms.

In another embodiment, the recombinant polypeptide of methods of the present invention is expressed by the recombinant *Listeria* strain. In another embodiment, the expression is mediated by a nucleotide molecule carried by the recombinant *Listeria* strain.

In another embodiment, the recombinant *Listeria* strain expresses the recombinant polypeptide by means of a plasmid that encodes the recombinant polypeptide. In another embodiment, the plasmid comprises a gene encoding a bacterial transcription factor. In another embodiment, the plasmid encodes a *Listeria* transcription factor. In another embodiment, the transcription factor is PrfA. In another embodiment, the PrfA is a mutant PrfA. In another embodiment, the PrfA contains a D133V amino acid mutation. In another embodiment, the transcription factor is any other transcription factor known in the art.

In another embodiment, the plasmid comprises a gene encoding a metabolic enzyme. In another embodiment, the metabolic enzyme is a bacterial metabolic enzyme. In another embodiment, the metabolic enzyme is a *Listerial* metabolic enzyme. In another embodiment, the metabolic enzyme is an amino acid metabolism enzyme. In another embodiment, the amino acid metabolism gene is involved in a cell wall synthesis pathway. In another embodiment, the metabolic enzyme is the product of a D-amino acid aminotransferase gene (dat). In another embodiment, the metabolic enzyme is the product of an alanine racemase gene (dal). In another embodiment, the metabolic enzyme is any other metabolic enzyme known in the art.

In another embodiment, a method of present invention further comprises the step of boosting the human subject with a recombinant *Listeria* strain of the present invention. In another embodiment, the recombinant *Listeria* strain used in the booster inoculation is the same as the strain used in the initial "priming" inoculation. In another embodiment, the booster strain is different from the priming strain. In another embodiment, the same doses are used in the priming and boosting inoculations. In another embodiment, a larger dose is used in the booster. In another embodiment, a smaller dose is used in the booster.

In another embodiment, a method of present invention further comprises the step of inoculating the human subject with an immunogenic composition comprising the E7 antigen. In another embodiment, the immunogenic composition comprises a recombinant E7 protein or fragment thereof. In another embodiment, the immunogenic composition comprises a nucleotide molecule expressing a recombinant E7 protein or fragment thereof. In another embodiment, the non-*Listerial* inoculation is administered after the *Listerial* inoculation. In another embodiment, the non-*Listerial* inoculation is administered before the *Listerial* inoculation.

"Boosting" refers, in another embodiment, to administration of an additional vaccine dose to a subject. In another embodiment of methods of the present invention, 2 boosts (or a total of 3 inoculations) are administered. In another embodiment, 3 boosts are administered. In another embodiment, 4 boosts are administered. In another embodiment, 5 boosts are administered. In another embodiment, 6 boosts are administered. In another embodiment, more than 6 boosts are administered.

The recombinant *Listeria* strain of methods and compositions of the present invention is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art.

The present invention provides a number of *Listerial* species and strains for making or engineering an attenuated *Listeria* of the present invention. In one embodiment, the *Listeria* strain is *L. monocytogenes* 10403S wild type (see Bishop and Hinrichs (1987) J. Immunol. 139: 2005-2009; Lauer, et al. (2002) J. Bact. 184: 4177-4186.). In another embodiment, the *Listeria* strain is *L. monocytogenes* DP-L4056 (phage cured) (see Lauer, et al. (2002) J. Bact. 184: 4177-4186). In another embodiment, the *Listeria* strain is *L. monocytogenes* DP-L4027, which is phage cured and deleted in the hly gene (see Lauer, et al. (2002) J. Bact. 184: 4177-4186; Jones and Portnoy (1994) Infect. Immunity 65: 5608-5613.). In another embodiment, the *Listeria* strain is *L. monocytogenes* DP-L4029, which is phage cured, deleted in ActA (see Lauer, et al. (2002) J. Bact. 184: 4177-4186; Skoble, et al. (2000) J. Cell Biol. 150: 527-538). In another embodiment, the *Listeria* strain is *L. monocytogenes* DP-L4042 (delta PEST) (see Brockstedt, et al. (2004) Proc. Natl. Acad. Sci. USA 101: 13832-13837; supporting information). In another embodiment, the *Listeria* strain is *L. monocytogenes* DP-L4097 (LLO-S44A) (see Brockstedt, et al. (2004) Proc. Natl. Acad. Sci. USA 101: 13832-13837; supporting information). In another embodiment, the *Listeria* strain is *L. monocytogenes* DP-L4364 (delta lplA; lipoate protein ligase) (see Brockstedt, et al. (2004) Proc. Natl. Acad. Sci. USA 101: 13832-13837; supporting information). In another embodiment, the *Listeria* strain is *L. monocytogenes* DP-L4405 (delta inlA) (see Brockstedt, et al. (2004) Proc. Natl. Acad. Sci. USA 101: 13832-13837; supporting information). In another embodiment, the *Listeria* strain is *L. monocytogenes* DP-L4406 (delta inlB) (see Brockstedt, et al. (2004) Proc. Natl. Acad. Sci. USA 101: 13832-13837; supporting information). In another embodiment, the *Listeria* strain is *L. monocytogenes* CS-L0001 (delta ActA-delta inlB) (see Brockstedt, et al. (2004) Proc. Natl. Acad. Sci. USA 101: 13832-13837; supporting information). In another embodiment, the *Listeria* strain is *L. monocytogenes* CS-L0002 (delta ActA-delta lplA) (see Brockstedt, et al. (2004) Proc. Natl. Acad. Sci. USA 101: 13832-13837; supporting information). In another embodiment, the *Listeria* strain is *L. monocytogenes* CS-L0003 (L461T-delta lplA) (see Brockstedt, et al. (2004) Proc. Natl. Acad. Sci. USA 101: 13832-13837; supporting information). In another embodiment, the *Listeria* strain is *L. monocytogenes* DP-L4038 (delta ActA-LLO L461T) (see Brockstedt, et al. (2004) Proc. Natl. Acad. Sci. USA 101: 13832-13837; supporting information). In another embodiment, the *Listeria* strain is *L. monocytogenes* DP-L4384 (S44A-LLO L461T) (see Brockstedt, et al. (2004) Proc. Natl. Acad. Sci. USA 101: 13832-13837; supporting information). In another embodiment, the *Listeria* strain is *L. monocytogenes*. Mutation in lipoate protein (see O'Riordan, et al. (2003) Science 302: 462-464). In another embodiment, the *Listeria* strain is *L. monocytogenes* DP-L4017 (10403S hly (L461T), having a point mutation in hemolysin gene (see U.S. Provisional Pat. Appl. Ser. No. 60/490,089, filed Jul. 24, 2003). In another embodiment, the *Listeria* strain is *L. monocytogenes* EGD (see GenBank Acc. No. AL591824). In another embodiment, the *Listeria* strain is *L. monocytogenes* EGD-e (see GenBank Acc. No. NC_003210. ATCC Acc. No. BAA-679). In another embodiment, the *Listeria* strain is *L. monocytogenes* DP-L4029 deleted in uvrAB (see U.S. Provisional Pat. Appl. Ser. No. 60/541,515 filed Feb. 2, 2004; U.S. Provisional Pat. Appl. Ser. No. 60/490,080 filed Jul. 24, 2003). In another embodiment, the *Listeria* strain is *L. monocytogenes* ActA-/inlB—double mutant (see ATCC Acc. No. PTA-5562). In another embodiment, the *Listeria* strain is *L. monocytogenes* lplA mutant or hly mutant (see U.S. Pat. Applic. No. 20040013690 of Portnoy, et. al). In another embodiment, the *Listeria* strain is *L. monocytogenes* DAL/DAT double mutant. (see U.S. Pat. Applic. No. 20050048081 of Frankel and Portnoy. The present invention encompasses reagents and methods that comprise the above *Listerial* strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); dat (D-amino acid aminotransferase); plcA; plcB; actA; or any nucleic acid that mediates growth, spread, breakdown of a single walled vesicle, breakdown of a double walled vesicle, binding to a host cell, uptake by a host cell. The present invention is not to be limited by the particular strains disclosed above.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed as described herein (e.g. in Example 12). In another embodiment, the passaging is performed by any other method known in the art.

In another embodiment, the recombinant *Listeria* strain utilized in methods of the present invention has been stored in a frozen cell bank. In another embodiment, the recombinant *Listeria* strain has been stored in a lyophilized cell bank.

In another embodiment, the cell bank of methods and compositions of the present invention is a master cell bank. In another embodiment, the cell bank is a working cell bank. In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States.

In another embodiment, a recombinant *Listeria* strain utilized in methods of the present invention is from a batch of vaccine doses.

In another embodiment, a recombinant *Listeria* strain utilized in methods of the present invention is from a frozen or lyophilized stock produced by methods disclosed in U.S. Pat. No. 8,114,414, which is incorporated by reference herein.

In another embodiment, a peptide of the present invention is a fusion peptide. In another embodiment, "fusion peptide" refers to a peptide or polypeptide comprising 2 or more proteins linked together by peptide bonds or other chemical bonds. In another embodiment, the proteins are linked together directly by a peptide or other chemical bond. In another embodiment, the proteins are linked together with 1 or more AA (e.g. a "spacer") between the 2 or more proteins.

In another embodiment, a vaccine of the present invention further comprises an adjuvant. The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SmithKline Beecham adjuvant system 2 (SBAS2). In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a Quil glycoside. In another embodiment, the adjuvant is or comprises a bacterial mitogen. In another embodiment, the adjuvant is or comprises a bacterial toxin. In another embodiment, the adjuvant is or comprises any other adjuvant known in the art.

In another embodiment, a nucleotide of the present invention is operably linked to a promoter/regulatory sequence that drives expression of the encoded peptide in the *Listeria* strain. Promoter/regulatory sequences useful for driving constitutive expression of a gene are well known in the art and include, but are not limited to, for example, the P$_{hlyA}$, P$_{ActA}$, and p60 promoters of *Listeria*, the *Streptococcus* bac promoter, the *Streptomyces griseus* sgiA promoter, and the *B. thuringiensis* phaZ promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

An N-terminal fragment of an ActA protein utilized in methods and compositions of the present invention has, in another embodiment, the sequence set forth in SEQ ID NO: 5:

MRAMMVVFITANCITINPDIIFAATDSEDSSLNTDEWEEEKTEEQPSEVN

TGPRYETAREVSSRDIKELEKSNKVRNTNKADLIAMLKEKAEKGPNINNN

NSEQTENAAINEEASGADRPAIQVERRHPGLPSDSAAEIKKRRKAIASSD

SELESLTYPDKPTKVNKKKVAKESVADASESDLDSSMQSADESSPQPLKA

NQQPFFPKVFKKIKDAGKWVRDKIDENPEVKKAIVDKSAGLIDQLLTKKK

SEEVNASDFPPPPTDEELRLALPETPMLLGFNAPATSEPSSFEFPPPPTD

EELRLALPETPMLLGFNAPATSEPSSFEFPPPPTEDELEIIRETASSLDS

SFTRGDLASLRNAINRHSQNFSDFPPIPTEEELNGRGGRP.

In another embodiment, the ActA fragment comprises the sequence set forth in SEQ ID NO: 5. In another embodiment, the ActA fragment is any other ActA fragment known in the art.

In another embodiment, the recombinant nucleotide encoding a fragment of an ActA protein comprises the sequence set forth in SEQ ID NO: 6:

Atgcgtgcgatgatggtggttttcattactgccaattgcattacgattaa ccccgacataatatttgcagcgacagatagcgaagattctagtctaaaca cagatgaatgggaagaagaaaaaacagaagagcaaccaagcgaggtaaat acgggaccaagatacgaaactgcacgtgaagtaagttcacgtgatattaa agaactagaaaaatcgaataaagtgagaaatacgaacaaagcagacctaa tagcaatgttgaaagaaaaagcagaaaaaggtccaaatatcaataataac aacagtgaacaaactgagaatgcggctataaatgaagaggcttcaggagc cgaccgaccagctatacaagtggagcgtcgtcatccaggattgccatcgg atagcgcagcggaaattaaaaaaagaaggaaagccatagcatcatcggat agtgagcttgaaagccttacttatccggataaaccaacaaaagtaaataa gaaaaaagtggcgaaagagtcagttgcggatgcttctgaaagtgacttag attctagcatgcagtcagcagatgagtcttcaccacaacctttaaaagca aaccaacaaccattttttccctaaagtatttaaaaaaataaaagatgcggg gaaatgggtacgtgataaaatcgacgaaaatcctgaagtaaagaaagcga ttgttgataaaagtgcagggttaattgaccaattattaaccaaaaagaaa agtgaagaggtaaatgcttcggacttcccgccaccacctacggatgaaga gttaagacttgctttgccagagacaccaatgcttcttggttttaatgctc ctgctacatcagaaccgagctcattcgaatttccaccaccacctacggat gaagagttaagacttgctttgccagagacgccaatgcttcttggttttaa tgctcctgctacatcggaaccgagctcgttcgaatttccaccgcctccaa cagaagatgaactagaaatcatccgggaaacagcatcctcgctagattct agttttacaagaggggatttagctagtttgagaaatgctattaatcgcca tagtcaaaatttctctgatttcccaccaatcccaacagaagaagagttga acgggagaggcggtagacca.

In another embodiment, the recombinant nucleotide has the sequence set forth in SEQ ID NO: 6. In another embodiment, the recombinant nucleotide comprises any other sequence that encodes a fragment of an ActA protein.

In another embodiment of the methods and compositions of the present invention, a PEST amino acid AA sequence is fused to the E7 or E6 antigen. As disclosed herein, recombinant *Listeria* strains expressing PEST amino acid sequence-antigen fusions induce anti-tumor immunity (Example 3) and generate antigen-specific, tumor-infiltrating T cells (Example 4). Further, enhanced cell mediated immunity was demonstrated for fusion proteins comprising an antigen and LLO containing the PEST amino acid AA sequence KENSISSMAPPASPPASPKTPIEKKHADEIDK (SEQ ID NO: 1).

Thus, fusion of an antigen to other LM PEST amino acid sequences and PEST amino acid sequences derived from other prokaryotic organisms will also enhance immunogenicity of the antigen. The PEST amino acid AA sequence has, in another embodiment, a sequence selected from SEQ ID NO: 7-12. In another embodiment, the PEST amino acid sequence is a PEST amino acid sequence from the LM ActA protein. In another embodiment, the PEST amino acid sequence is KTEEQPSEVNTGPR (SEQ ID NO: 7), KASVTDTSEGDLDSSMQSADESTPQPLK (SEQ ID NO: 8), KNEEVNASDFPPPPTDEELR (SEQ ID NO: 9), or RGGIPTSEEFSSLNSGDFTDDENSETTEEEIDR (SEQ ID NO: 10). In another embodiment, the PEST amino acid sequence is from Streptolysin O protein of *Streptococcus* sp. In another embodiment, the PEST amino acid sequence is from *Streptococcus pyogenes* Streptolysin O, e.g. KQNTASTETTTTNEQPK (SEQ ID NO: 11) at AA 35-51. In another embodiment, the PEST amino acid sequence is from *Streptococcus equisimilis* Streptolysin O, e.g. KQNTANTETTTTNEQPK (SEQ ID NO:12) at AA 38-54. In another embodiment, the PEST amino acid sequence is another PEST amino acid AA sequence derived from a prokaryotic organism. In another embodiment, the PEST amino acid sequence is any other PEST amino acid sequence known in the art.

PEST amino acid sequences of other prokaryotic organism can be identified in accordance with methods such as described by, for example Rechsteiner and Rogers (1996, Trends Biochem. Sci. 21:267-271) for LM. Alternatively, PEST amino acid AA sequences from other prokaryotic organisms can also be identified based by this method. Other prokaryotic organisms wherein PEST amino acid AA sequences would be expected to include, but are not limited to, other *Listeria* species. In another embodiment, the PEST amino acid sequence is embedded within the antigenic protein. Thus, in another embodiment, "fusion" refers to an antigenic protein comprising both the antigen and the PEST amino acid amino acid sequence either linked at one end of the antigen or embedded within the antigen.

In another embodiment, the PEST amino acid sequence is identified using any other method or algorithm known in the art, e.g. the CaSPredictor (Garay-Malpartida H M, Occhiucci J M, Alves J, and Belizario J E. Bioinformatics. 2005 June; 21 Suppl 1:i169-76). In another embodiment, the following method is used:

A PEST index is calculated for each 30-35 AA stretch by assigning a value of 1 to the amino acids Ser, Thr, Pro, Glu, Asp, Asn, or Gln. The coefficient value (CV) for each of the PEST residue is 1 and for each of the other AA (non-PEST) is 0.

In another embodiment, the LLO protein, ActA protein, or fragment thereof of the present invention need not be that which is set forth exactly in the sequences set forth herein, but rather other alterations, modifications, or changes can be made that retain the functional characteristics of an LLO or ActA protein fused to an antigen as set forth elsewhere herein. In another embodiment, the present invention utilizes an analog of an LLO protein, ActA protein, or fragment thereof. Analogs differ, in another embodiment, from naturally occurring proteins or peptides by conservative AA sequence differences or by modifications which do not affect sequence, or by both.

In another embodiment, either a whole E7 protein or a fragment thereof is fused to a LLO protein, ActA protein, or PEST amino acid sequence-containing peptide to generate a recombinant peptide of methods of the present invention. The E7 protein that is utilized (either whole or as the source of the fragments) has, in another embodiment, the sequence

```
                                            (SEQ ID No: 13)
MHGDTPTLHEYMLDLQPETTDLYCYEQLNDSSEEEDEIDGPAGQAEPD
RAHYNIVTFCCKCDSTLRLCVQSTHVDIRTLEDLLMGTLGIVCPICSQ
KP.
```

In another embodiment, the E7 protein is a homologue of SEQ ID No: 13. In another embodiment, the E7 protein is a variant of SEQ ID No: 13. In another embodiment, the E7 protein is an isomer of SEQ ID No: 13. In another embodiment, the E7 protein is a fragment of SEQ ID No: 13. In another embodiment, the E7 protein is a fragment of a homologue of SEQ ID No: 13. In another embodiment, the E7 protein is a fragment of a variant of SEQ ID No: 13. In another embodiment, the E7 protein is a fragment of an isomer of SEQ ID No: 13.

In another embodiment, the sequence of the E7 protein is:

```
                                            (SEQ ID No: 14)
MHGPKATLQDIVLHLEPQNEIPVDLLCHEQLSDSEEENDEIDGVNHQH
LPARRAEPQRHTMLCMCCKCEARIELVVESSADDLRAFQQLFLNTLSFVC
PWCASQQ.
```

In another embodiment, the E7 protein is a homologue of SEQ ID No: 14. In another embodiment, the E7 protein is a variant of SEQ ID No: 14. In another embodiment, the E7 protein is an isomer of SEQ ID No: 14. In another embodiment, the E7 protein is a fragment of SEQ ID No: 14. In another embodiment, the E7 protein is a fragment of a homologue of SEQ ID No: 14. In another embodiment, the E7 protein is a fragment of a variant of SEQ ID No: 14. In another embodiment, the E7 protein is a fragment of an isomer of SEQ ID No: 14.

In another embodiment, the E7 protein has a sequence set forth in one of the following GenBank entries: M24215, NC_004500, V01116, X62843, or M14119. In another embodiment, the E7 protein is a homologue of a sequence from one of the above GenBank entries. In another embodiment, the E7 protein is a variant of a sequence from one of the above GenBank entries. In another embodiment, the E7 protein is an isomer of a sequence from one of the above GenBank entries. In another embodiment, the E7 protein is a fragment of a sequence from one of the above GenBank entries. In another embodiment, the E7 protein is a fragment of a homologue of a sequence from one of the above GenBank entries. In another embodiment, the E7 protein is a fragment of a variant of a sequence from one of the above GenBank entries. In another embodiment, the E7 protein is a fragment of an isomer of a sequence from one of the above GenBank entries.

In another embodiment, either a whole E6 protein or a fragment thereof is fused to a LLO protein, ActA protein, or PEST amino acid sequence-containing peptide to generate a recombinant peptide of methods of the present invention. The E6 protein that is utilized (either whole or as the source of the fragments) has, in another embodiment, the sequence

```
                                                    (SEQ ID No: 15)
MHQKRTAMFQDPQERPRKLPQLCTELQTTIHDIILECVYCKQQLLRRE

VYDFAFRDLCIVYRDGNPYAVCDKCLKFYSKISEYRHYCYSLYGTTLEQQ

YNKPLCDLLIRCINCQKPLCPEEKQRHLDKKQRFHNIRGRWTGRCMSCCR

SSRTRRETQL.
```

In another embodiment, the E6 protein is a homologue of SEQ ID No: 15. In another embodiment, the E6 protein is a variant of SEQ ID No: 15. In another embodiment, the E6 protein is an isomer of SEQ ID No: 15. In another embodiment, the E6 protein is a fragment of SEQ ID No: 15. In another embodiment, the E6 protein is a fragment of a homologue of SEQ ID No: 15. In another embodiment, the E6 protein is a fragment of a variant of SEQ ID No: 15. In another embodiment, the E6 protein is a fragment of an isomer of SEQ ID No: 15.

In another embodiment, the sequence of the E6 protein is:

```
                                                    (SEQ ID No: 16)
MARFEDPTRRPYKLPDLCTELNTSLQDIEITCVYCKTVLELTEVFEFAF

KDLFVVYRDSIPHAACHKCIDFYSRIRELRHYSDSVYGDTLEKLTNTGLY

NLLIRCLRCQKPLNPAEKLRHLNEKRRFHNIAGHYRGQCHSCCNRARQER

LQRRRETQV.
```

In another embodiment, the E6 protein is a homologue of SEQ ID No: 16. In another embodiment, the E6 protein is a variant of SEQ ID No: 16. In another embodiment, the E6 protein is an isomer of SEQ ID No: 16. In another embodiment, the E6 protein is a fragment of SEQ ID No: 16. In another embodiment, the E6 protein is a fragment of a homologue of SEQ ID No: 16. In another embodiment, the E6 protein is a fragment of a variant of SEQ ID No: 16. In another embodiment, the E6 protein is a fragment of an isomer of SEQ ID No: 16.

In another embodiment, the E6 protein has a sequence set forth in one of the following GenBank entries: M24215, M14119, NC_004500, V01116, X62843, or M14119. In another embodiment, the E6 protein is a homologue of a sequence from one of the above GenBank entries. In another embodiment, the E6 protein is a variant of a sequence from one of the above GenBank entries. In another embodiment, the E6 protein is an isomer of a sequence from one of the above GenBank entries. In another embodiment, the E6 protein is a fragment of a sequence from one of the above GenBank entries. In another embodiment, the E6 protein is a fragment of a homologue of a sequence from one of the above GenBank entries. In another embodiment, the E6 protein is a fragment of a variant of a sequence from one of the above GenBank entries. In another embodiment, the E6 protein is a fragment of an isomer of a sequence from one of the above GenBank entries.

In another embodiment, "homology" refers to identity to an LLO sequence (e.g. to one of SEQ ID No: 2-4) of greater than 70%. In another embodiment, "homology" refers to identity to one of SEQ ID No: 2-4 of greater than 64%. In another embodiment, "homology" refers to identity to one of SEQ ID No: 2-4 of greater than 68%. In another embodiment, "homology" refers to identity to one of SEQ ID No: 2-4 of greater than 72%. In another embodiment, "homology" refers to identity to one of SEQ ID No: 2-4 of greater than 75%. In another embodiment, "homology" refers to identity to one of SEQ ID No: 2-4 of greater than 78%. In another embodiment, "homology" refers to identity to one of SEQ ID No: 2-4 of greater than 80%. In another embodiment, "homology" refers to identity to one of SEQ ID No: 2-4 of greater than 82%. In another embodiment, "homology" refers to identity to one of SEQ ID No: 2-4 of greater than 83%. In another embodiment, "homology" refers to identity to one of SEQ ID No: 2-4 of greater than 85%. In another embodiment, "homology" refers to identity to one of SEQ ID No: 2-4 of greater than 87%. In another embodiment, "homology" refers to identity to one of SEQ ID No: 2-4 of greater than 88%. In another embodiment, "homology" refers to identity to one of SEQ ID No: 2-4 of greater than 90%. In another embodiment, "homology" refers to identity to one of SEQ ID No: 2-4 of greater than 92%. In another embodiment, "homology" refers to identity to one of SEQ ID No: 2-4 of greater than 93%. In another embodiment, "homology" refers to identity to one of SEQ ID No: 2-4 of greater than 95%. In another embodiment, "homology" refers to identity to one of SEQ ID No: 2-4 of greater than 96%. In another embodiment, "homology" refers to identity to one of SEQ ID No: 2-4 of greater than 97%. In another embodiment, "homology" refers to identity to one of SEQ ID No: 2-4 of greater than 98%. In another embodiment, "homology" refers to identity to one of SEQ ID No: 2-4 of greater than 99%. In another embodiment, "homology" refers to identity to one of SEQ ID No: 2-4 of 100%.

In another embodiment, "homology" refers to identity to an E7 sequence (e.g. to one of SEQ ID No: 13-14) of greater than 70%. In another embodiment, "homology" refers to identity to one of SEQ ID No: 13-14 of greater than 62%. In another embodiment, "homology" refers to identity to one of SEQ ID No: 13-14 of greater than 64%. In another embodiment, "homology" refers to identity to one of SEQ ID No: 13-14 of greater than 68%. In another embodiment, "homology" refers to identity to one of SEQ ID No: 13-14 of greater than 72%. In another embodiment, "homology" refers to identity to one of SEQ ID No: 13-14 of greater than 75%. In another embodiment, "homology" refers to identity to one of SEQ ID No: 13-14 of greater than 78%. In another embodiment, "homology" refers to identity to one of SEQ ID No: 13-14 of greater than 80%. In another embodiment, "homology" refers to identity to one of SEQ ID No: 13-14 of greater than 82%. In another embodiment, "homology" refers to identity to one of SEQ ID No: 13-14 of greater than 83%. In another embodiment, "homology" refers to identity to one of SEQ ID No: 13-14 of greater than 85%. In another embodiment, "homology" refers to identity to one of SEQ ID No: 13-14 of greater than 87%. In another embodiment, "homology" refers to identity to one of SEQ ID No: 13-14 of greater than 88%. In another embodiment, "homology" refers to identity to one of SEQ ID No: 13-14 of greater than 90%. In another embodiment, "homology" refers to identity to one of SEQ ID No: 13-14 of greater than 92%. In another embodiment, "homology" refers to identity to one of SEQ ID No: 13-14 of greater than 93%. In another embodiment, "homology" refers to identity to one of SEQ ID No: 13-14 of greater than 95%. In another embodiment, "homology" refers to identity to one of SEQ ID No: 13-14 of greater than 96%. In another embodiment, "homology" refers to identity to one of SEQ ID No: 13-14 of greater than 97%. In another embodiment, "homology" refers to identity to one of SEQ ID No: 13-14 of greater than 98%. In another embodiment, "homology" refers to identity to one of SEQ ID No: 13-14 of greater than 99%. In another embodiment, "homology" refers to identity to one of SEQ ID No: 13-14 of 100%.

In another embodiment, "homology" refers to identity to an E6 sequence (e.g. to one of SEQ ID No: 15-16) of greater than 70%. In another embodiment, "homology" refers to identity to one of SEQ ID No: 15-16 of greater than 64%. In another embodiment, "homology" refers to identity to one of SEQ ID No: 15-16 of greater than 68%. In another embodiment, "homology" refers to identity to one of SEQ ID No: 15-16 of greater than 72%. In another embodiment, "homology" refers to identity to one of SEQ ID No: 15-16 of greater than 75%. In another embodiment, "homology" refers to identity to one of SEQ ID No: 15-16 of greater than 78%. In another embodiment, "homology" refers to identity to one of SEQ ID No: 15-16 of greater than 80%. In another embodiment, "homology" refers to identity to one of SEQ ID No: 15-16 of greater than 82%. In another embodiment, "homology" refers to identity to one of SEQ ID No: 15-16 of greater than 83%. In another embodiment, "homology" refers to identity to one of SEQ ID No: 15-16 of greater than 85%. In another embodiment, "homology" refers to identity to one of SEQ ID No: 15-16 of greater than 87%. In another embodiment, "homology" refers to identity to one of SEQ ID No: 15-16 of greater than 88%. In another embodiment, "homology" refers to identity to one of SEQ ID No: 15-16 of greater than 90%. In another embodiment, "homology" refers to identity to one of SEQ ID No: 15-16 of greater than 92%. In another embodiment, "homology" refers to identity to one of SEQ ID No: 15-16 of greater than 93%. In another embodiment, "homology" refers to identity to one of SEQ ID No: 15-16 of greater than 95%. In another embodiment, "homology" refers to identity to one of SEQ ID No: 15-16 of greater than 96%. In another embodiment, "homology" refers to identity to one of SEQ ID No: 15-16 of greater than 97%. In another embodiment, "homology" refers to identity to one of SEQ ID No: 15-16 of greater than 98%. In another embodiment, "homology" refers to identity to one of SEQ ID No: 15-16 of greater than 99%. In another embodiment, "homology" refers to identity to one of SEQ ID No: 15-16 of 100%.

In another embodiment, "homology" refers to identity to a PEST amino acid sequence (e.g. to one of SEQ ID No: 1, and 7-12) or to an ActA sequence (e.g. to one of SEQ ID No: 5-6) of greater than 70%. In another embodiment, "homology" refers to identity to one of SEQ ID No: 1, and 7-12 or SEQ ID No: 5-6 of greater than 60%. In another embodiment, "homology" refers to identity to one of SEQ ID No: 1, and 7-12 or SEQ ID No: 5-6 of greater than 64%. In another embodiment, "homology" refers to identity to one of SEQ ID No: 1, and 7-12 or SEQ ID No: 5-6 of greater than 68%. In another embodiment, "homology" refers to identity to one of SEQ ID No: 1, and 7-12 or SEQ ID No: 5-6 of greater than 72%. In another embodiment, "homology" refers to identity to one of SEQ ID No: 1, and 7-12 or SEQ ID No: 5-6 of greater than 75%. In another embodiment, "homology" refers to identity to one of SEQ ID No: 1, and 7-12 or SEQ ID No: 5-6 of greater than 78%. In another embodiment, "homology" refers to identity to one of SEQ ID No: 1, and 7-12 or SEQ ID No: 5-6 of greater than 80%. In another embodiment, "homology" refers to identity to one of SEQ ID No: 1, and 7-12 or SEQ ID No: 5-6 of greater than 82%. In another embodiment, "homology" refers to identity to one of SEQ ID No: 1, and 7-12 or SEQ ID No: 5-6 of greater than 83%. In another embodiment, "homology" refers to identity to one of SEQ ID No: 1, and 7-12 or SEQ ID No: 5-6 of greater than 85%. In another embodiment, "homology" refers to identity to one of SEQ ID No: 1, and 7-12 or SEQ ID No: 5-6 of greater than 87%. In another embodiment, "homology" refers to identity to one of SEQ ID No: 1, and 7-12 or SEQ ID No: 5-6 of greater than 88%. In another embodiment, "homology" refers to identity to one of SEQ ID No: 1, and 7-12 or SEQ ID No: 5-6 of greater than 90%. In another embodiment, "homology" refers to identity to one of SEQ ID No: 1, and 7-12 or SEQ ID No: 5-6 of greater than 92%. In another embodiment, "homology" refers to identity to one of SEQ ID No: 1, and 7-12 or SEQ ID No: 5-6 of greater than 93%. In another embodiment, "homology" refers to identity to one of SEQ ID No: 1, and 7-12 or SEQ ID No: 5-6 of greater than 95%. In another embodiment, "homology" refers to identity to one of SEQ ID No: 1, and 7-12 or SEQ ID No: 5-6 of greater than 96%. In another embodiment, "homology" refers to identity to one of SEQ ID No: 1, and 7-12 or SEQ ID No: 5-6 of greater than 97%. In another embodiment, "homology" refers to identity to one of SEQ ID No: 1, and 7-12 or SEQ ID No: 5-6 of greater than 98%. In another embodiment, "homology" refers to identity to one of SEQ ID No: 1, and 7-12 or SEQ ID No: 5-6 of greater than 99%. In another embodiment, "homology" refers to identity to one of SEQ ID No: 1, and 7-12 or SEQ ID No: 5-6 of 100%.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and employ, in other embodiments, the use of the Smith and Waterman algorithms, and/or global/local or BLOCKS alignments for analysis, for example.

In another embodiment, the LLO protein, ActA protein, or fragment thereof is attached to the antigen by chemical conjugation. In another embodiment, glutaraldehyde is used for the conjugation. In another embodiment, the conjugation is performed using any suitable method known in the art.

In another embodiment, fusion proteins of the present invention are prepared by any suitable method, including, for example, cloning and restriction of appropriate sequences or direct chemical synthesis by methods discussed below. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid.

In another embodiment, the LLO protein, ActA protein, or fragment thereof and the antigen, or fragment thereof are conjugated by a means known to those of skill in the art. In another embodiment, the antigen, or fragment thereof is conjugated, either directly or through a linker (spacer), to the ActA protein or LLO protein. In another embodiment, the chimeric molecule is recombinantly expressed as a single-chain fusion protein.

In another embodiment, a fusion peptide of the present invention is synthesized using standard chemical peptide synthesis techniques. In another embodiment, the chimeric molecule is synthesized as a single contiguous polypeptide. In another embodiment, the LLO protein, ActA protein, or fragment thereof; and the antigen, or fragment thereof are synthesized separately, then fused by condensation of the amino terminus of one molecule with the carboxyl terminus of the other molecule, thereby forming a peptide bond. In another embodiment, the ActA protein or LLO protein and antigen are each condensed with one end of a peptide spacer molecule, thereby forming a contiguous fusion protein.

In another embodiment, the peptides and proteins of the present invention are prepared by solid-phase peptide synthesis (SPPS) as described by Stewart et al. in Solid Phase Peptide Synthesis, 2nd Edition, 1984, Pierce Chemical Company, Rockford, Ill.; or as described by Bodanszky and Bodanszky (The Practice of Peptide Synthesis, 1984, Springer-Verlag, New York). In another embodiment, a suitably protected AA residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial AA, and couple thereto of the carboxyl end of the next AA in the sequence of the desired peptide. This AA is also suitably protected. The carboxyl of the incoming AA can be activated to react with the N-terminus of the support-bound AA by formation into a reactive group such as formation into a carbodiimide, a symmetric acid anhydride or an "active ester" group such as hydroxybenzotriazole or pentafluorophenly esters.

In another embodiment, the present invention provides a kit comprising vaccine of the present invention, an applicator, and instructional material that describes use of the methods of the invention. Although model kits are described below, the contents of other useful kits will be apparent to the skilled artisan in light of the present disclosure. Each of these kits represents a separate embodiment of the present invention.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequelae. The subject may include dogs, cats, pigs, cows, sheep, goats, horses, rats, pets mice and humans. The subject may also include livestock. In one embodiment, the term "subject" does not exclude an individual that is healthy in all respects and does not have or show signs of disease or disorder.

The following examples are presented in order to more fully illustrate the preferred embodiments of the invention. They should in no way be construed, however, as limiting the broad scope of the invention.

EXPERIMENTAL DETAILS SECTION

Example 1: LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1, disclosed by T. C. Wu (Johns Hopkins University School of Medicine, Baltimore, Md.) is a highly tumorigenic lung epithelial cell expressing low levels of with HPV-16 E6 and E7 and transformed with the c-Ha-ras oncogene. TC-1 was grown in RPMI 1640, 10% FCS, 2 mM L-glutamine, 100 Um' penicillin, 100 µg/ml streptomycin, 100 µM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

L. monocytogenes Strains and Propagation

Figure 2:
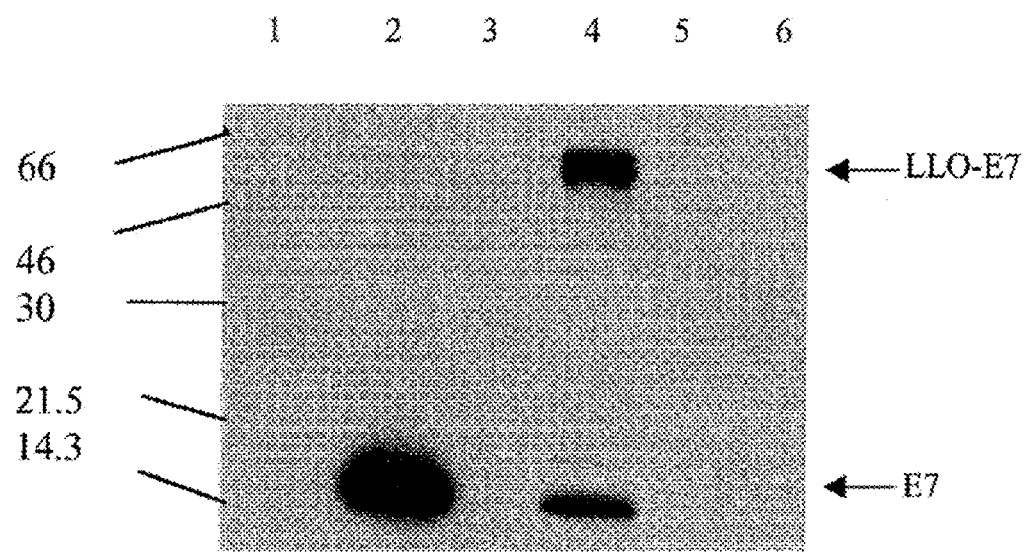
FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

Listeria strains used were Lm-LLO-E7 (hly-E7 fusion gene in an episomal expression system; FIG. 1A), Lm-E7 (single-copy E7 gene cassette integrated into Listeria genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GG<u>CTCGAG</u>CATGGAGATACACC-3' (SEQ ID No: 17; XhoI site is underlined) and 5'-GGGG <u>ACTAGT</u>TTATGGTTTCTGAGAACA-3' (SEQ ID No: 18; SpeI site is underlined) and ligated into pCR2.1 (Invitrogen, San Diego, Calif.). E7 was excised from pCR2.1 by XhoI/SpeI digestion and ligated into pGG-55 (FIG. 1B). The hly-E7 fusion gene and the pluripotential transcription factor PrfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO," and having the sequence set forth in SEQ ID No: 25), which is joined by the XhoI site to the E7 gene, yielding a hly-E7 fusion gene that is transcribed and secreted as LLO-E7. Transformation of a prfA negative strain of Listeria, XFL-7 (disclosed by Dr. Hao Shen, University of Pennsylvania), with pGG-55 selected for the retention of the plasmid in vivo (FIGS. 1A-B). The hly promoter and gene fragment were generated using primers 5'-GGGG<u>GCTAGC</u>CCTCCTTTGATTAGTATATTC-3' (SEQ ID No: 19; NheI site is underlined) and 5'-CTCC<u>CTCGAG</u>ATCATAAATTTACTTCATC-3' (SEQ ID No: 20; XhoI site is underlined). The prfA gene was PCR amplified using primers 5'-GACTACAAGGACGATGACCGA-CAAGTGATA<u>ACCCGGG</u>ATCTAAATAAATCCGTT T-3' (SEQ ID No: 27; XbaI site is underlined) and 5'-CCC<u>GTCGAC</u>CAGCTCTTCTTGGTGAAG-3' (SEQ ID No: 21; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GC<u>GGATCC</u>CATGGAGATACACCTAC-3' (SEQ ID No: 22; BamHI site is underlined) and 5'-GC<u>TCTAGA</u>TTATGGTTTCTGAG-3' (SEQ ID No: 23; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 μg/ml). Bacteria were frozen in aliquots at −80° C. Expression was verified by Western blotting (FIG. 2).

Western Blotting

*Listeria* strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of *Listeria* Recombinants on Established Tumor Growth

Six- to 8-wk-old C57BL/6 mice (Charles River) received $2\times10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5\times10^5$ CFU) on days 7 and 14.

$^{51}$Cr Release Assay

C57BL/6 mice, 6-8 wk old, were immunized i.p. with 0.1$LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF). E:T cell ratios, performed in triplicate, were 80:1, 40:1, 20:1, 10:1, 5:1, and 2.5:1. Following a 4-h incubation at 37° C., cells were pelleted, and 50 μl supernatant was removed from each well. Samples were assayed with a Wallac 1450 scintillation counter (Gaithersburg, Md.). The percent specific lysis was determined as [(experimental counts per minute (cpm)−spontaneous cpm)/(total cpm−spontaneous cpm)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5\times10^5$/well in flat-bottom 96-well plates with $2.5\times10^4$, $1.25\times10^4$, $6\times10^3$, or $3\times10^3$ irradiated TC-1 cells/well as a source of E7 Ag, or without TC-1 cells or with 10 μg/ml Con A. Cells were pulsed 45 h later with 0.5 μCi [$^3$H]thymidine/well. Plates were harvested 18 h later using a Tomtec harvester 96 (Orange, Conn.), and proliferation was assessed with a Wallac 1450 scintillation counter. The change in cpm was calculated as experimental cpm−no Ag cpm.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2Db tetramer was performed using a FACSCALIBUR™ flow cytometer with CELLQUEST® software (Becton Dickinson, Mountain View, Calif.). Splenocytes harvested 5 days after the boost were stained at room temperature (rt) with H-2Db tetramers loaded with the E7 peptide (RAHYNIVTF) or a control (HIV-Gag) peptide. Tetramers were used at a 1/200 dilution and were disclosed by Dr. Larry R. Pease (Mayo Clinic, Rochester, Minn.) and by the NIAID Tetramer Core Facility and the NIH AIDS Research and Reference Reagent Program. Tetramer$^+$, CD8$^+$, CD62L$^{low}$ cells were analyzed.

B16F0-Ova Experiment

24 C57BL/6 mice were inoculated with $5\times10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. p≤0.05 was considered significant.

Results

Figure 3:
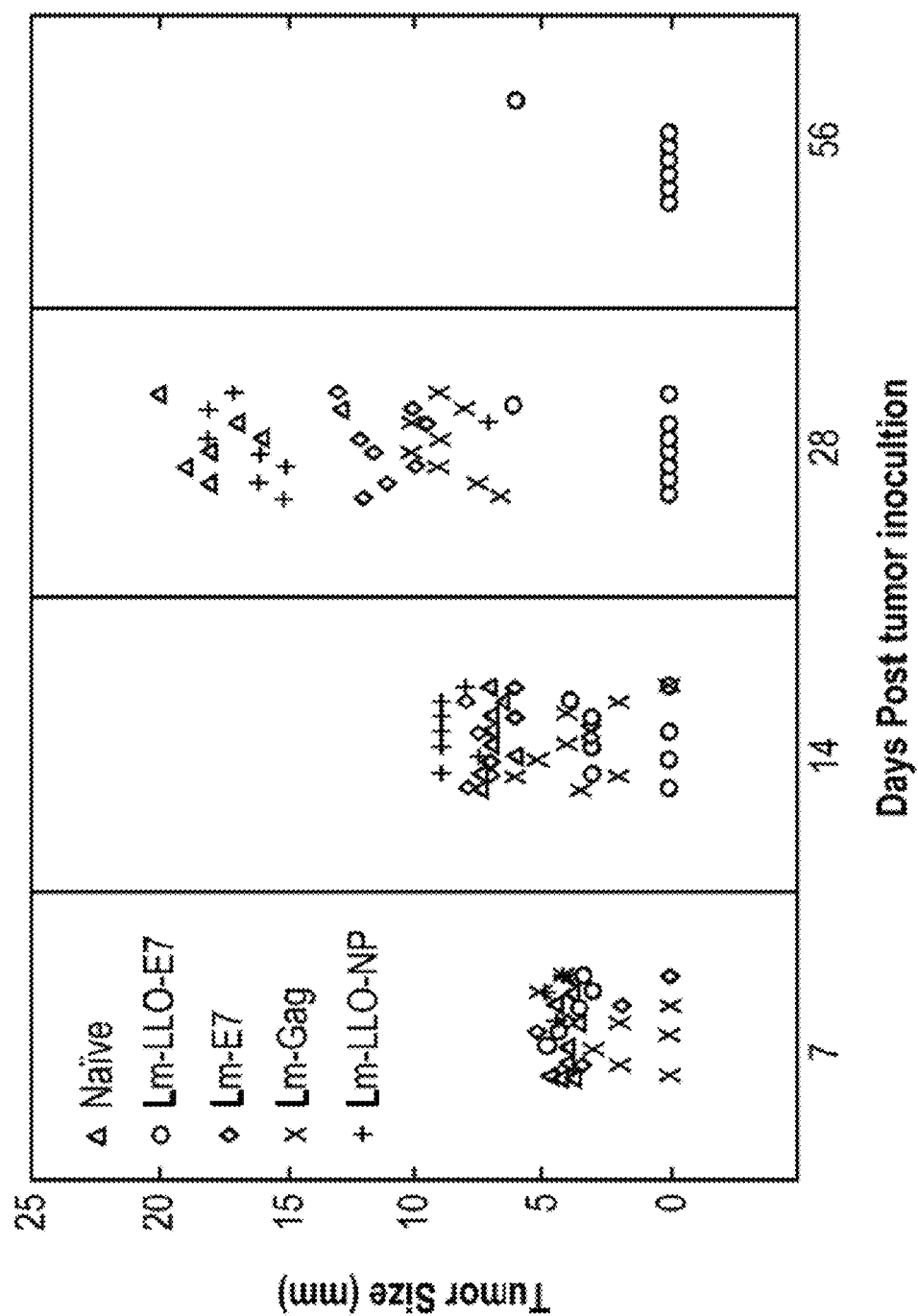
FIG. 3. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Thus, expression of an antigen as a fusion protein with ALLO enhances the immunogenicity of the antigen.

Example 2: Lm-LLO-E7 Treatment Elicits TC-1 Specific Splenocyte Proliferation

Figure 4:
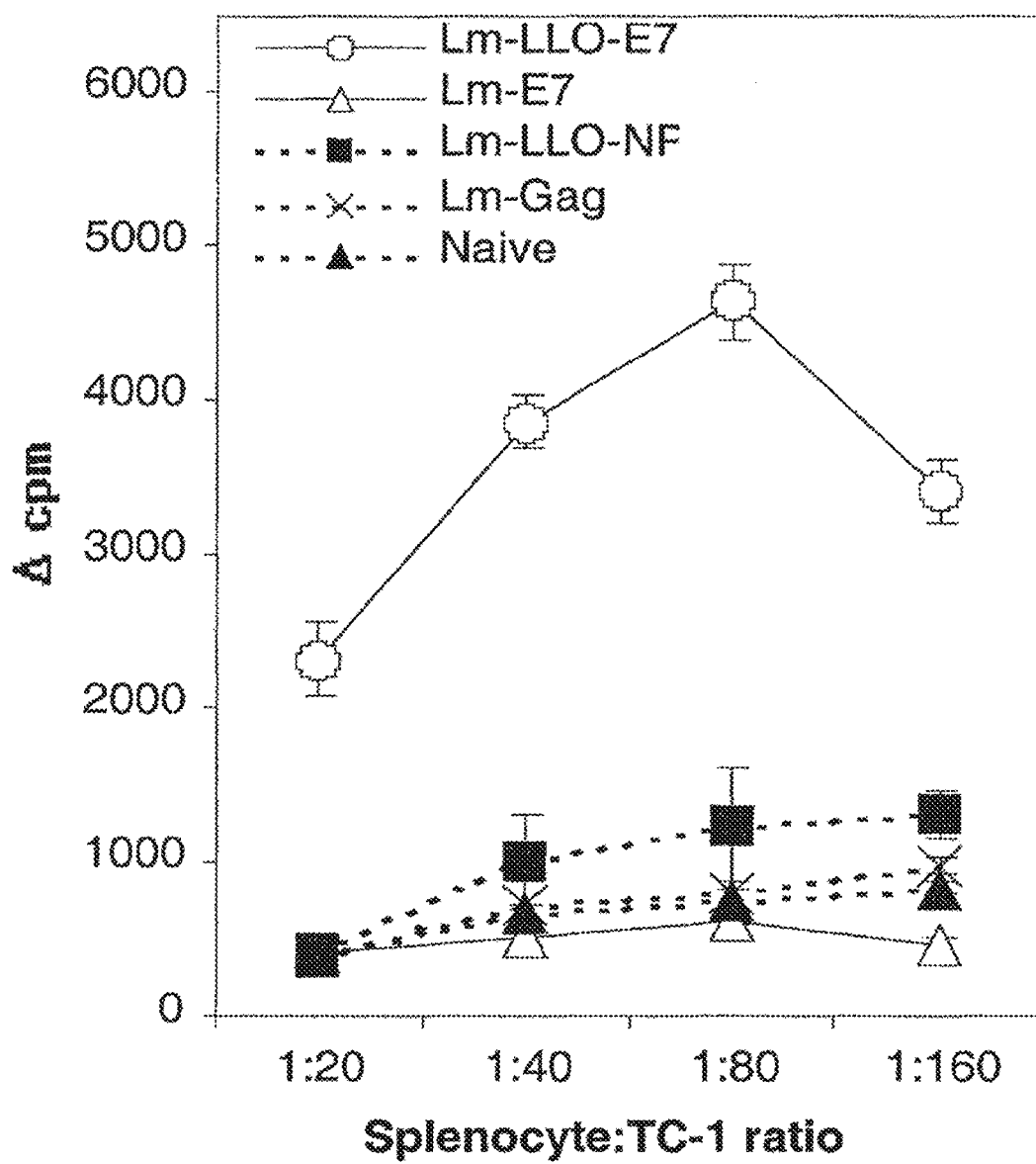
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)—(no-TC-1 control).

To measure induction of T cells by Lm-E7 with Lm-LLO-E7, TC-1-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3: Fusion of E7 to LLO, ActA, or a Pest Amino Acid Sequence Enhances E7-Specific Immunity and Generates Tumor-Infiltrating E7-Specific CD8+ Cells Materials and Experimental Methods 500 mcl (microliter) of MATRIGEL® basement membrane matrix, comprising 100 mcl of 2×10⁵ TC-1 tumor cells in phosphate buffered saline (PBS) plus 400 mcl of MATRIGEL® basement membrane matrix (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGEL®s basement membrane matrices were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-Stop® or Golgi-Plug® (Pharmingen, San Diego, Calif.), and stained for IFN-gamma. 500,000 events were acquired using two-laser flow cytometer FACSCALIBUR™ flow cytometer and analyzed using CELLQUEST® Software (Becton Dickinson, Franklin Lakes, N.J.). Percentages of IFN-gamma secreting cells within the activated ($CD62L^{low}$) CD8+ T cells were calculated.

For tetramer staining, $H-2D^b$ tetramer was loaded with phycoerythrin (PE)-conjugated E7 peptide (RAHYNIVTF, SEQ ID NO: 24), stained at rt for 1 hour, and stained with anti-allophycocyanin (APC) conjugated MEL-14 (CD62L) and FITC-conjugated CD8☐ at 4° C. for 30 min. Cells were analyzed comparing tetramer+CD8+ $CD62L^{low}$ cells in the spleen and in the tumor.

Results

Figure 5A:
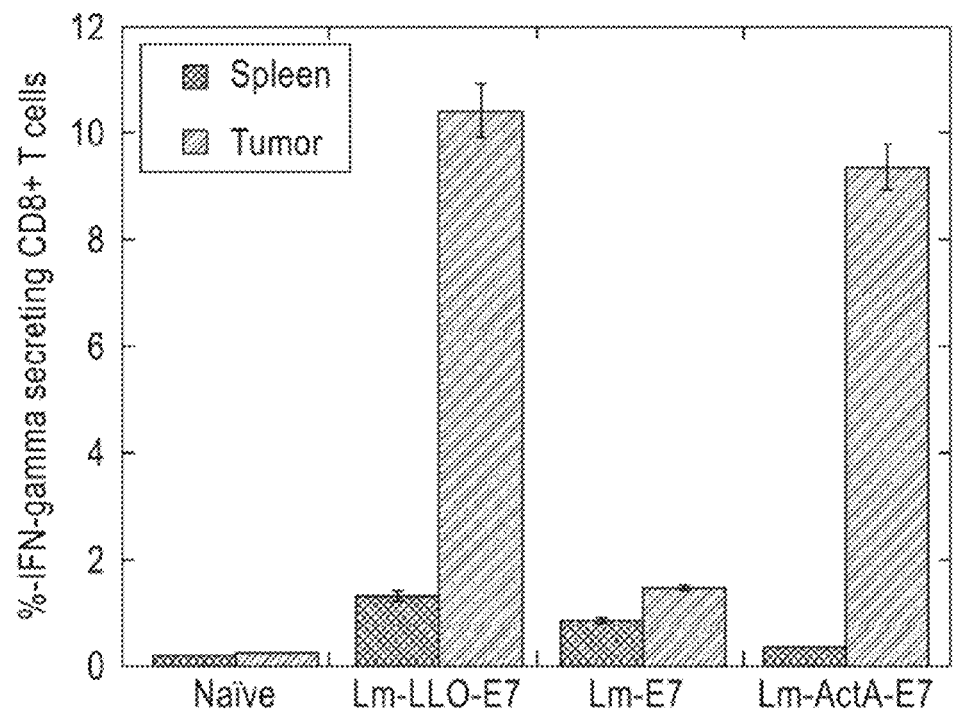
FIG. 5A-B.
Figure 5B:
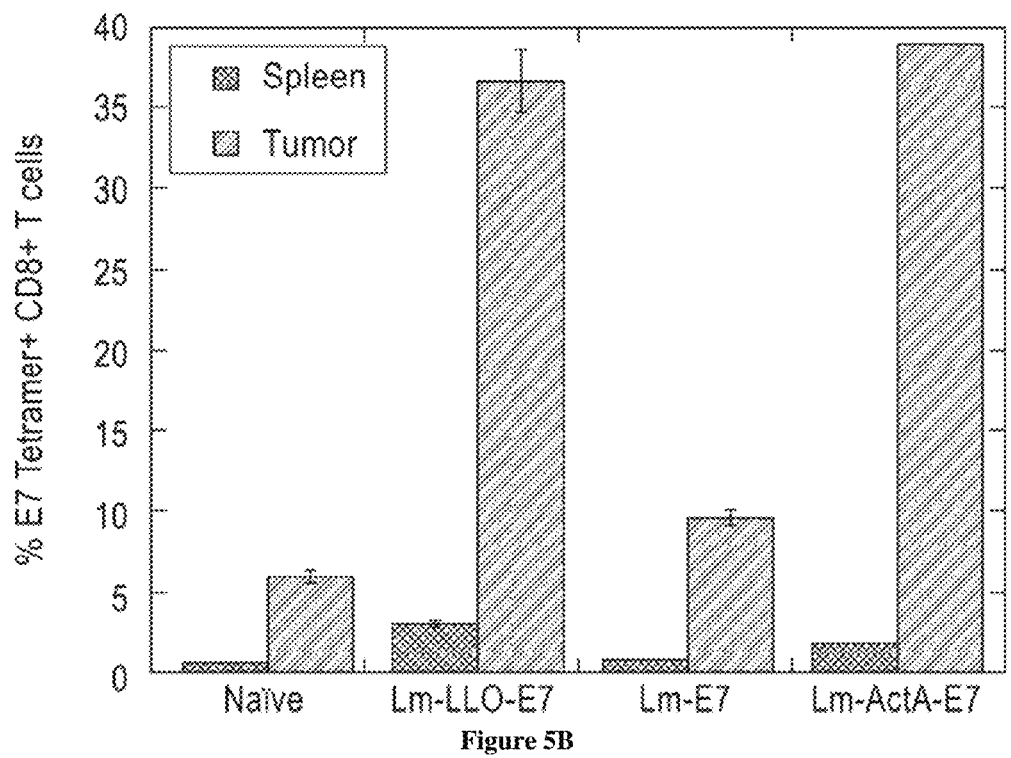

To analyze the ability of Lm-ActA-E7 to enhance antigen specific immunity, mice were implanted with TC-1 tumor cells and immunized with either Lm-LLO-E7 (1×10⁷ CFU), Lm-E7 (1×10⁶ CFU), or Lm-ActA-E7 (2×10⁸ CFU), or were untreated (naïve). Tumors of mice from the Lm-LLO-E7 and Lm-ActA-E7 groups contained a higher percentage of IFN-gamma-secreting CD8+ T cells (FIG. 5A) and tetramer-specific CD8+ cells (FIG. 5B) than in Lm-E7 or naive mice.

Figure 6A:
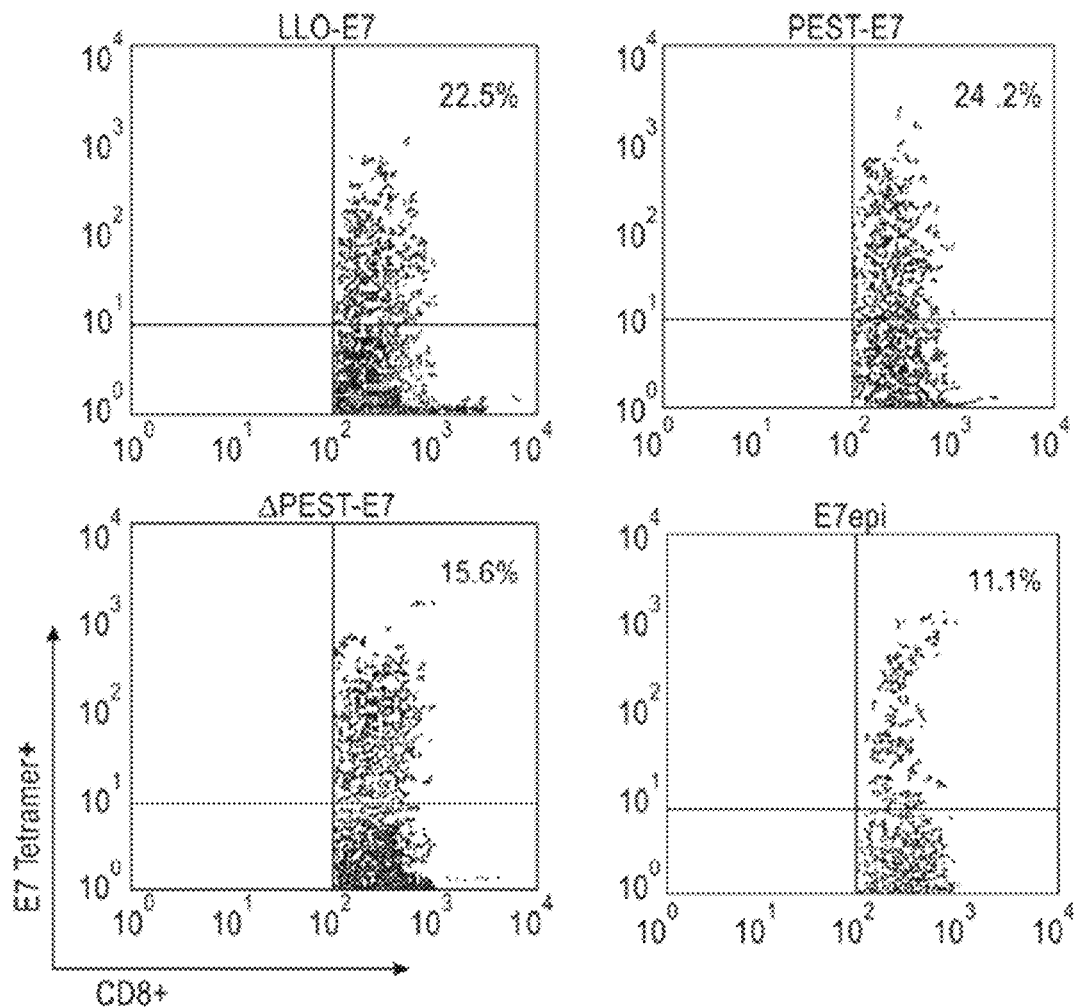
FIG. 6A-B. *Listeria* constructs containing PEST regions induce a higher percentage of E7-specific lymphocytes within the tumor.
Figure 6B:
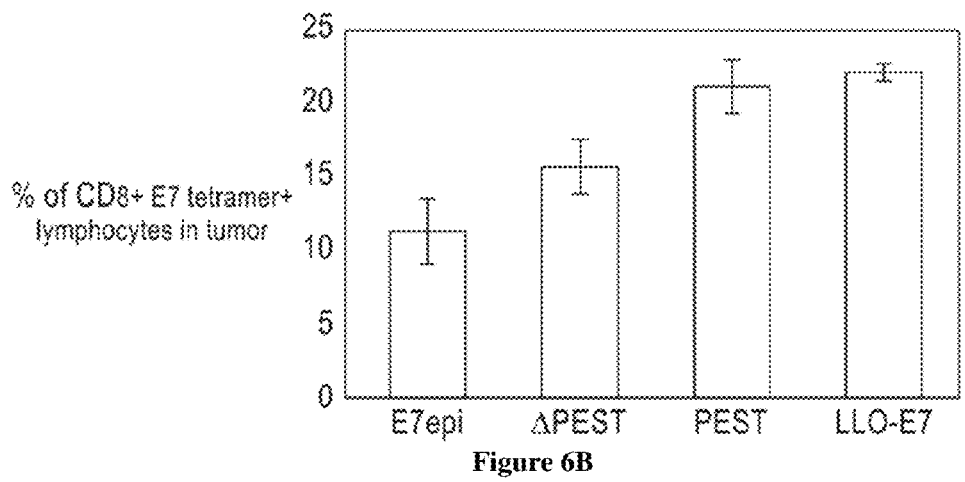

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 $LD_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 6A). This result was reproducible over three experiments (FIG. 6B).

Thus, Lm-LLO-E7, Lm-ActA-E7, and Lm-PEST-E7 are each efficacious at induction of tumor-infiltrating CD8+ T cells and tumor regression.

Example 4: Passaging of *Listeria* Vaccine Vectors Through Mice Elicits Increased Immune Responses to Heterologous and Endogenous Antigens Materials and Experimental Methods Bacterial Strains

*L. monocytogenes* strain 10403S, serotype 1 (ATCC, Manassas, Va.) was the wild type organism used in these studies and the parental strain of the constructs described below. Strain 10403S has an $LD_{50}$ of approximately 5×10⁴ CFU when injected intraperitoneally into BALB/c mice. "Lm-Gag" is a recombinant LM strain containing a copy of the HIV-1 strain HXB (subtype B laboratory strain with a syncytia-forming phenotype) gag gene stably integrated into the *Listerial* chromosome using a modified shuttle vector pKSV7. Gag protein was expressed and secreted by the strain, as determined by Western blot. All strains were grown in brain-heart infusion (BHI) broth or agar plates (Difco Labs, Detroit, Mich.).

Bacterial Culture

Bacteria from a single clone expressing the passenger antigen and/or fusion protein were selected and cultured in BHI broth overnight. Aliquots of this culture were frozen at ⁻70° C. with no additives. From this stock, cultures were grown to 0.1-0.2 O.D. at 600 nm, and aliquots were again frozen at −70° C. with no additives. To prepare cloned bacterial pools, the above procedure was used, but after each passage a number of bacterial clones were selected and checked for expression of the target antigen, as described herein. Clones in which expression of the foreign antigen was confirmed were used for the next passage.

Passage of Bacteria in Mice 6-8 week old female BALB/c (H-2d) mice were purchased from Jackson Laboratories (Bar Harbor, Me.) and were maintained in a pathogen-free microisolator environment. The titer of viable bacteria in an aliquot of stock culture, stored frozen at −70° C., was determined by plating on BHI agar plates on thawing and prior to use. In all, 5×10⁵ bacteria were injected intravenously into BALB/c mice. After 3 days, spleens were harvested, homogenized, and serial dilutions of the spleen homogenate were incubated in BHI broth overnight and plated on BHI agar plates. For further passage, aliquots were again grown to 0.1-0.2 O.D., frozen at −70° C., and bacterial titer was again determined by serial dilution. After the initial passage (passage 0), this sequence was repeated for a total of 4 times.

Intracellular Cytokine Stain for IFN-Gamma

Lymphocytes were cultured for 5 hours in complete RPMI-10 medium supplemented with 50 U/ml human recombinant IL-2 and 1 microliter/ml Brefeldin A (Golgistop™ protein transport inhibitor; PharMingen, San Diego, Calif.) in the presence or absence of either the cytotoxic T-cell (CTL) epitope for HIV-GAG (AMQMLKETI; SEQ ID No: 25), *Listeria* LLO (GYKDGNEYI; SEQ ID No: 26) or the HPV virus gene E7 (RAHYNIVTF; SEQ ID No: 24), at a concentration of 1 micromole. Cells were first surface-stained, then washed and subjected to intracellular cytokine stain using the CYTOFIX/CYTOPERM™ intracellular cytokine staining kit in accordance with the manufacturer's recommendations (PharMingen, San Diego, Calif.). For intracellular IFN-gamma stain, FITC-conjugated rat anti-mouse IFN-gamma monoclonal antibody (clone XMG 1.2) and its isotype control Ab (rat IgG1; both from PharMingen) was used. In all, $10^6$ cells were stained in PBS containing 1% Bovine Serum Albumin and 0.02% sodium azide (FACS Buffer) for 30 minutes at 4° C., followed by 3 washes in FACS buffer. Sample data were acquired on either a FACSCAN™ flow cytometer or FACSCALIBUR™ flow cytometer instrument (Becton Dickinson, San Jose, Calif.). Three-color flow cytometry for CD8 (PERCP conjugated, rat anti-mouse, clone 53-6.7 Pharmingen, San Diego, Calif.), CD62L (APC conjugated, rat anti-mouse, clone MEL-14), and intracellular IFN-gamma was performed using a FACSCALIBUR™ flow cytometer, and data were further analyzed with CELLQUEST® software (Becton Dickinson, Mountain View, Calif.). Cells were gated on CD8 high and $CD62L^{low}$ before they were analyzed for $CD8^+$ and intracellular IFN-gamma staining.

Results

Passaging in Mice Increases the Virulence of Recombinant Listeria Monocytogenes

Three different constructs were used to determine the impact of passaging on recombinant Listeria vaccine vectors. Two of these constructs carry a genomic insertion of the passenger antigen: the first comprises the HIV gag gene (Lm-Gag), and the second comprises the HPV E7 gene (Lm-E7). The third (Lm-LLO-E7) comprises a plasmid with the fusion gene for the passenger antigen (HPV E7) fused with a truncated version of LLO and a gene encoding PrfA, the positive regulatory factor that controls Listeria virulence factors. This plasmid was used to complement a prfA negative mutant so that in a live host, selection pressures would favor conservation of the plasmid, because without it the bacterium is avirulent. All 3 constructs had been propagated extensively in vitro for many bacterial generations.

Figure 7A:
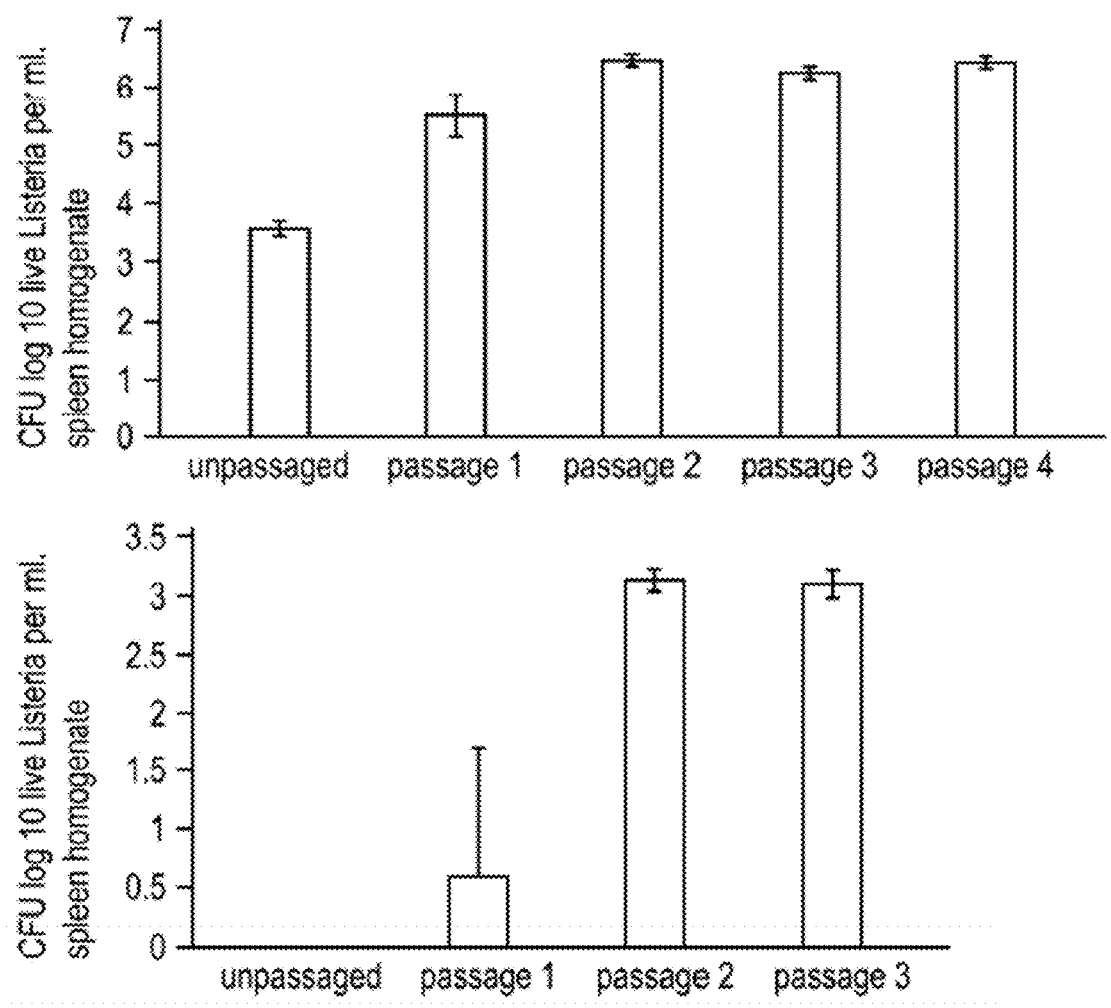
FIG. 7A-B.
Figure 7B:
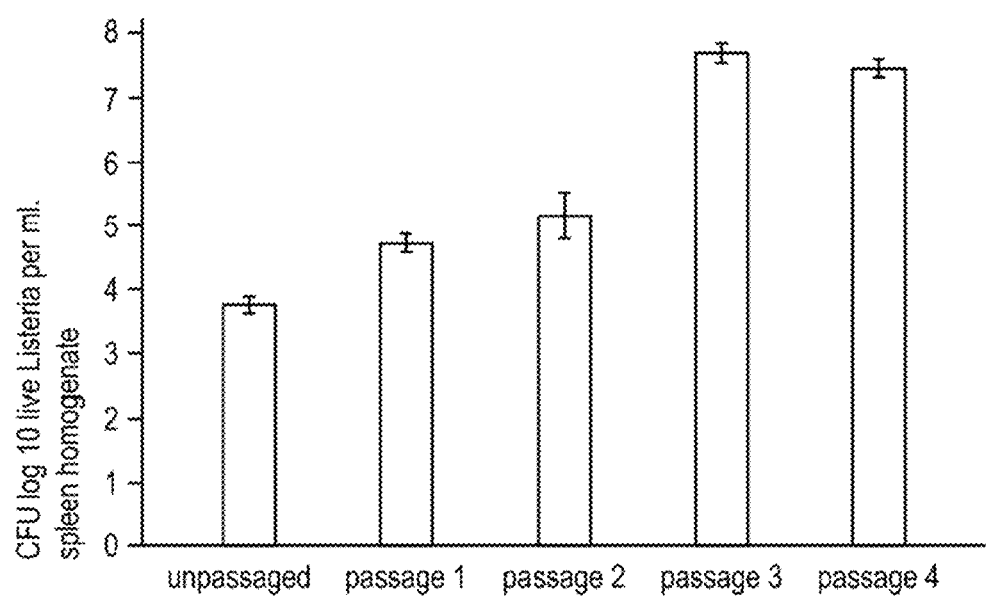
Figure 8A:
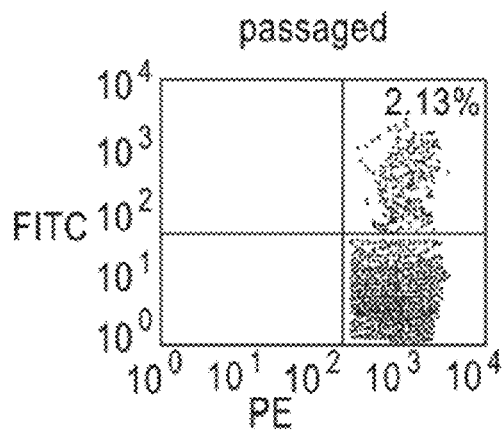
Figure 8B:
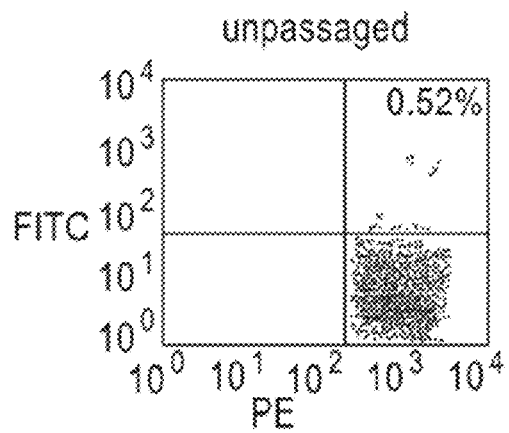
Figure 8C:
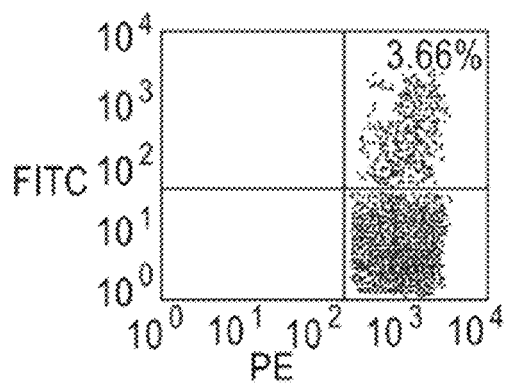
Figure 8D:
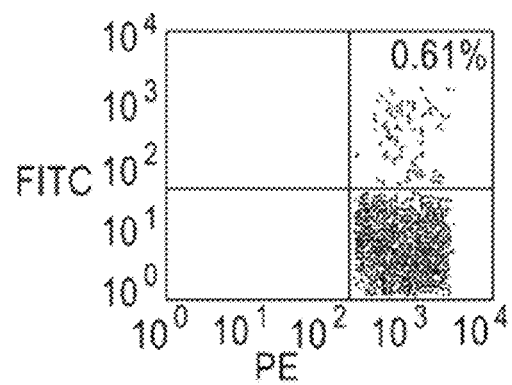
Figure 8E:
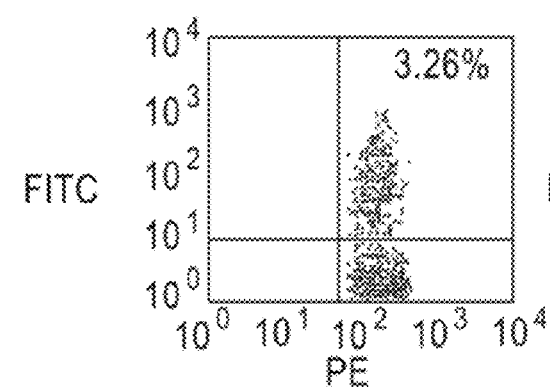
Figure 8F:
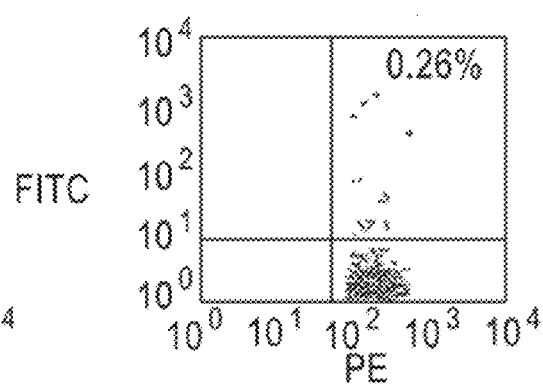

Passaging the bacteria resulted in an increase in bacterial virulence, as measured by numbers of surviving bacteria in the spleen, with each of the first 2 passages. For Lm-Gag and Lm-LLO-E7, virulence increased with each passage up to passage 2 (FIG. 7A). The plasmid-containing construct, Lm-LLO-E7, demonstrated the most dramatic increase in virulence. Prior to passage, the initial immunizing dose of Lm-LLO-E7 had to be increased to $10^7$ bacteria and the spleen had to be harvested on day 2 in order to recover bacteria (whereas an initial dose of $10^5$ bacteria for Lm-Gag was harvested on day 3). After the initial passage, the standard dosage of Lm-LLO-E7 was sufficient to allow harvesting on day 3. For Lm-E7, virulence increased by 1.5 orders of magnitude over unpassaged bacteria (FIG. 7B).

Thus, passage through mice increases the virulence of Listeria vaccine strains.

Passaging Increases the Ability of L. Monocytogenes to Induce $CD8^+$ T Cells

Next, the effect of passaging on induction of antigen-specific $CD8^+$ T cells was determined by intracellular cytokine staining with immunodominant peptides specific for MHC-class I using HIV-Gag peptide AMQMLKETI (SEQ ID No: 25) and LLO 91-99 (GYKDGNEYI; SEQ ID No: 26). Injection of $10^3$ CFU passaged bacteria (Lm-Gag) into mice elicited significant numbers of HIV-Gag-specific $CD8^+$ T cells, while the same dose of non-passaged Lm-Gag induced no detectable Gag-specific $CD8^+$ T cells. Even increasing the dose of unpassaged bacteria 100-fold did not compensate for their relative avirulence; in fact, no detectable Gag-specific $CD8^+$ T cells were elicited even at the higher dose. The same dose increase with passaged bacteria increased Gag-specific T cell induction by 50% (FIG. 8A-I). The same pattern of induction of antigen-specific $CD8^+$ T cells was observed with LLO-specific $CD8^+$ T cells, showing that these results were not caused by the properties of the passenger antigen, since they were observed with LLO, an endogenous Listeria antigen.

Thus, passage through mice increases the immunogenicity of Listeria vaccine strains.

Example 5: a PrfA-Containing Plasmid is Stable in an LM Strain with a PrfA Deletion in the Absence of Antibiotics

MATERIALS AND EXPERIMENTAL METHODS

Bacteria

L. monocytogenes strain XFL7 contains a 300 base pair deletion in the prfA gene XFL7 carries pGG55 which partially restores virulence and confers CAP resistance, and is described in United States Patent Application Publication No. 200500118184.

Development of Protocol for Plasmid Extraction from Listeria 1 mL of Listeria monocytogenes Lm-LLO-E7 research working cell bank vial was inoculated into 27 mL BH1 medium containing 34 µg/mL CAP and grown for 24 hours at 37° C. and 200 rpm.

Seven 2.5 mL samples of the culture were pelleted (15000 rpm for 5 minutes), and pellets were incubated at 37° C. with 50 µl lysozyme solution for varying amounts of time, from 0-60 minutes.

Lysozyme Solution:

29 µl 1 M dibasic Potassium Phosphate
21 µl 1 M monobasic Potassium Phosphate
500 µl 40% Sucrose (filter sterilized through 0.45/µm filter)
450 µl water
60 µl lysozyme (50 mg/mL)

After incubation with the lysozyme, the suspensions were centrifuged as before and the supernatants discarded. Each pellet was then subjected to plasmid extraction by a modified version of the QIAPREP® Spin Miniprep Kit™ (Qiagen, Germantown, Md.) plasmid miniprep kit protocol. The changes to the protocol were as follows:
1. The volumes of buffers PI, P2 and N3 were all increased threefold to allow complete lysis of the increased biomass.
2. 2 mg/mL of lysozyme was added to the resuspended cells before the addition of P2. The lysis solution was then incubated at 37° C. for 15 minutes before neutralization.
3. The plasmid DNA was resuspended in 30 µL rather than 50 µL to increase the concentration.

In other experiments, the cells were incubated for 15 min in P1 buffer+Lysozyme, then incubated with P2 (lysis buffer) and P3 (neutralization buffer) at room temperature.

Equal volumes of the isolated plasmid DNA from each subculture were run on a 0.8% agarose gel stained with ethidium bromide and visualized for any signs of structural or segregation instability.

The results showed that plasmid extraction from L. monocytogenes Lm-LLO-E7 increases in efficiency with increasing incubation time with lysozyme, up to an optimum level at approximately 50 minutes incubation.

These results provide an effective method for plasmid extraction from Listeria vaccine strains.

Replica Plating

Dilutions of the original culture were plated onto plates containing LB or TB agar in the absence or presence of 34 µg/mL CAP. The differences between the counts on selective and non-selective agar were used to determine whether there was any gross segregational instability of the plasmid.

Results

Figure 9C:
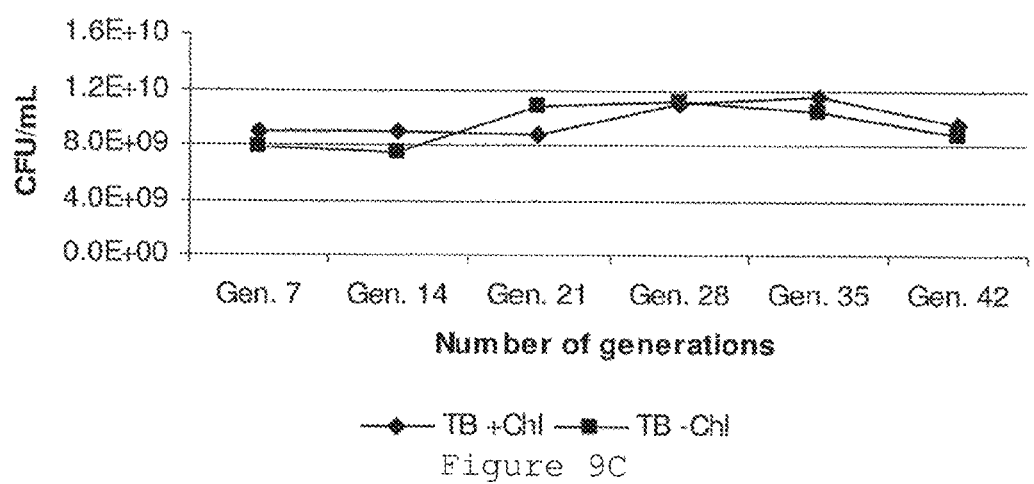
FIG. 9C shows quantitation of TB stability study.

The genetic stability (i.e. the extent to which the plasmid is retained by or remains stably associated with the bacteria in the absence of selection pressure; e.g. antibiotic selection pressure) of the pGG55 plasmid in L. monocytogenes strain XFL7 in the absence of antibiotic was assessed by serial sub-culture in both Luria-Bertani media (LB: 5 g/L NaCl, 10 g/ml soy peptone, 5 g/L yeast extract) and Terrific Broth media (TB: 10 g/L glucose, 11.8 g/L soy peptone, 23.6 g/L yeast extract, 2.2 g/L $KH_2PO_4$, 9.4 g/L $K_2HPO_4$), in duplicate cultures. 50 mL of fresh media in a 250 mL baffled shake flask was inoculated with a fixed number of cells (1 ODmL), which was then subcultured at 24 hour intervals. Cultures were incubated in an orbital shaker at 37° C. and 200 rpm. At each subculture the $OD_{600}$ was measured and used to calculate the cell doubling time (or generation) elapsed, until 30 generations were reached in LB and 42 in TB. A known number of cells (15 ODmL) at each subculture stage (approximately every 4 generations) were pelleted by centrifugation, and the plasmid DNA was extracted using the Qiagen QIAPREP® Spin Miniprep Kit™ plasmid miniprep kit protocol described above. After purification, plasmid DNA was subjected to agarose gel electrophoresis, followed by ethidium bromide staining. While the amount of plasmid in the preps varied slightly between samples, the overall trend was a constant amount of plasmid with respect to the generational number of the bacteria (FIGS. 9A-B). Thus, pGG55 exhibited stability in strain XFL7, even in the absence of antibiotic.

Figure 10:
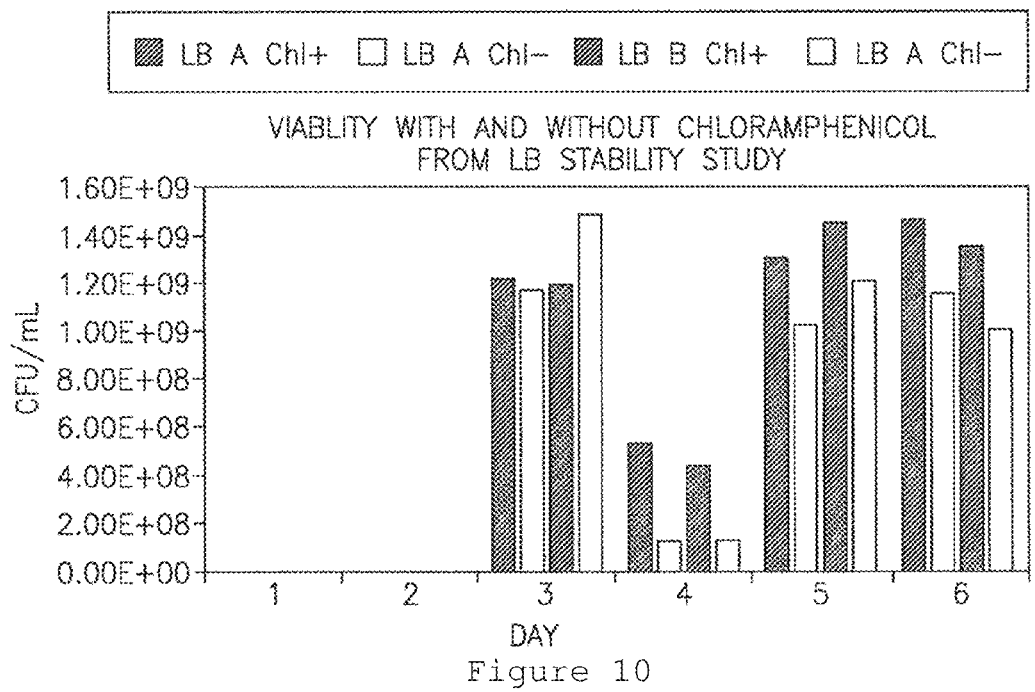
FIG. 10 shows numbers of viable bacteria chloramphenicol (CAP)-resistant and CAP-sensitive colony-forming units (CFU) from bacteria grown in LB. Dark bars: $CAP^+$; white bars: $CAP^-$. The two dark bars and two white bars for each time point represent duplicate samples.
Figure 11:
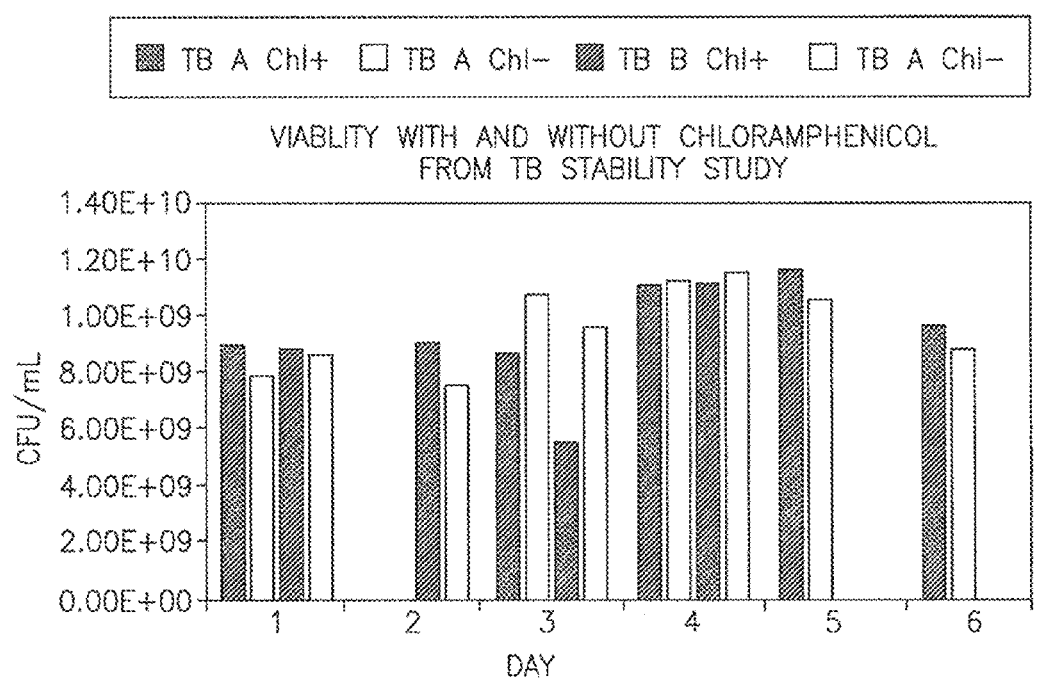
FIG. 11 shows numbers of viable bacteria CAP-resistant and CAP-sensitive CFU from bacteria grown in TB. Dark bars: $CAP^+$; white bars: CAP. The two dark bars and two white bars for each time point represent duplicate samples.

Plasmid stability was also monitored during the stability study by replica plating on agar plates at each stage of the subculture. Consistent with the results from the agarose gel electrophoresis, there was no overall change in the number of plasmid-containing cells throughout the study in either LB or TB liquid culture (FIGS. 10 and 11, respectively).

These findings demonstrate that PrfA-encoding plasmids exhibit stability in the absence of antibiotic in Listeria strains containing mutations in prfA.

Materials and Methods (Examples 6-10)

PCR Reagents:

The primers used for amplification of the prfA gene and discrimination of the D133V mutation are shown in Table 1. Stock solutions of the primers ADV451, 452 and 453 were prepared by diluting the primers in TE buffer to 400 µM. An aliquot of the stock solution was further diluted to 20 µM in water (PCR grade) to prepare a working solution. Primers were stored at −20° C. The reagents used in the PCR are shown in Table 2.

TABLE 1

Primers ADV451, 452 and 453.

| Primer | Orientation | Sequence (5'→3') | Specificity |
|---|---|---|---|
| ADV451 | Forward | CCTAGCTAAATTTAATGT (SEQ ID NO: 28) | D133V mutation |
| ADV452 | Forward | CCTAGCTAAATTTAATGA (SEQ ID NO: 29) | Wild-type sequence |
| ADV453 | Reverse | TAATTTTCCCCAAGTAGCAGG (SEQ ID NO: 30) | Shared sequence |

TABLE 2

PCR reagents.

| | Description | Provider | Catalog number |
|---|---|---|---|
| 1 | 0.2 ml thin-walled PCR tubes: GeneAmp autoclaved reaction tube with cap | Applied Biosystems | N801-0612 |
| 2 | Water (PCR reagent) | Sigma | W1754 |
| 3 | Taq DNA Polymerase with 10x reaction buffer containing 15 mM $MgCl_2$ | Sigma | D1806 |
| 4 | Set of deoxynucleotides (dNTPs), 10 mM each | Sigma | D7295 |
| 5 | Primers ADV451, ADV452 and ADV453 | Invitrogen | |
| 6 | Template DNA, midipreparations of pGG55 plasmids | | |
| 7 | Thermal cycler PTC200 (48 wells block) | MJ Research | |

Plasmid DNA PREPARATION pGG55 plasmids with (pGG55 D133V) and without (pGG55 WT) the prfA mutation were extracted and purified by midipreparations either from E. coli or Listeria monocytogenes using the PureLink™ HiPure Plasmid Midiprep Kit (Invitrogen, K2100-05), according to the manufacturer's instructions. For plasmid purification from Listeria, bacterial strains carrying the pGG55 D133V or WT plasmids were streak plated from frozen stocks in BHI agar plates supplemented with chloramphenicol (25 µg/ml). A single colony from each strain was grown in 5 ml of selective medium (BHI broth with 25 µg/ml of chloramphenicol) for 6 hours with vigorous shaking at 37° C. and subinoculated 1:500 in 100 ml of selective medium for overnight growth under similar conditions. Bacteria from the overnight culture were harvested by centrifugation at 4,000×g for 10 minutes and resuspended buffer R3 (resuspension buffer) containing 2 mg/ml of lysozyme (Sigma, L7001). The bacteria suspension was incubated for at least 1 hour at 37° C. before proceeding to the regular protocol. Concentration and purity of the eluted plasmids were measured in a spectrophotometer at 260 nm and 280 nm. To prepare the template DNAs, the pGG55 D133V and WT plasmids were resuspended in water to a final concentration of 1 ng/µl from the midiprep stock solution. For the pGG55 WT plasmid, serial 10-fold dilutions from the 1 ng/µl solution were prepared, corresponding to dilutions from $10^{-1}$ to $10^{-7}$.

prfA Specific PCR Protocol to Test Clinical Grade Material

The reaction mixture contained 1×PCR buffer, 1.5 mM $MgCl_2$, 0.8 mM dNTPs, 0.4 µM of each primer, 0.05 U/µl of Taq DNA polymerase and 0.04 ng/µl of the pGG55 D133V template plasmid. For each test, 10 tubes were required and the key components in each tube in a 25 µl reaction are shown in the Table 3. For the PCR reaction, a master mix was prepared with enough reagents for 11 reactions as shown in Table 4, and 24 µl of this PCR mix was added to each tube. Subsequently, a total of 1 µl of the serially diluted pGG55 WT plasmid was added to the corresponding tubes: 1 ng in tube 3; 100 pg in tube 4; 10 pg in tube 5; 1 pg in tube 6; 100 fg in tube 7; 10 fg in tube 8; 1 fg in tube 9; 0.1 fg in tube 10. This serial dilution was used to calibrate a standard curve to determine the method sensitivity. Additionally, 0.5 µl of water and 0.5 µl of primer ADV451 (20 µM stock) were added in tube 1, and 1 µl of water added in tube 2, completing 25 µl of final volume. The quantities of each reagent per tube for a 25 µl reaction are shown in Table 5. The PCR cycling conditions used in the reaction are shown in Table 6.

After conclusion of the PCR reaction, 5 µl of gel-loading buffer (6×, with bromophenol blue) was added to each sample and 10 µl were analyzed by electrophoresis in 1.2% agarose gel in TBE buffer. The gel dimensions were 7 cm×7 cm×1 cm with a 15 sample wells (1 mm×2 mm) comb. The gel was run at 100 V for ~30 minutes, until the bromophenol blue dye reached the middle of the gel. The gel was stained in ethidium bromide (0.5 µg/ml) for 20 minutes, destaining in water for 10 minutes. The gel is visualized by illumination with UV light and photographed. The image was analyzed using a band densitometry software (Quantity One version 4.5.1, BioRad).

TABLE 3

Set of individual PCR reactions to validate the method to detect the presence of wild-type prfA sequence in Lm-LLO-E7 samples.

| Tube | Primer A | Primer B | Template DNA | Function | Expected result |
|---|---|---|---|---|---|
| 1 | ADV451 | ADV453 | 1 ng of pGG55 (D133V) | Positive control for the ADV451 reaction | Positive |
| 2 | ADV452 | ADV453 | 1 ng of pGG55 (D133V) | Negative control for the ADV452 reaction (specificity) | Negative |
| 3 | ADV452 | ADV453 | 1 ng of pGG55 (wild-type) + 1 ng of pGG55 (D133V) | Positive control for the ADV452 reaction | Positive |
| 4 | ADV452 | ADV453 | 100 pg of pGG55 (wild-type) + 1 ng of pGG55 (D133V) | Test the sensitivity of the reaction | Positive |
| 5 | ADV452 | ADV453 | 10 pg of pGG55 (wild-type) + 1 ng of pGG55 (D133V) | Test the sensitivity of the reaction | Positive |
| 6 | ADV452 | ADV453 | 1 pg of pGG55 (wild-type) + 1 ng of pGG55 (D133V) | Test the sensitivity of the reaction | Positive |
| 7 | ADV452 | ADV453 | 100 fg of pGG55 (wild-type) + 1 ng pGG55 (D133V) | Test the sensitivity of the reaction | Positive |
| 8 | ADV452 | ADV453 | 10 fg of pGG55 (wild-type) + pGG55 (D133V) | Test the sensitivity of the reaction | Positive |
| 9 | ADV452 | ADV453 | 1 fg of pGG55 (wild-type) + pGG55 (D133V) | Test the sensitivity of the reaction | Weakly positive |
| 10 | ADV452 | ADV453 | 0.1 fg of pGG55 (wild-type) + pGG55 (D133V) | Test the sensitivity of the reaction | To be determined |

TABLE 4

Master PCR mix preparation.

| Reagent | Quantity (µl) |
|---|---|
| Water | 206.25 |
| Taq DNA Polymerase 10x reaction buffer containing 15 mM $MgCl_2$ | 27.5 |
| Deoxynucleotides (dNTPs) 10 mM each | 5.5 |
| Primers ADV452 (20 µM in water) | 5.5 |
| Primers ADV453 (20 µM in water) | 5.5 |
| pGG55 D133V (Lm-LLO-E7) plasmid (1 ng/µl) | 11 |
| Taq DNA Polymerase (5 U/µl) | 2.75 |
| Total | 264 |

TABLE 5

PCR protocol for validation of the method to detect the presence of wild-type prfA sequence using primers ADV451, 452 and 453.

| Reagent | PCR |
|---|---|
| Water | 18.75 µl |
| PCR Buffer 10x + $MgCl_2$ 15 mM | 2.5 µl |

TABLE 5-continued

PCR protocol for validation of the method to detect the presence of wild-type prfA sequence using primers ADV451, 452 and 453.

| Reagent | PCR |
|---|---|
| Deoxynucleotides mix (dATP, dCTP, dGTP and dTTP) 10 mM each | 0.5 µl |
| Primer ADV452 (20 µM) | 0.5 µl |
| Primer ADV453 (20 µM) | 0.5 µl |
| Taq DNA polymerase (5 U/µl) | 0.25 µl |
| Template DNA (1 ng/µl) pGG55 D133V | 1 µl |
| Template DNA pGG55 WT (tubes 3 to 10)[a] | 1 µl |
| Final volume per tube[b] | 25 µl |

[a]pGG55 WT (1 ng in tube 3; 100 pg in tube 4; 10 pg in tube 5; 1 pg in tube 6; 100 fg in tube 7; 10 fg in tube 8; 1 fg in tube 9; 0.1 fg in tube 10).
[b]In tube 1, add 0.5 µl of water and 0.5 µl of primer ADV451 (20 µM stock); in tube 2 add 1 µl of water.

TABLE 6

PCR cycling conditions to detect the presence of wild-type prfA sequence using primers ADV451, 452 and 453.

| Step | Temperature | Time | Number of cycles |
|---|---|---|---|
| 1. | 94° C. | 2 minutes and 30 seconds | 1 |
| 2. | 94° C. | 30 seconds | 1 |
| 3. | 53° C. | 30 seconds | 1 |
| 4. | 72° C. | 30 seconds | 1 |
| 5. | | Repeat steps 2 to 4 | 12 |
| 6. | 94° C. | 30 seconds | 1 |
| 7. | 50° C. | 30 seconds | 1 |
| 8. | 72° C. | 30 seconds | 1 |
| 9. | | Repeat steps 6 to 8 | 23 |
| 10. | 72° C. | 10 minutes | 1 |

Sequencing:

Sequencing of the plasmids was done using the dideoxy sequencing method. The plasmids pGG55 D133V and pGG55 WT were mixed at different ratios (1:1, 1:10, 1:100, 1:1,000 and 1:10,000). The total amount of plasmid in the mixture was kept constant (500 µg) and the plasmid containing the wild-type sequence was 10-fold serially diluted in relation to the D133V plasmid to determine the sensitivity of the method.

Results

Figure 12A:
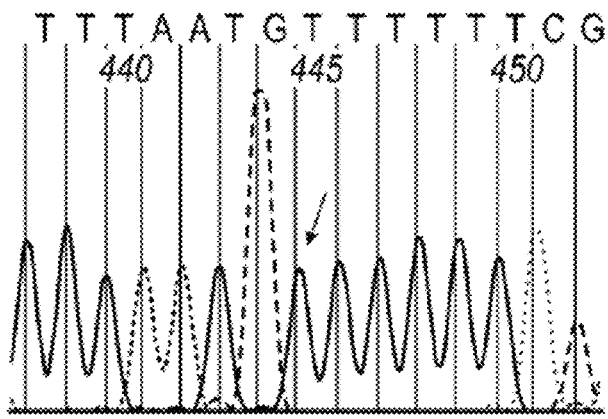
FIG. 12A. pGG55 D133V+pGG55 WT (1:0).
Figure 12B:
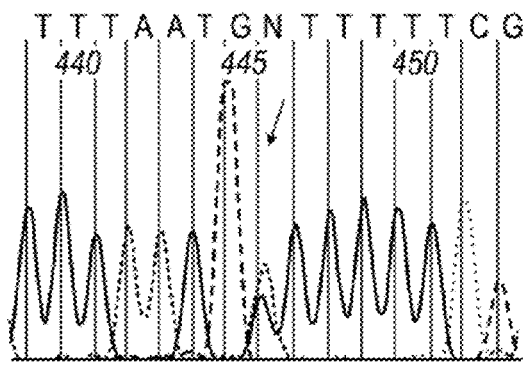
FIG. 12B. pGG55 D133V+pGG55 WT (1:1). Two peaks are clearly visible and indicated by the arrow when plasmids are mixed in equimolar amounts.
Figure 12C:
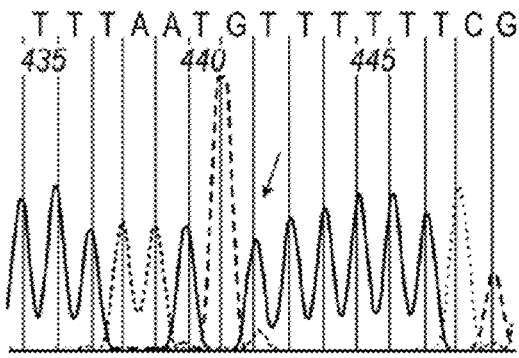
FIG. 12C. pGG55 D133V+ pGG55 WT (10:1). 1 in 10 is the maximum limit of detection and the peak from the wild-type sequence is still clearly detectable.
Figure 12D:
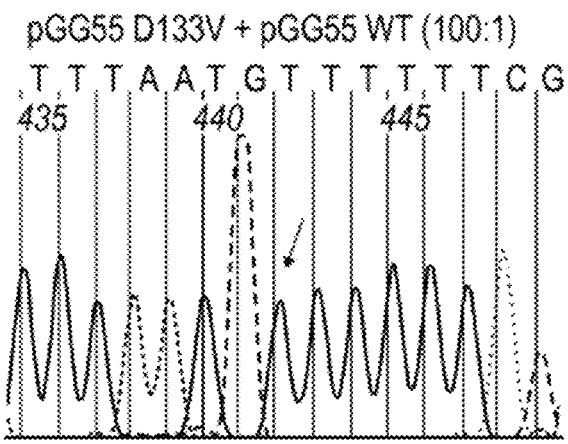
FIG. 12D. pGG55 D133V+pGG55 WT (100:1). The peak from the wild-type sequence has disappeared completely when the wild-type prfA plasmid is diluted 1 to 100 or more.
Figure 12E:
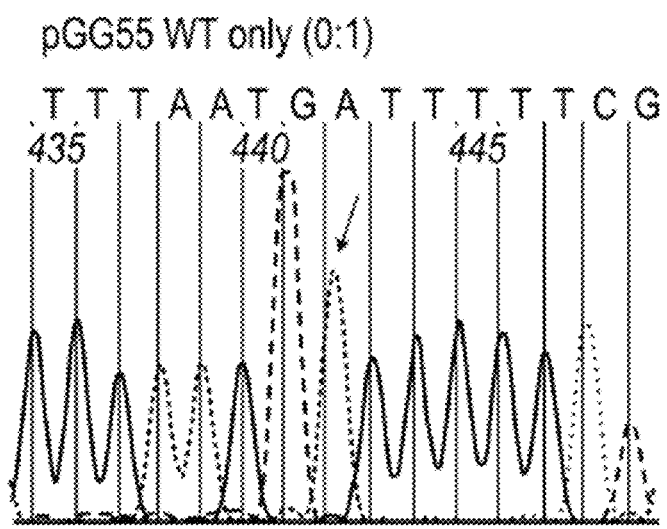
FIG. 12E. pGG55 WT only (0:1).

Example 6: Sequencing is not a Sensitive Method to Detect the Reversion of the D133V Mutation To estimate the sensitivity of sequencing in detecting the wild-type prfA sequence, the pGG55 D133V and WT plasmids were mixed at the different ratios and sequenced. The results are shown in FIG. 12 and reveal that sequencing has a high specificity in discriminating the prfA D133V mutation (FIG. 12A-E). On the other hand, the sensitivity is low and the maximum dilution of wild-type prfA pGG55 plasmid with a detectable peak in the sequence was 1 in 10 (FIG. 12C). In conclusion, although sequencing is very specific, the sensitivity of the method is low and not appropriate to screen for the presence of rare events such as revertants of the prfA D133V mutation in Lm-LLO-E7 samples.

Example 7: Development of a Highly Specific and Sensitive PCR Method to Detect Reversion of the D133V Mutation Given the low sensitivity of sequencing to detect rare events, it became imperative to develop a more sensitive method with similar specificity to detect reversion of the D133V mutation to wild-type. To achieve this goal, we designed a PCR-based method that specifically amplifies the wild-type sequence and is sensitive enough to detect at least 1 wild-type copy of prfA in 10,000,000 copies of the D133V mutated sequence. We designed 3 primers for this method: ADV451, ADV452 and ADV453 (Table 1). Both ADV451 and ADV452 are forward primers and differ in the last nucleotide at the 3' position to discriminate the A→T (D133V) mutation at position 398 of the prfA gene. The ADV453 primer is the reverse primer located approximately 300 bp downstream the annealing site of the ADV451 and ADV452 primers (FIG. 13). The expected PCR band obtained with the primers ADV451 or ADV452 and ADV453 is 326 bp. Under stringent conditions, the ADV451 primer should only amplify the pGG55 D133V plasmid, whereas the ADV452 would be specific to the wild-type prfA sequence.

Example 8: Specificity of the PCR Method

Figure 14:
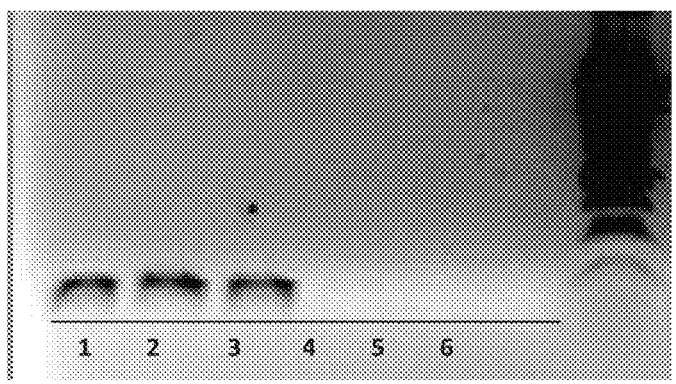
FIG. 14. Specificity of the PCR reaction using primers ADV451 and ADV453.

The reaction using the primer ADV451 was very specific and amplified the mutated D133V prfA sequence (lanes 1 to 3), but not the wild-type sequence (lanes 4 to 6). However, a very faint band can be detected in lane 4, when 5 ng of template DNA was used, but not with 1 ng (FIG. 14).

Figure 15:
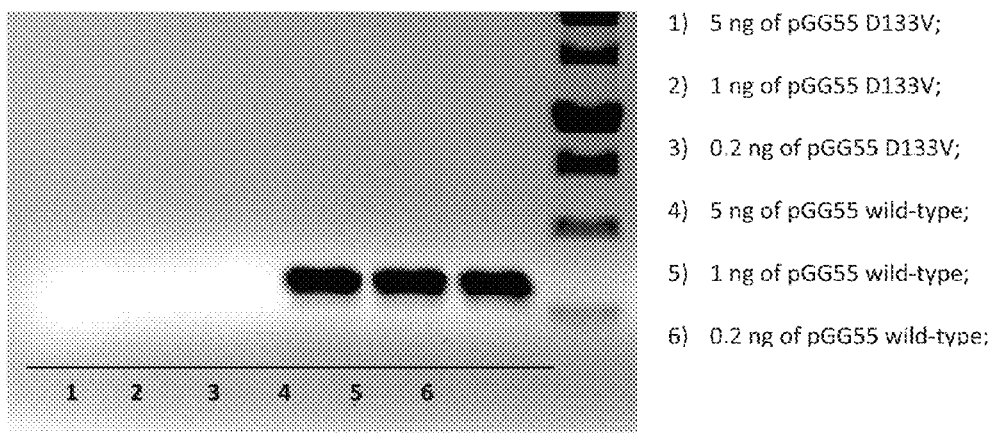
FIG. 15. Specificity of the PCR reaction using primers ADV452 and ADV453.
Figure 16:
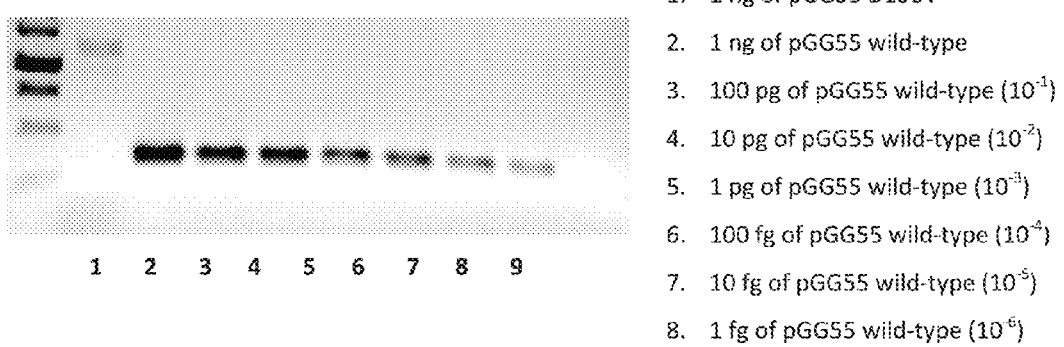
FIG. 16. Sensitivity of the PCR reaction to detect the wild-type prfA sequence using the primer ADV452 and 1 ng as the initial amount of DNA.

As shown in FIG. 15, the reaction with the ADV452 primer only amplified the wild-type prfA sequence (lanes 4, 5 and 6), and no bands were detected when the pGG55 carrying the D133V PrfA mutation was used as a template (lanes 1, 2 and 3), even when using 5 ng of plasmid in the reaction (FIG. 16). In conclusion, the PCR reactions with primers ADV451 and ADV452 are very specific and able to discriminate the A↔T (D133V) mutation at position 398 of the prfA gene in the pGG55 plasmid. Based on these results, we selected the amount of 1 ng as the standard amount of template DNA to be used in the reaction.

Example 9: Sensitivity of the PCR Method

Figure 17:
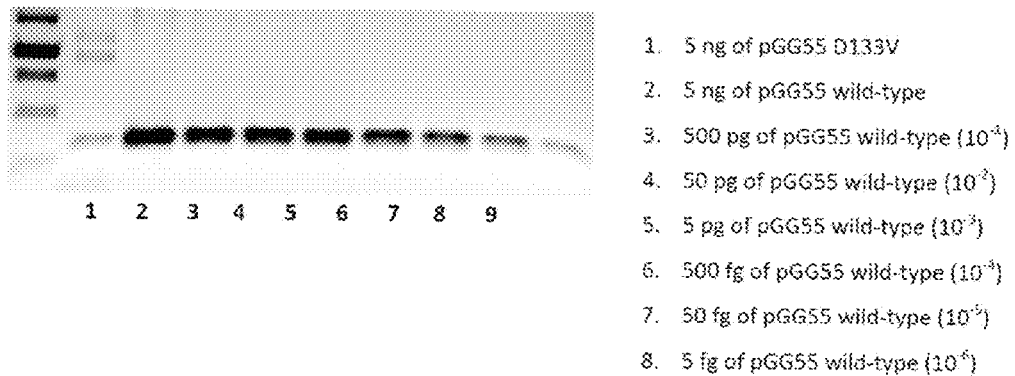
FIG. 17. Sensitivity of the PCR reaction to detect the wild-type prfA sequence using the primer ADV452 and 5 ng as the initial amount of DNA.
Figure 18:
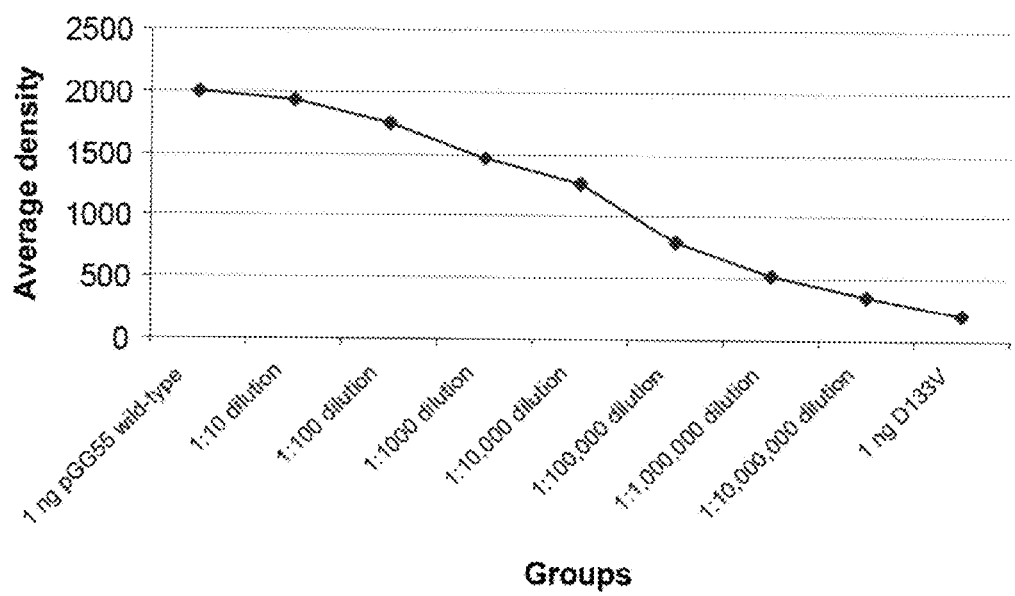
FIG. 18. Average density of the bands from the PCR depicted in FIG. 16.
Figure 19:
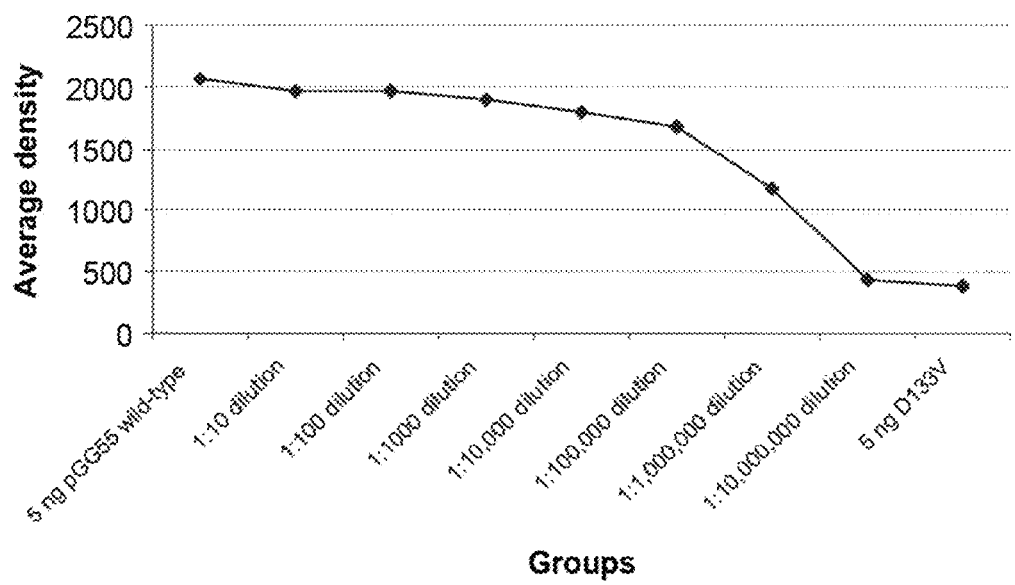
FIG. 19. Average density of the bands from the PCR depicted in FIG. 17.
Figure 20:
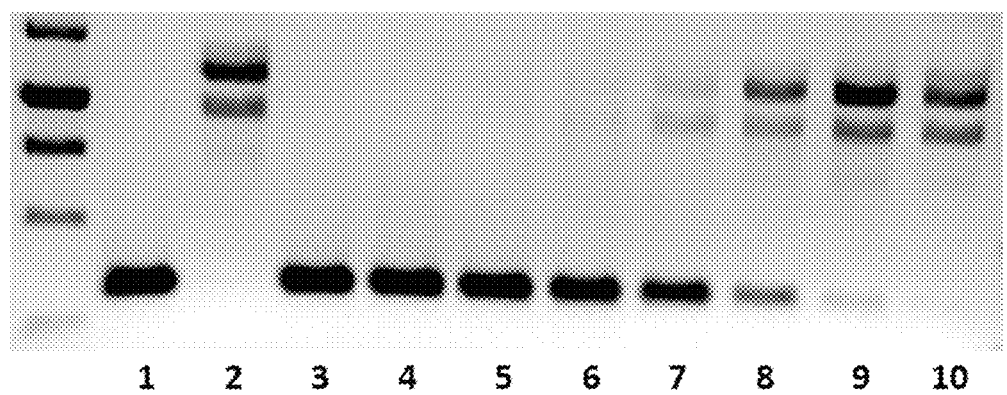
FIG. 20. Validation of the PCR reaction to detect the wild-type prfA sequence using the primer ADV452.
Figure 21:
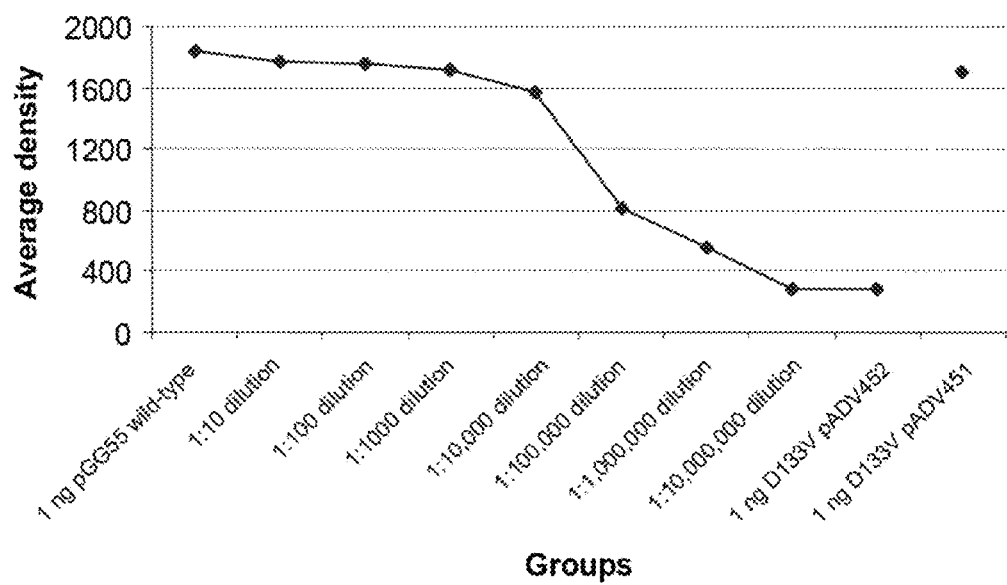
FIG. 21. Average density of the bands from the PCR depicted in FIG. 16.

The sensitivity of the reaction was tested using 1 ng of template DNA. For the plasmid carrying the wild-type prfA sequence, decreasing amounts of DNA (corresponding to 10-fold dilutions from $10^{-1}$ to $10^{-7}$), were also included in the reaction to estimate the sensitivity. In these reactions only the primers ADV452 and ADV453 were used. In a PCR reaction with 30 cycles (10 cycles with annealing temperature of 53° C. and an additional 20 cycles with annealing temperature of 50° C.), the sensitivity of the method was 1 in 100,000 (data not shown). As shown in FIG. 16, increasing the number of PCR cycles to 37 improved the visual sensitivity of the method to $10^{-6}$ for the detection of D133V revertants, without significantly compromising the specificity. A clear band was visible at the $10^{-6}$ dilution, corresponding to a detection level of 1 copy of the wild-type sequence in a million of the D133V mutant, when 1 ng of plasmid was used as the initial amount of DNA. Only a very weak band can be visualized in lanes 1 and 9 after longer exposure, reassuring the robust specificity of the method. On the other hand, when starting with 5 ng of DNA, a band could be easily detected at the $10^{-7}$ dilution, increasing the sensitivity of the PCR. However, a similar band in intensity could also be detected with the pGG55 D133V plasmid, indicating the specificity limit of the method (FIG. 17). This band observed with the pGG55 D133V plasmid is likely due to non-specific amplification of the D133V mutation with primer ADV452 that can significantly accumulate with the increased number of cycles. These results indicate that the sensitivity limit for this method, without significantly compromising the specificity, is situated between 1 to 1,000,000 and 1 to 10,000,000 (See FIGS. 18-21).

Example 10: Recombinant *Listeria* Expressing a Fusion Protein of LLO to E7(Lm-LLO-E7)

Figure 22A:
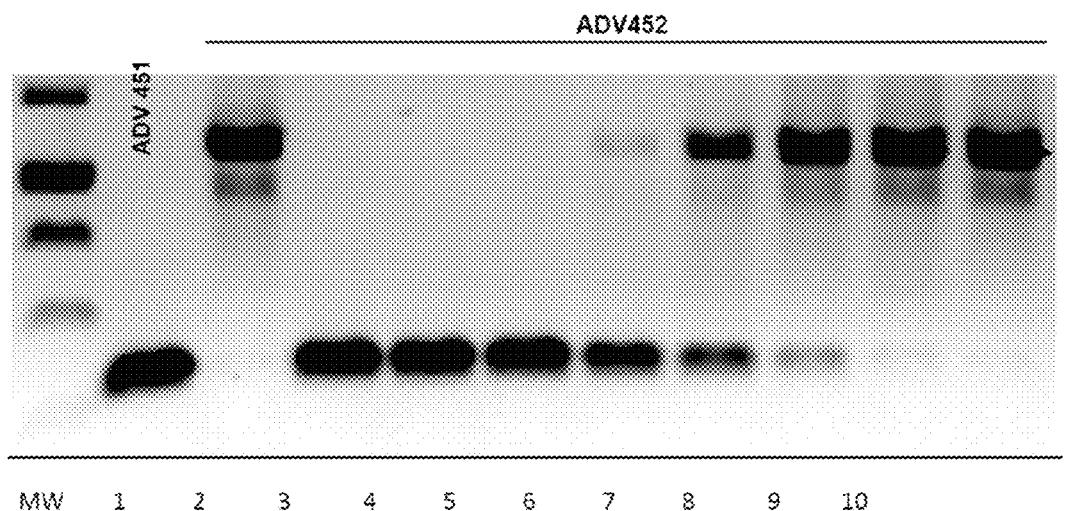
FIG. 22A-B. Analysis of the D133V PrfA mutation in the Lm-LLO-E7.
Figure 22B:
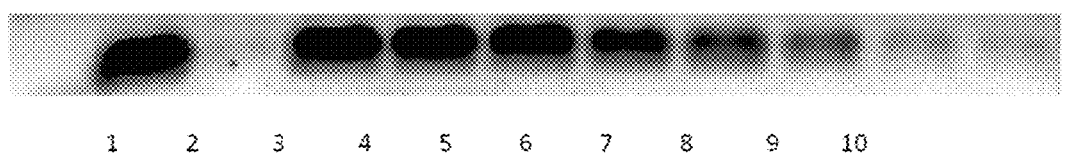

This strain is approx. 4-5 logs more attenuated than the wild-type parent strain 10403S and secretes the fusion protein tLLO-E7. This immunotherapy is based on the backbone XFL7, which is derived from 10403S by the irreversible deletion in the virulence gene transcription activator prfA. PrfA regulates the transcription of several virulence genes such as Listeriolysin 0 (LLO), ActA, PlcA (phospholipase A), PlcB (phospholipase B) etc. that are required for in vivo intracellular growth and survival of *L. monocytogenes*. The plasmid pGG55 is retained by the Lm-LLO-E7 in vitro by means of selection with 'chloramphenicol'. However for in vivo retention of the plasmid by Lm-LLO-E7, it carries a copy of mutated prfA (D133V) (FIG. 22A-B), which has been demonstrated to be less active than wild-type PrfA in DNA binding and activating the transcription of virulence genes. We have observed that complementation with mutated PrfA resulted in approx. 40 fold reduction in the amount of secreted LLO from Lm-LLO-E7 when compared to wild-type strain 10403S. This implicates that possibly the strain Lm-LLO-E7 exhibits a reduced expression of the virulence genes that are regulated by PrfA such as actA, inlA, inlB, inlC, plcB etc. In Lm-LLO-E7, the complementation with mutated copy of prfA possibly causes a reduction in the expression of different virulence genes that are regulated by PrfA resulting in overall attenuation of approx. 4-5 logs.

Example 11: Anti-E7 Tumor Response

Figure 23:
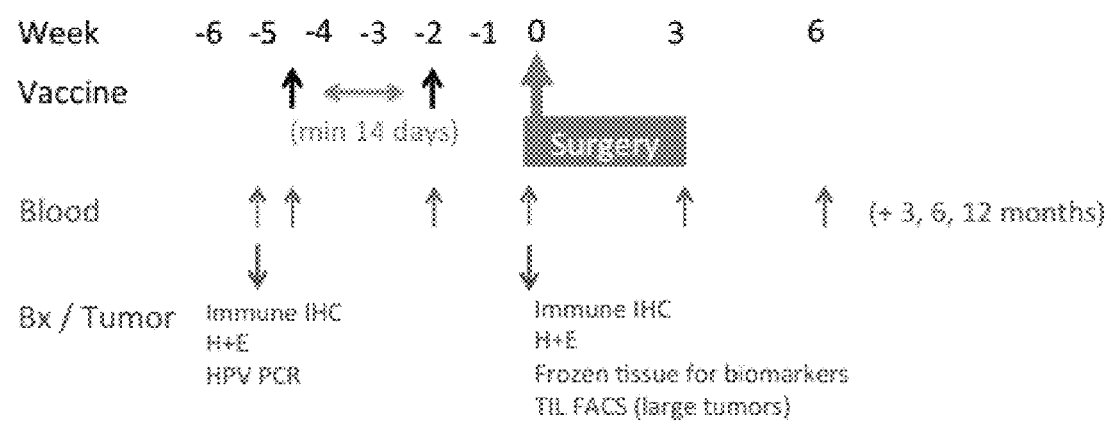
FIG. 23. Shows the trial scheme for administration of the Lm-LLO-E7 vaccine (ADXS-HPV), for sample (tumor tissue or blood) collection, and for carrying out the various assays.
Figure 24:
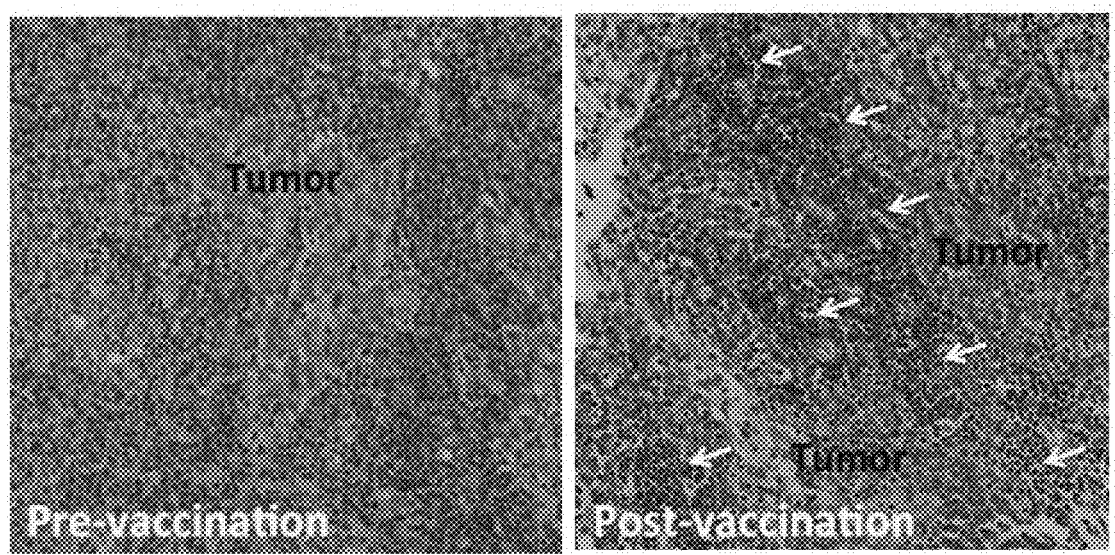
FIG. 24. Hematoxylin and eosin (H&E) stain of tumor samples showing nests of basophilic lymphoid infiltrates (white arrows).
Figure 25:
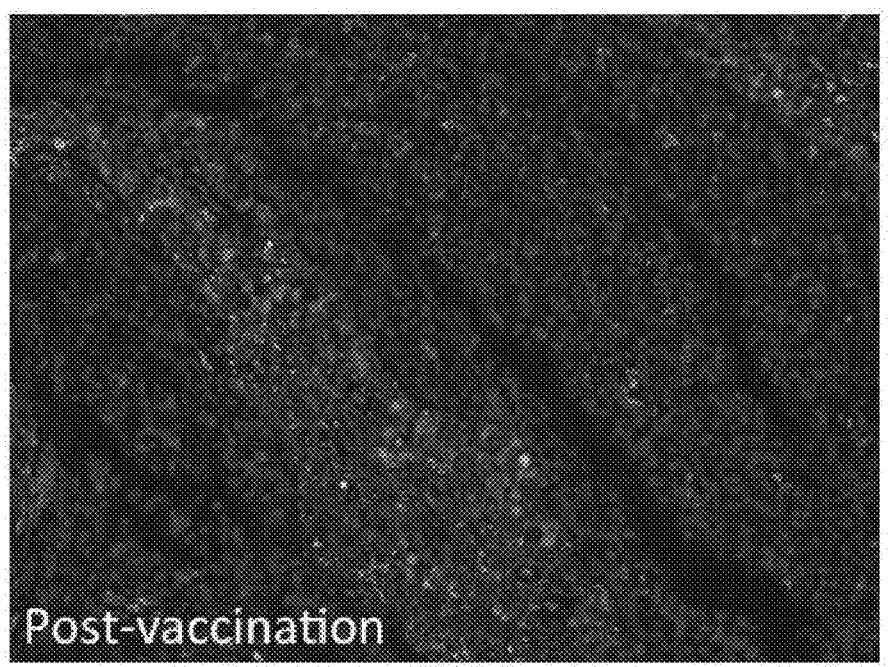
FIG. 25. Multiplex immunofluorescence of tumor sample post-vaccination with ADXS-HPV showing dense intratumoral CD8 infiltrate, and stromal CD4 infiltrate. Green=CD4, Pink=CD8, Purple=CD68, Yellow=CD20.

Recruitment
6 patients with stage II-IV HPVOPC enrolled
5 patients treated with ADXS-HPV
5 patients pre- and initial post-vaccine tumor and blood samples collected.
Assays
Tissue Assays Carried Out Pre- and Post-Vaccine Administration
  H&E histopathology
  Multiplex immunofluorescence
  Nanostring analysis of gene expression signatures
  Blood
  Immunophenotyping by flow cytometry
  HPV antigen-specific T cell responses
  HPV serology
  Cancer-testis antigen serology Results Human tumor tissue samples were obtained from 5 patients prior to and following vaccination with Lm-LLO-E7 (ADXS-HPV). For trial scheme see FIG. 23. Results show nets of basophilic lymphoid infiltrate (see FIG. 24), and dense intratumoral CD8 infiltrate and stromal CD4 infiltrate (FIG. 25).

Figure 26:
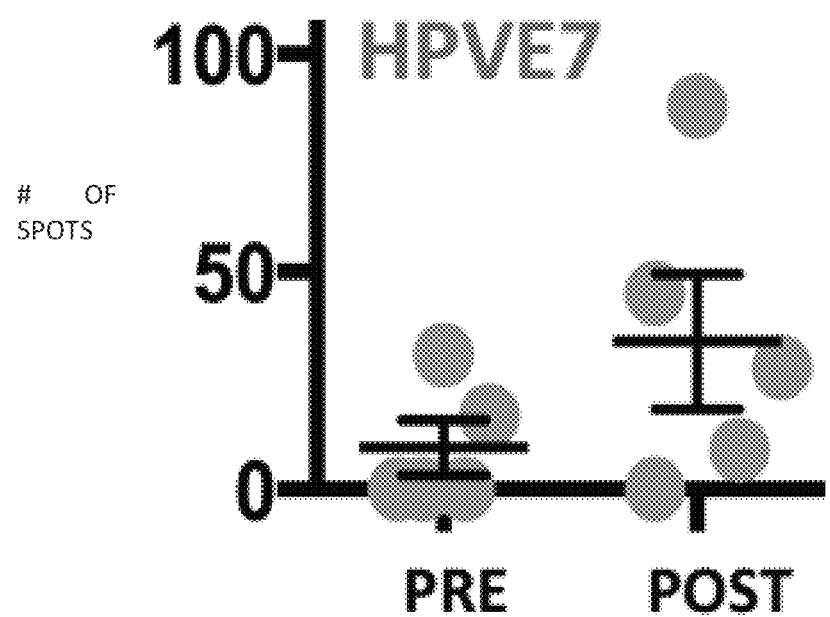
FIG. 26. ELISPOT—Direct analysis (without restimulation and culture) showing that there's a >3-fold increase in HPV-E7 response post vaccination with ADXS-HPV.
Figure 27:
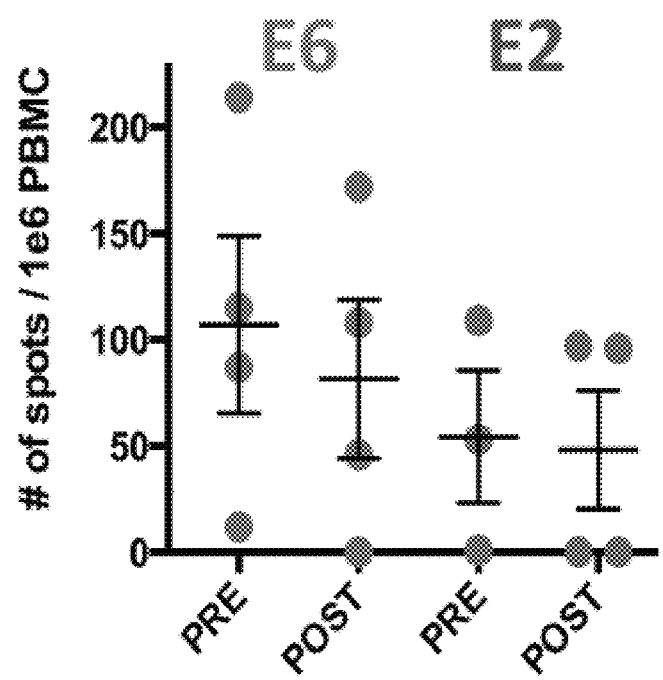
FIG. 27. ELISPOT—Direct analysis (without restimulation and culture) showing that there is no post-vaccination increase in response with non-vaccine antigens HPV-E6 and HPV-E2.

Human blood samples were obtained from 5 patients prior to and following vaccination with Lm-LLO-E7 (ADXS-HPV) and ELISPOT-direct analysis assays (without restimulation and culture) were carried out. An >3-fold mean increase in HPV-E7 response was observed post-vaccination, and increased responses were observed in 3/5 patients (FIG. 26). In contrast, there was no post-vaccine treatment increase in response against non-vaccine antigens (HPV-E6, and E2) demonstrating that the HPV-E7 response was antigen specific (FIG. 27).

Example 12: Phase II Clinical Study of ADXS-HPV Tumor Response

Recruitment and Treatment
11 patients with stage II-IV HPVOPC enrolled
8 patients treated with 1×10$^9$ colony forming units of Lm-LLO-E7 (ADXS-HPV) at Days 1 and 15
9 patients pre- and initial post-vaccine tumor and blood samples collected.
An observational arm of 3 patients, who underwent transoral robotic surgery (TORS) without previous treatment with ADXS-HPV, also enrolled.
Key Inclusion Criteria
Adult patients (—18 years) with newly diagnosed, biopsy proven, stage II-IV HPVOPC.
Eligible to undergo TORS with or without neck dissection.
Eastern Cooperative Oncology Group performance status ≤2.
Able to understand and give informed consent.
Key Exclusion Criteria
Active cancer at another site, or history of cancer within the past 3 years.
Prior systemic chemotherapy or radiotherapy.
Immunosuppressive condition or taking immunosuppressive medication.
Liver disease or other medical contraindication to study medications.
Assays
Tissue Assays Carried Out Pre- and Post-Vaccine Administration
  Tumor Biopsy samples collected at the beginning of the study and at the time of surgery
  H&E histopathology
  Multiplex immunofluorescence
  Blood
  HPV antigen-specific T cell responses
  HPV serology
  Cancer-testis antigen serology
Analysis
Tissue-based changes are correlated with comprehensive analysis of immune changes in peripheral blood.

TABLE 7

| Laboratory studies | |
| --- | --- |
| Assay | Results |
| ELISPOT for HPV-E7-reactive T-cells in peripheral blood | ADXS-HPV induces robust systemic antigen-specific immunity |

TABLE 7-continued

Laboratory studies

| Assay | Results |
|---|---|
| IHC/IF for tumor-infiltrating CD8+ T-cells and other immunocytes | ADXS-HPV -induces T-cells penetration of the tumor and improves the overall balance of suppressor and effector immune cells in the TME |
| Immunophenotyping of suppressor and effector immune cell subsets in blood by flow cytometry | ADXS-HPV improves the systemic balance of suppressor and effector immunocytes. |
| Seroreactivity to HPV antigens and HNSCCA-associated cancer-testis antigens in blood | Targeting a foreign viral antigen (E7) leads to epitope spreading and induction of a broad-based response to self-derived tumor antigens |
| Immune gene expression signatures in TME by Nanostring | ADXS-HPV is associated with an "immune response signature" of altered gene expression. Identification of potential molecular targets for combination therapy |
| Multiplex serum cytokine and soluble immunomodulator levels by Luminex analysis | ADXS-HPV induces a durable inflammatory/cytokine signature |
| T-cell receptor diversity profiling by Immunoseq TCR deep sequencing | ADXS-HPV treatment affects the depth and breadth of the tumor-infiltrating T-cell repertoire |

ELISPOT, Enzyme-Linked ImmunoSpot; HNSCCA, human head and neck squamous cell carcinoma antigen; HPV, human papillomavirus; IF, immunofluorescence; IHC, immunohistochemistry; TCR, T-cell receptor; TME, tumor microenvironment.

Results

Figure 28A:
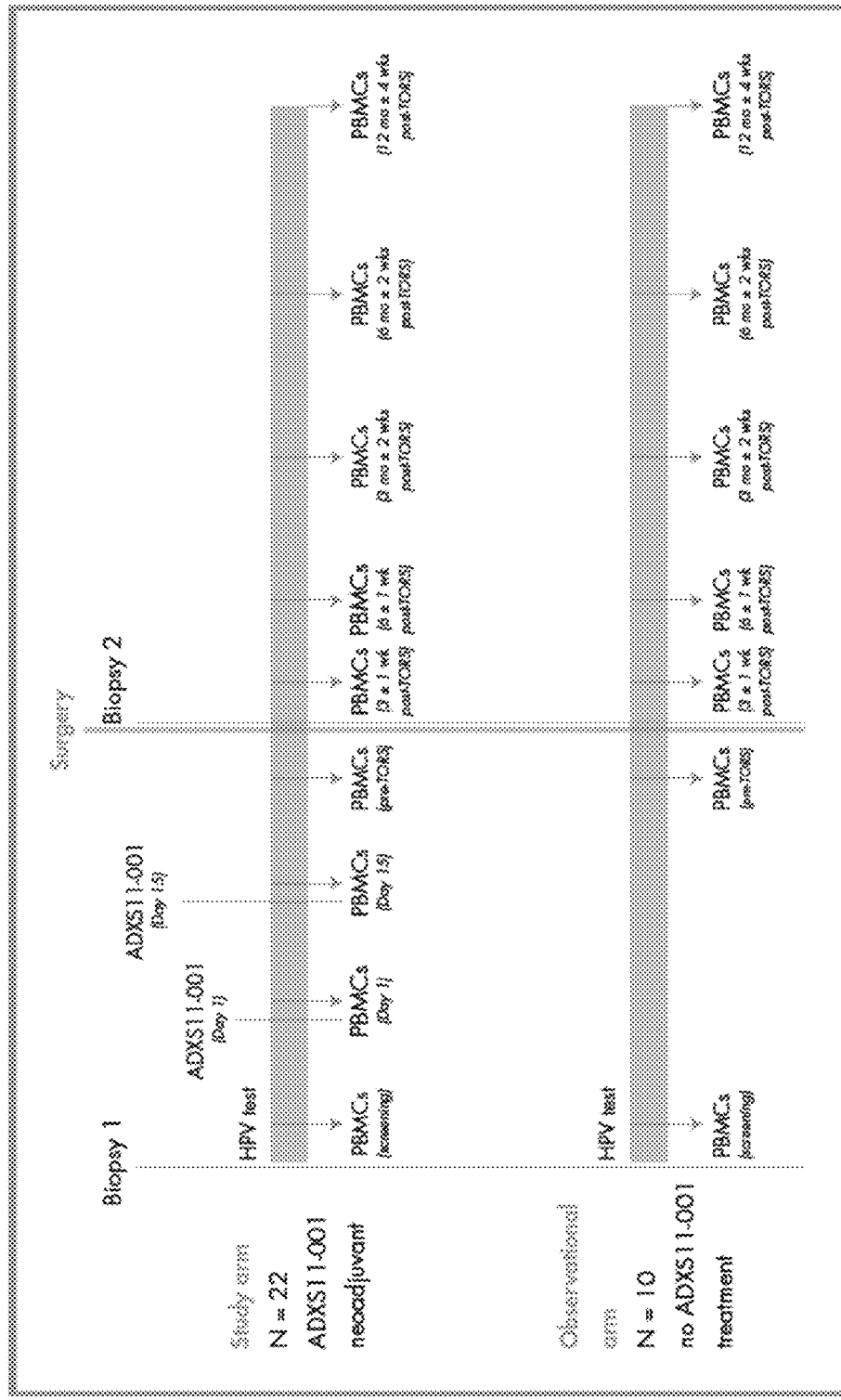
Figure 29:
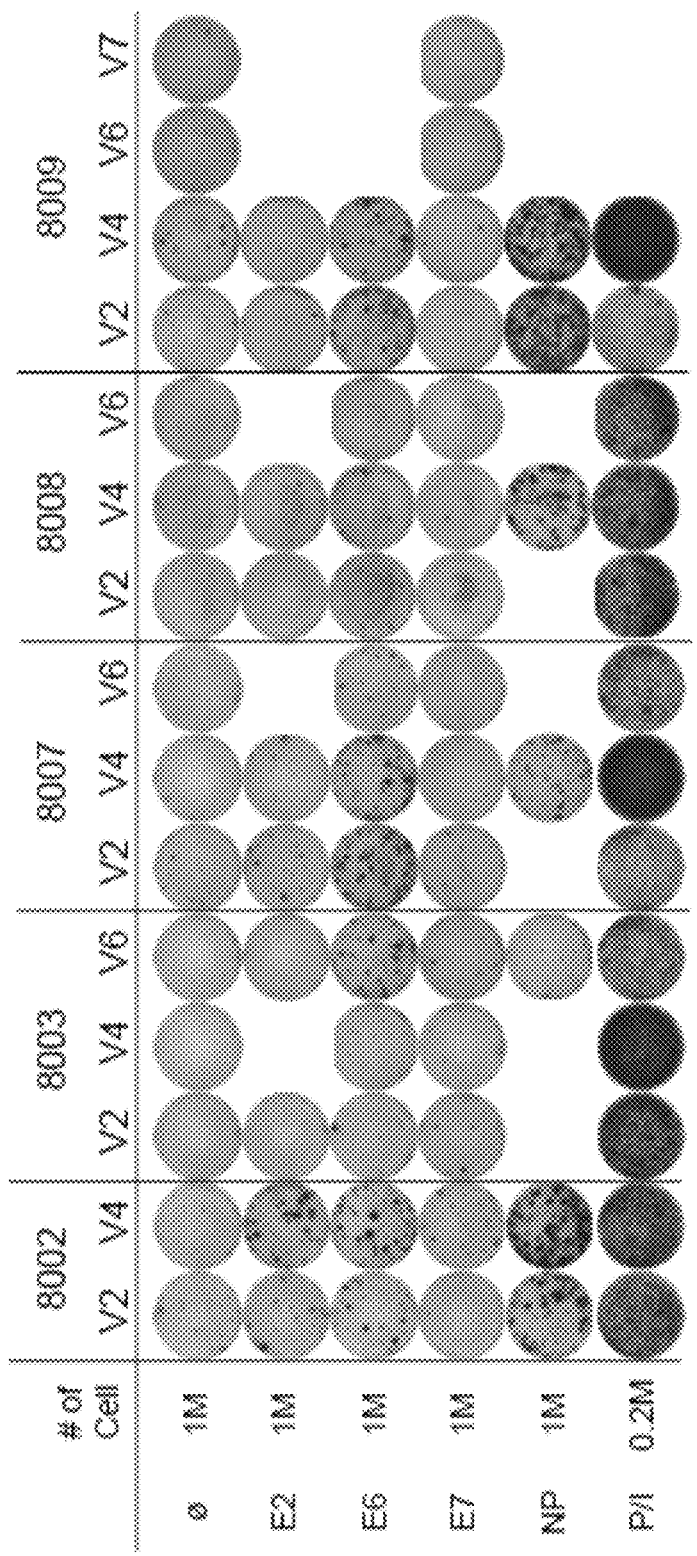
FIG. 29. ELISPOT—Direct analysis showing that there is an increase in systemic HPV-E6 and HPV E7 response post vaccination with ADXS-HPV. The first column designates the ELISPOT targets. Null: no peptide stimulation, E2: stimulation of HPV E2 peptide (demonstrating T-cell responses to HPV in general), E6 and E7: stimulation of HPV E6 and E7 peptides respectively (the early peptide genes associated with HPV Dysplasia), P/I: the positive control.
Figure 33A:
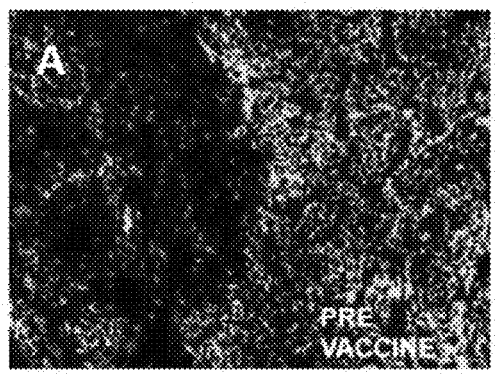
FIGS. 33A-33D show multiplex immunofluorescence of patient tumor.
Figure 33B:
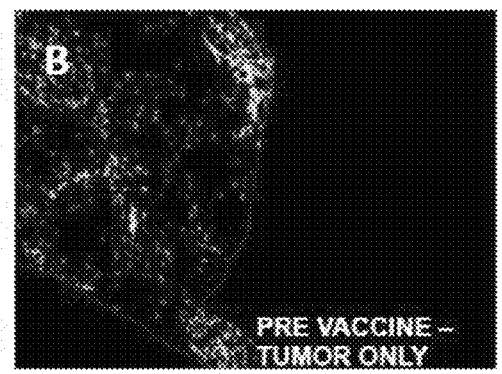
Figure 33C:
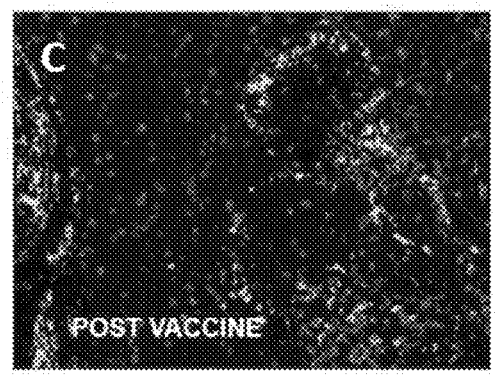
Figure 33D:
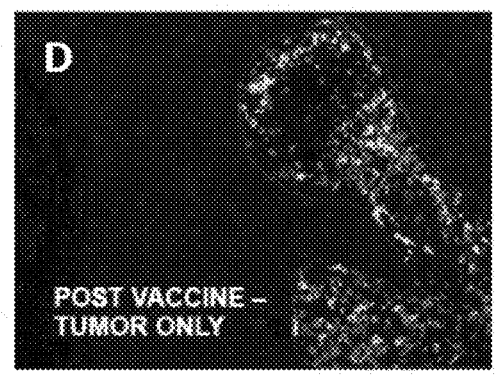
Figures 34A, 34B, 34C:
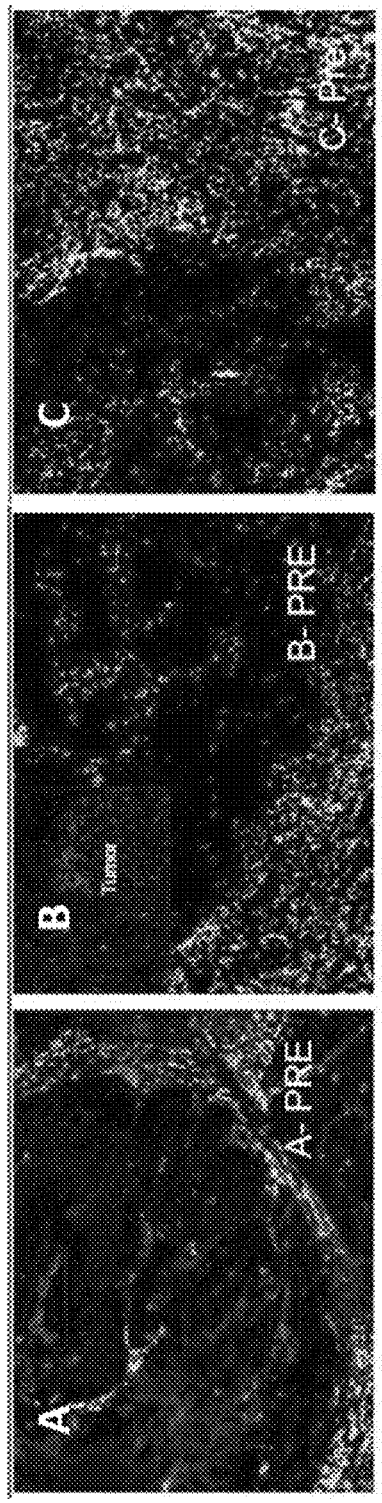
FIG. 34A-F. Multiplex immunofluorescence of patient tumor.
Figures 34D, 34E, 34F:
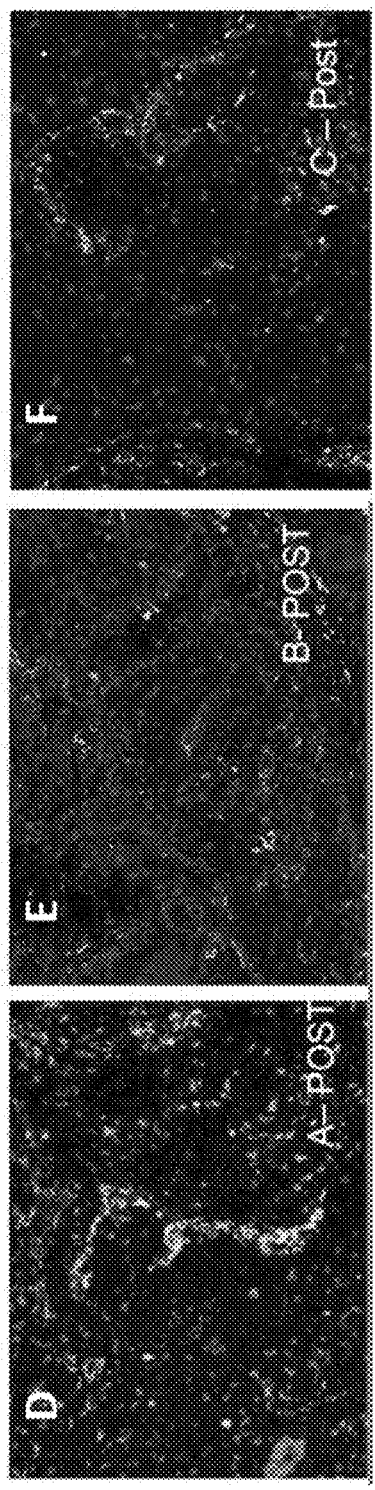
Figure 36:
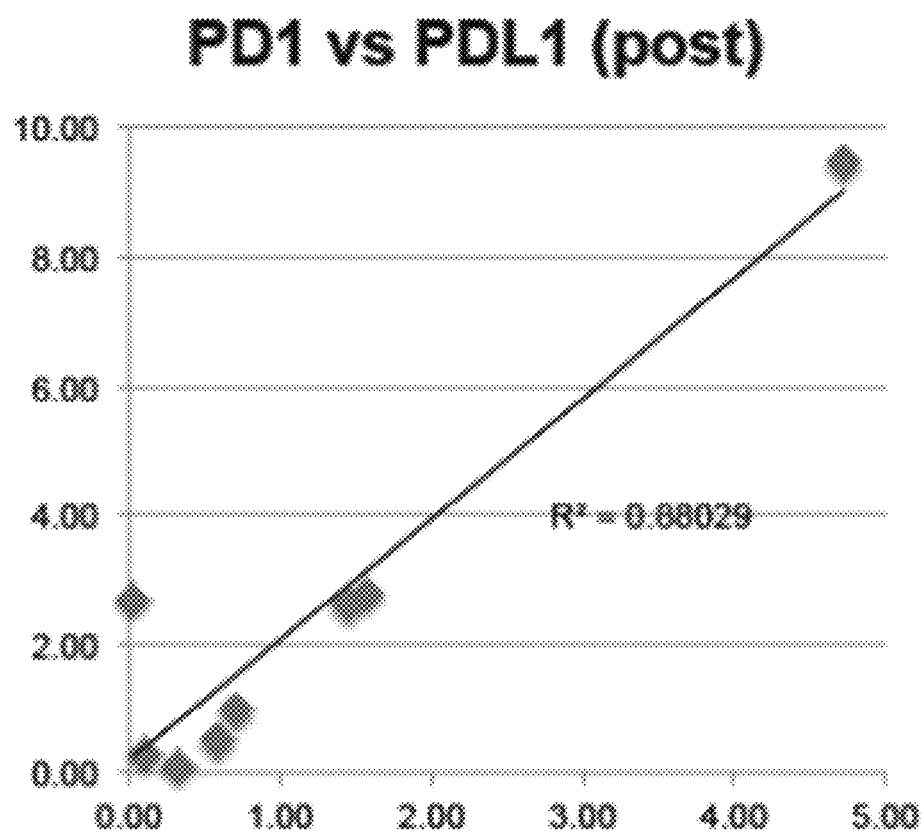
FIG. 36. Relative levels of PD-1 and PD-L1 in samples of ADXS-HPV vaccinated patients after vaccination. The levels of PD-1 are plotted along X the axis. The levels of PD-L1 are plotted along Y the axis.
Figure 37:
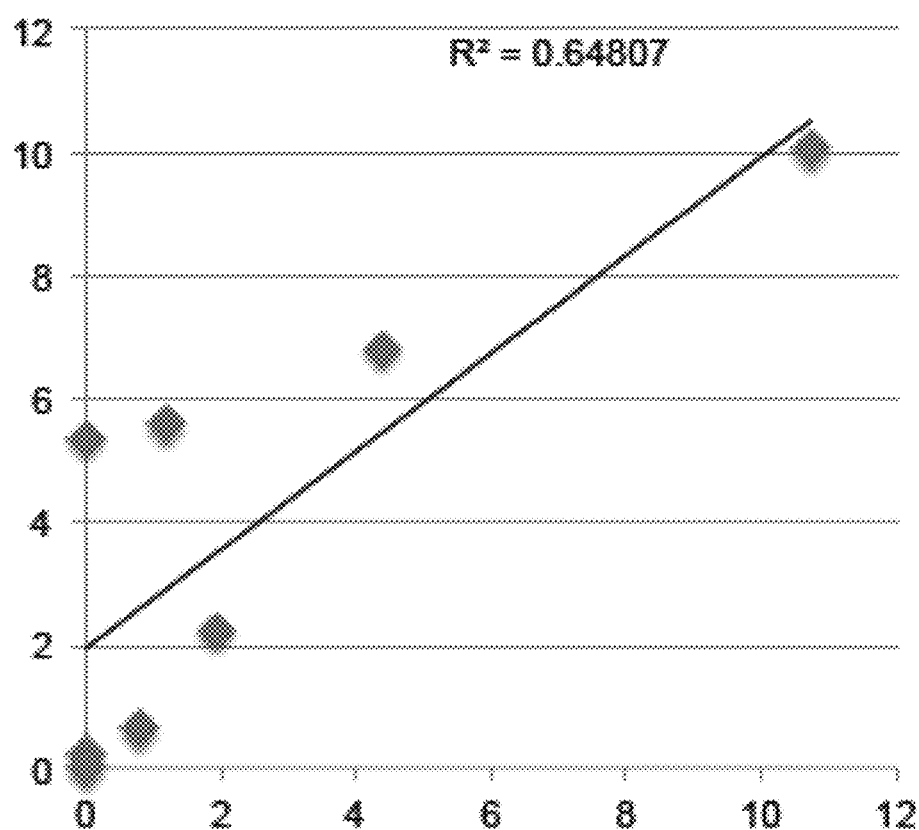
FIG. 37. Relative change in levels of CD8+ cells in samples of ADXS-HPV vaccinated patients before and after vaccination. The levels of CD8+ cells after vaccination are plotted along X the axis. The levels of CD8+ cells before vaccination are plotted along Y the axis.

The overall design of study is shown in FIG. 28A. Total of 11 patients with stage II-IV HPVOPC were enrolled in the trial. Tumor biopsies were collected from each patient prior to the beginning of the study. Eight patients were vaccinated with $1\times10^9$ colony forming units of Lm-LLO-E7 (ADXS-HPV), receiving a booster injection 14 days after first injection An observational arm of 3 patients with stage II-IV HPVOPC, who did not receive vaccinations, were also enrolled. Ibuprofen, diphenhydramine, and an antiemetic were given before ADXS-HPV infusion, with ibuprofen also administered after infusion; a course of amoxicillin (or alternative antibiotic) was administered 72 hours after each ADXS-HPV dosing. All the patients underwent standard of care transoral robotic surgery (TORS) to remove a sample of the tumor 10-14 days after the booster injection Adjuvant radiation/chemoradiation was administered to all patients as per standard of care (4-6 weeks after TORS). 1-10 days prior to vaccination peripheral blood mononuclear cells (PBMCs) samples were collected from all but two patients receiving vaccine. Additional PBMCs samples were collected from all patients prior to the each injection of the vaccine, as well as prior to surgery. Further PBMCs samples are drawn at different time points up to 12 months after initial vaccination (FIG. 28B). The ELISPOT assays of the samples shown increase in both E6 and E7 response following vaccination in some patients (FIG. 29), as well as increase in levels of E-6 and E7-specific IFN-gamma-secreting CD4$^+$ and CD8$^+$ T cells (FIG. 30A-D). In addition, some patients demonstrated even more robust induction of E-6 and E7-specific TNF-alpha-secreting CD4$^+$ and CD8$^+$ T cells at the time of surgery (FIG. 31A-D). Overall 5/8 patients have IFN-gamma response to E7 or E6, and 7/8 patients have TNF-alpha response to E7 or E6 (FIG. 32A-D). Multiplex immunofluorescence assays shown dense intratumoral CD8 infiltration of tumor milieu (compare FIGS. 33A and 33B) and decreased tumor size (compare FIGS. 33C and 33D) following vaccination with ADXS-HPV, as well as post-vaccine increase in CD8 and PD-1 in tumors (compare FIGS. 34 A-C and 34D-F). These observations were confirmed in quantitative analyses (FIG. 35A-H), which additionally shown increase in PD1 expression levels relative to PD-L1 (FIG. 36), and increase in CD8 expression levels following vaccination with ADXS-HPV (FIG. 37), demonstrating successful activation of anti E6 and E7 response by ADXS-HPV in cancer patients.

CONCLUSION

At the conclusion of the study HPV-specific CD8+ CTL responses in peripheral blood change from baseline at the time of surgery. This change is observable at various time points after surgery. Furthermore, the profile of tumor-infiltrating effector (natural killer [NK] cells, CD4+ and CD8+ T-cells) and suppressor (Treg and MDSC) immunocytes changes over the course of the study. Adverse events are assessed by the National Cancer Institute Common Terminology Criteria for Adverse Events version 4.0.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of inducing an anti-tumor or an anti-cancer immune response in a human subject having a tumor or cancer, the method comprising the step of administering to said subject a composition comprising a recombinant *Listeria* strain comprising a recombinant nucleic acid, said nucleic acid comprising a first open reading frame encoding a recombinant polypeptide comprising an N-terminal fragment of a listeriolysin O (LLO) protein fused to a heterologous antigen or fragment thereof, wherein said LLO protein comprises a sequence selected from SEQ ID NO: 2, SEQ ID NO: 4, AA 20-442 of SEQ ID NO: 1, or AA 1-420 of SEQ ID NO: 1, wherein said recombinant nucleic acid further comprises a second open reading frame encoding a mutant prfA gene or a metabolic enzyme, wherein said *Listeria* comprises a gene deletion or mutation, thereby inducing an immune response against a tumor or a cancer, wherein said tumor or cancer is a head and neck tumor or cancer, wherein said method further comprises administering a radiation or chemotherapeutic treatment in said subject, and wherein said immune response comprises reducing the severity of side effects associated with said a radiation or chemotherapeutic treatment in said subject.

2. The method of claim 1, wherein said head and neck tumor or cancer is an oropharyngeal tumor or cancer.

3. The method of claim 1, wherein said administering is intravenous administering.

4. The method of claim 1, wherein said recombinant *Listeria* strain is administered to said human subject at a dose of 1×10⁹-3.31×10¹⁰ organisms.

5. The method of claim 1, wherein said recombinant *Listeria* strain is a recombinant *Listeria monocytogenes* strain.

6. The method of claim 1, wherein said recombinant *Listeria* strain has been passaged through an animal host, prior to the step of administering.

7. The method of claim 1, wherein said recombinant polypeptide is expressed by said recombinant *Listeria* strain.

8. The method of claim 1, wherein said recombinant nucleic acid comprises an extrachromosomal plasmid that encodes said recombinant polypeptide.

9. The method of claim 1, wherein said second open reading frame encodes a mutant PrfA protein comprising a D133V mutation.

10. The method of claim 9, wherein said mutant PrfA protein complements a prfA genomic mutation or deletion in the recombinant *Listeria*.

11. The method of claim 1, wherein said *Listeria* strain comprises a mutation, deletion or inactivation in the genomic dal, dat, and actA genes.

12. The method of claim 11, wherein said metabolic enzyme complements said mutation, deletion or inactivation.

13. The method of claim 1, wherein said heterologous antigen is selected from the group consisting of human papilloma virus (HPV) HPV16 E6, HPV16 E7, HPV18 E6, and HPV18 E7 antigens.

14. The method of claim 1, further comprising the step of boosting said human subject with said recombinant *Listeria* strain.

15. The method of claim 1, further comprising the step of inoculating said human subject with an immunogenic composition that comprises said heterologous antigen or that directs expression of said heterologous antigen.

16. The method of claim 1, further comprising administering to said subject an adjuvant.

17. The method of claim 16, wherein said adjuvant is selected from the list consisting of a granulocyte/macrophage colony-stimulating factor (GM-CSF) protein, saponin QS21, monophosphoryl lipid A, SmithKline Beecham adjuvant system 2 (SBAS2), an unmethylated CpG-containing oligonucleotide, an immune-stimulating cytokine, a Quil glycoside, a bacterial toxin, and a bacterial mitogen.

18. The method of claim 1, wherein said recombinant *Listeria* strain has been stored in a frozen or lyophilized cell bank.

19. A method of treating or protecting a human subject against a tumor or cancer, comprising the step of administering to said subject the composition comprising the recombinant *Listeria* strain of claim 1.

20. A method for inducing an anti-tumor cytotoxic T cell response in a human subject, comprising the step of administering to said subject a composition comprising the recombinant *Listeria* strain according to the method of claim 1.

21. The method of claim 1, wherein said radiation or chemotherapeutic treatment in said subject is administered as a follow-up to the recombinant *Listeria* strain administration, wherein said immune response comprises reducing the severity of side effects associated with said follow-up radiation or chemotherapeutic treatment in said subject.

22. The method of claim 1, wherein said T effector cells comprise CD8+ T cells or CD4+ T cells.

23. The method of claim 21, wherein said method comprises administering at least one dose of said recombinant *Listeria* strain prior to or during said follow-up chemotherapeutic or radiation treatment.

24. The method of claim 21, wherein said method comprises administering said recombinant *Listeria* strain prior to or during said follow-up chemotherapeutic or radiation treatment.

25. A method of inducing an anti-tumor or an anti-cancer immune response in a human subject having a tumor or a cancer, the method comprising the step of administering to said subject a composition comprising a recombinant *Listeria* strain comprising a recombinant nucleic acid, said nucleic acid comprising a first open reading frame encoding a recombinant polypeptide comprising an N-terminal fragment of a listeriolysin O (LLO) protein, wherein said N-terminal fragment of an LLO protein comprises a sequence selected from SEQ ID NO: 2, SEQ ID NO: 4, AA 20-442 of SEQ ID NO: 1, or AA 1-420 of SEQ ID NO: 1 and is fused to a heterologous antigen or fragment thereof, wherein said heterologous antigen is selected from the group consisting of human papilloma virus (HPV) HPV16 E6, HPV16 E7, HPV18 E6, and HPV18 E7 antigens, said recombinant nucleic acid further comprising a second open reading frame encoding a mutant prfA gene or a metabolic enzyme, wherein said *Listeria* comprises a gene deletion or mutation, and wherein said method further comprises boosting said human subject with said recombinant *Listeria* strain or inoculating said human subject with an immunogenic composition that comprises said heterologous antigen or that directs expression of said heterologous antigen, thereby inducing an immune response against said heterologous antigen or fragment thereof in a tumor or a cancer, wherein said tumor or cancer is a head and neck tumor or cancer.

26. The method of claim 25, wherein said head and neck tumor or cancer is an oropharyngeal tumor or cancer.

27. The method of claim 1, wherein said immune response comprises increasing a level of interferon-gamma producing cells, increasing a level of TNF-alpha producing cells, an increase of tumor infiltration by T effector cells, inhibiting tumor-mediated immunosuppression in a subject, epitope spreading, increasing the ratio of effector T cells to regulatory T cells in the tumor microenvironment, or any combination thereof.

28. The method of claim 25, wherein said immune response comprises increasing a level of interferon-gamma producing cells, increasing a level of TNF-alpha producing cells, an increase of tumor infiltration by T effector cells, inhibiting tumor-mediated immunosuppression in a subject, epitope spreading, increasing the ratio of effector T cells to regulatory T cells in the tumor microenvironment, or any combination thereof.

* * * * *

SEQUENCE LISTING

<160> NUMBER OF SEQ ID NOS: 30

<210> SEQ ID NO 1

```
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 2
<211> LENGTH: 441
<212> TYPE: PRT
<213> ORGANISM: Listeria monocytogenes

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
            35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320
```

```
Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
            435                 440
```

<210> SEQ ID NO 3
<211> LENGTH: 529
<212> TYPE: PRT
<213> ORGANISM: Listeria monocytogenes

<400> SEQUENCE: 3

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
            35                  40                  45

Pro Lys Thr Pro Ile Glu Lys Lys His Ala Asp Glu Ile Asp Lys Tyr
        50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
        130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
        210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
```

```
                245                 250                 255
Asn Val Asn Val Asn Glu Pro Thr Arg Pro Ser Arg Phe Phe Gly Lys
            260                 265                 270
Ala Val Thr Lys Glu Gln Leu Gln Ala Leu Gly Val Asn Ala Glu Asn
        275                 280                 285
Pro Pro Ala Tyr Ile Ser Ser Val Ala Tyr Gly Arg Gln Val Tyr Leu
    290                 295                 300
Lys Leu Ser Thr Asn Ser His Ser Thr Lys Val Lys Ala Ala Phe Asp
305                 310                 315                 320
Ala Ala Val Ser Gly Lys Ser Val Ser Gly Asp Val Glu Leu Thr Asn
            325                 330                 335
Ile Ile Lys Asn Ser Ser Phe Lys Ala Val Ile Tyr Gly Gly Ser Ala
        340                 345                 350
Lys Asp Glu Val Gln Ile Ile Asp Gly Asn Leu Gly Asp Leu Arg Asp
    355                 360                 365
Ile Leu Lys Lys Gly Ala Thr Phe Asn Arg Glu Thr Pro Gly Val Pro
370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
            405                 410                 415
Gly Lys Ile Asn Ile Asp His Ser Gly Gly Tyr Val Ala Gln Phe Asn
        420                 425                 430
Ile Ser Trp Asp Glu Val Asn Tyr Asp Pro Glu Gly Asn Glu Ile Val
    435                 440                 445
Gln His Lys Asn Trp Ser Glu Asn Asn Lys Ser Lys Leu Ala His Phe
450                 455                 460
Thr Ser Ser Ile Tyr Leu Pro Gly Asn Ala Arg Asn Ile Asn Val Tyr
465                 470                 475                 480
Ala Lys Glu Cys Thr Gly Leu Ala Trp Glu Trp Trp Arg Thr Val Ile
            485                 490                 495
Asp Asp Arg Asn Leu Pro Leu Val Lys Asn Arg Asn Ile Ser Ile Trp
        500                 505                 510
Gly Thr Thr Leu Tyr Pro Lys Tyr Ser Asn Lys Val Asp Asn Pro Ile
    515                 520                 525
Glu

<210> SEQ ID NO 4
<211> LENGTH: 416
<212> TYPE: PRT
<213> ORGANISM: Listeria monocytogenes

<400> SEQUENCE: 4

Met Lys Lys Ile Met Leu Val Phe Ile Thr Leu Ile Leu Val Ser Leu
1               5                   10                  15
Pro Ile Ala Gln Gln Thr Glu Ala Lys Asp Ala Ser Ala Phe Asn Lys
            20                  25                  30
Glu Asn Ser Ile Ser Ser Val Ala Pro Pro Ala Ser Pro Pro Ala Ser
        35                  40                  45
Pro Lys Thr Pro Ile Glu Lys Lys His Ala Asp Glu Ile Asp Lys Tyr
    50                  55                  60
Ile Gln Gly Leu Asp Tyr Asn Lys Asn Asn Val Leu Val Tyr His Gly
65                  70                  75                  80
Asp Ala Val Thr Asn Val Pro Pro Arg Lys Gly Tyr Lys Asp Gly Asn
```

85                  90                  95
Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
            130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
            210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
            290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
            325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
            385                 390                 395                 400

Lys Asn Asn Ser Glu Tyr Ile Glu Thr Thr Ser Lys Ala Tyr Thr Asp
            405                 410                 415

<210> SEQ ID NO 5
<211> LENGTH: 390
<212> TYPE: PRT
<213> ORGANISM: Listeria monocytogenes

<400> SEQUENCE: 5

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
                20                  25                  30

Asn Thr Asp Glu Trp Glu Glu Glu Lys Thr Glu Glu Gln Pro Ser Glu
            35                  40                  45

```
Val Asn Thr Gly Pro Arg Tyr Glu Thr Ala Arg Glu Val Ser Ser Arg
 50                  55                  60

Asp Ile Lys Glu Leu Glu Lys Ser Asn Lys Val Arg Asn Thr Asn Lys
 65                  70                  75                  80

Ala Asp Leu Ile Ala Met Leu Lys Glu Lys Ala Glu Lys Gly Pro Asn
                 85                  90                  95

Ile Asn Asn Asn Ser Glu Gln Thr Glu Asn Ala Ala Ile Asn Glu
                100                 105                 110

Glu Ala Ser Gly Ala Asp Arg Pro Ala Ile Gln Val Glu Arg Arg His
                115                 120                 125

Pro Gly Leu Pro Ser Asp Ser Ala Ala Glu Ile Lys Lys Arg Arg Lys
130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
                180                 185                 190

Ser Ser Pro Gln Pro Leu Lys Ala Asn Gln Gln Pro Phe Phe Pro Lys
                195                 200                 205

Val Phe Lys Lys Ile Lys Asp Ala Gly Lys Trp Val Arg Asp Lys Ile
210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
                260                 265                 270

Pro Glu Thr Pro Met Leu Leu Gly Phe Asn Ala Pro Ala Thr Ser Glu
                275                 280                 285

Pro Ser Ser Phe Glu Phe Pro Pro Pro Thr Asp Glu Glu Leu Arg
290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
                340                 345                 350

Thr Arg Gly Asp Leu Ala Ser Leu Arg Asn Ala Ile Asn Arg His Ser
                355                 360                 365

Gln Asn Phe Ser Asp Phe Pro Pro Ile Pro Thr Glu Glu Glu Leu Asn
370                 375                 380

Gly Arg Gly Gly Arg Pro
385                 390

<210> SEQ ID NO 6
<211> LENGTH: 1170
<212> TYPE: DNA
<213> ORGANISM: Listeria monocytogenes

<400> SEQUENCE: 6
atgcgtgcga tgatggtggt tttcattact gccaattgca ttacgattaa ccccgacata      60
atatttgcag cgacagatag cgaagattct agtctaaaca cagatgaatg gaagaagaa      120 aaaacagaag agcaaccaag cgaggtaaat acgggaccaa gatacgaaac tgcacgtgaa      180
```

```
gtaagttcac gtgatattaa agaactagaa aaatcgaata aagtgagaaa tacgaacaaa      240
gcagacctaa tagcaatgtt gaaagaaaaa gcagaaaaag gtccaaatat caataataac      300
aacagtgaac aaactgagaa tgcggctata aatgaagagg cttcaggagc cgaccgacca      360
gctatacaag tggagcgtcg tcatccagga ttgccatcgg atagcgcagc ggaaattaaa      420
aaaagaagga aagccatagc atcatcggat agtgagcttg aaagcettac ttatccggat      480 aaaccaacaa aagtaaataa gaaaaaagtg gcgaaagagt cagttgcgga tgcttctgaa      540
agtgacttag attctagcat gcagtcagca gatgagtctt caccacaacc tttaaaagca      600
aaccaacaac cattttttccc taaagtattt aaaaaaataa aagatgcggg gaaatgggta      660
cgtgataaaa tcgacgaaaa tcctgaagta agaaagcga ttgttgataa aagtgcaggg      720
ttaattgacc aattattaac caaaaagaaa agtgaagagg taaatgcttc ggacttcccg      780
ccaccaccta cggatgaaga gttaagactt gctttgccag agacaccaat gcttcttggt      840
tttaatgctc ctgctacatc agaaccgagc tcattcgaat tccaccacc acctacggat      900 gaagagttaa gacttgctt gccagagacg ccaatgcttc ttggttttaa tgctcctgct      960
acatcggaac cgagctcgtt cgaatttcca ccgcctccaa cagaagatga actagaaatc     1020
atccgggaaa cagcatcctc gctagattct agttttacaa gaggggattt agctagtttg     1080
agaaatgcta ttaatcgcca tagtcaaaat ttctctgatt tcccaccaat cccaacagaa     1140
gaagagttga acgggagagg cggtagacca                                      1170
```

<210> SEQ ID NO 7
<211> LENGTH: 14
<212> TYPE: PRT
<213> ORGANISM: Listeria monocytogenes

<400> SEQUENCE: 7

Lys Thr Glu Glu Gln Pro Ser Glu Val Asn Thr Gly Pro Arg
1               5                   10

<210> SEQ ID NO 8
<211> LENGTH: 28
<212> TYPE: PRT
<213> ORGANISM: Listeria monocytogenes

<400> SEQUENCE: 8

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 9
<211> LENGTH: 20
<212> TYPE: PRT
<213> ORGANISM: Listeria monocytogenes

<400> SEQUENCE: 9

Lys Asn Glu Glu Val Asn Ala Ser Asp Phe Pro Pro Pro Thr Asp
1               5                   10                  15

Glu Glu Leu Arg
            20

<210> SEQ ID NO 10
<211> LENGTH: 33
<212> TYPE: PRT
<213> ORGANISM: Listeria monocytogenes -continued

<400> SEQUENCE: 10

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Ile Asp
            20                  25                  30

Arg

<210> SEQ ID NO 11
<211> LENGTH: 17
<212> TYPE: PRT
<213> ORGANISM: Streptococcus sp. G148

<400> SEQUENCE: 11

Lys Gln Asn Thr Ala Ser Thr Glu Thr Thr Thr Thr Asn Glu Gln Pro
1               5                   10                  15

Lys

<210> SEQ ID NO 12
<211> LENGTH: 17
<212> TYPE: PRT
<213> ORGANISM: Streptococcus equisimilis

<400> SEQUENCE: 12

Lys Gln Asn Thr Ala Asn Thr Glu Thr Thr Thr Thr Asn Glu Gln Pro
1               5                   10                  15

Lys

<210> SEQ ID NO 13
<211> LENGTH: 98
<212> TYPE: PRT
<213> ORGANISM: Human papillomavirus type 16

<400> SEQUENCE: 13

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 14
<211> LENGTH: 105
<212> TYPE: PRT
<213> ORGANISM: Human papillomavirus type 16

<400> SEQUENCE: 14

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
            20                  25                  30

Asp Ser Glu Glu Asn Asp Glu Ile Asp Gly Val Asn His Gln His
         35                  40                  45

Leu Pro Ala Arg Arg Ala Glu Pro Gln Arg His Thr Met Leu Cys Met
 50                  55                  60

Cys Cys Lys Cys Glu Ala Arg Ile Glu Leu Val Val Glu Ser Ser Ala
65                  70                  75                  80

Asp Asp Leu Arg Ala Phe Gln Gln Leu Phe Leu Asn Thr Leu Ser Phe
             85                  90                  95

Val Cys Pro Trp Cys Ala Ser Gln Gln
             100                 105

<210> SEQ ID NO 15
<211> LENGTH: 158
<212> TYPE: PRT
<213> ORGANISM: Human papillomavirus type 16

<400> SEQUENCE: 15

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
             20                  25                  30

Ile Ile Leu Glu Cys Val Tyr Cys Lys Gln Gln Leu Leu Arg Arg Glu
         35                  40                  45

Val Tyr Asp Phe Ala Phe Arg Asp Leu Cys Ile Val Tyr Arg Asp Gly
 50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
             85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu
145                 150                 155

<210> SEQ ID NO 16
<211> LENGTH: 158
<212> TYPE: PRT
<213> ORGANISM: Human papillomavirus type 16

<400> SEQUENCE: 16

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
             20                  25                  30

Val Tyr Cys Lys Thr Val Leu Glu Leu Thr Glu Val Phe Glu Phe Ala
         35                  40                  45

Phe Lys Asp Leu Phe Val Val Tyr Arg Asp Ser Ile Pro His Ala Ala
 50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
             85                  90                  95

-continued

```
Gly Leu Tyr Asn Leu Leu Ile Arg Cys Leu Arg Cys Gln Lys Pro Leu
                100                 105                 110

Asn Pro Ala Glu Lys Leu Arg His Leu Asn Glu Lys Arg Arg Phe His
            115                 120                 125

Asn Ile Ala Gly His Tyr Arg Gly Gln Cys His Ser Cys Cys Asn Arg
        130                 135                 140

Ala Arg Gln Glu Arg Leu Gln Arg Arg Glu Thr Gln Val
145                 150                 155

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
ggctcgagca tggagataca cc                                            22

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
ggggactagt ttatggtttc tgagaaca                                      28

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
gggggctagc cctcctttga ttagtatatt c                                  31

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
ctccctcgag atcataattt acttcatc                                      28

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
cccgtcgacc agctcttctt ggtgaag                                       27

<210> SEQ ID NO 22
<211> LENGTH: 25
<212> TYPE: DNA
<213> ORGANISM: Artificial Sequence
<220> FEATURE:
<223> OTHER INFORMATION: Primer
```

<400> SEQUENCE: 22
gcggatccca tggagataca cctac                                    25

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
gctctagatt atggtttctg ag                                       22

<210> SEQ ID NO 24
<211> LENGTH: 9
<212> TYPE: PRT
<213> ORGANISM: Human papillomavirus type 16

<400> SEQUENCE: 24

Arg Ala His Tyr Asn Ile Val Thr Phe
1               5

<210> SEQ ID NO 25
<211> LENGTH: 9
<212> TYPE: PRT
<213> ORGANISM: Human immunodeficiency virus

<400> SEQUENCE: 25

Ala Met Gln Met Leu Lys Glu Thr Ile
1               5

<210> SEQ ID NO 26
<211> LENGTH: 9
<212> TYPE: PRT
<213> ORGANISM: Listeria monocytogenes

<400> SEQUENCE: 26

Gly Tyr Lys Asp Gly Asn Glu Tyr Ile
1               5

<210> SEQ ID NO 27
<211> LENGTH: 55
<212> TYPE: PRT
<213> ORGANISM: Artificial Sequence
<220> FEATURE:
<223> OTHER INFORMATION: Primer

<400> SEQUENCE: 27

Gly Ala Cys Thr Ala Cys Ala Ala Gly Gly Ala Cys Gly Ala Thr Gly
1               5                   10                  15

Ala Cys Cys Gly Ala Cys Ala Ala Gly Thr Gly Ala Thr Ala Ala Cys
                20                  25                  30

Cys Cys Gly Gly Gly Ala Thr Cys Thr Ala Ala Thr Ala Ala Ala
            35                  40                  45

Thr Cys Cys Gly Thr Thr Thr
    50                  55

<210> SEQ ID NO 28
<211> LENGTH: 18
<212> TYPE: DNA
<213> ORGANISM: Artificial Sequence
<220> FEATURE:
<223> OTHER INFORMATION: ADV451 forward primer

```
<400> SEQUENCE: 28
cctagctaaa tttaatgt                                                   18

<210> SEQ ID NO 29
<211> LENGTH: 18
<212> TYPE: DNA
<213> ORGANISM: Artificial Sequence
<220> FEATURE:
<223> OTHER INFORMATION: ADV452 forward primer

<400> SEQUENCE: 29
cctagctaaa tttaatga                                                   18

<210> SEQ ID NO 30
<211> LENGTH: 21
<212> TYPE: DNA
<213> ORGANISM: Artificial Sequence
<220> FEATURE:
<223> OTHER INFORMATION: ADV453 reverse primer

<400> SEQUENCE: 30
taattttccc caagtagcag g                                               21
```